United States Patent
Vidugiriene et al.

(10) Patent No.: US 12,061,202 B2
(45) Date of Patent: Aug. 13, 2024

(54) COMPOSITIONS AND METHODS FOR BIOLUMINESCENT DETECTION USING MULTIFUNCTIONAL PROBES

(71) Applicant: Promega Corporation, Madison, WI (US)

(72) Inventors: Jolanta Vidugiriene, Madison, WI (US); Peter Hofsteen, Madison, WI (US); James J. Cali, Verona, WI (US); Sarah Duellman, Madison, WI (US); Hui Wang, Madison, WI (US); Natasha Karassina, Madison, WI (US); Wenhui Zhou, Madison, WI (US)

(73) Assignee: Promega Corporation, Madison, WI (US)

( * ) Notice: Subject to any disclaimer, the term of this patent is extended or adjusted under 35 U.S.C. 154(b) by 531 days.

(21) Appl. No.: 17/116,802

(22) Filed: Dec. 9, 2020

(65) Prior Publication Data
US 2021/0190789 A1 Jun. 24, 2021

Related U.S. Application Data

(60) Provisional application No. 62/946,237, filed on Dec. 10, 2019.

(51) Int. Cl.
G01N 33/58 (2006.01)
G01N 33/545 (2006.01)

(52) U.S. Cl.
CPC ......... *G01N 33/582* (2013.01); *G01N 33/545* (2013.01)

(58) Field of Classification Search
CPC .............. C07D 207/46; C07D 491/107; G01N 33/57484; G01N 33/582; G01N 33/545; G01N 2333/914
See application file for complete search history.

(56) References Cited

U.S. PATENT DOCUMENTS

| 4,946,778 A | 8/1990 | Ladner et al. |
| 5,260,203 A | 11/1993 | Ladner et al. |

(Continued)

FOREIGN PATENT DOCUMENTS

| WO | WO 88/01649 | 3/1988 |
| WO | WO 2003/040100 | 5/2003 |

(Continued)

OTHER PUBLICATIONS

Donnenberg et al. Current good manufacturing practicescompliant manufacture and measurement of biotin-labeled red blood cells. Cytotherapy, 2019; vol. 21; pp. 793-800. (Year: 2019).*

(Continued)

*Primary Examiner* — Shafiqul Haq
(74) *Attorney, Agent, or Firm* — David W. Staple; Casimir Jones, S.C.

(57) ABSTRACT

Provided herein are materials and methods for performing bioluminescent assays using a bifunctional probe. In particular, the present disclosure provides compositions and methods for detecting and/or quantifying a biomolecule and/or assaying a cellular process associated with the biomolecule using a bifunctional probe capable of binding the biomolecule and generating a bioluminescent and/or fluorescent signal.

9 Claims, 13 Drawing Sheets
(12 of 13 Drawing Sheet(s) Filed in Color)
Specification includes a Sequence Listing.

(56) References Cited

U.S. PATENT DOCUMENTS

| | | |
|---|---|---|
| 7,238,842 B2 | 7/2007 | Wood et al. |
| 7,425,436 B2 | 9/2008 | Darzins et al. |
| 7,429,472 B2 | 9/2008 | Darzins et al. |
| 7,867,726 B2 | 1/2011 | Wood et al. |
| 8,557,970 B2 | 10/2013 | Encell et al. |
| 8,669,103 B2 | 3/2014 | Binkowski et al. |
| 9,056,885 B2 | 6/2015 | Kirkland et al. |
| 9,797,889 B2 | 10/2017 | Dixon et al. |
| 9,977,586 B2 | 5/2018 | Yoshinaka |
| 2008/0248511 A1 | 10/2008 | Daily et al. |
| 2012/0107849 A1 | 5/2012 | Klaubert et al. |
| 2014/0099654 A1 | 4/2014 | Cali et al. |
| 2017/0233789 A1 | 8/2017 | Shakhmin et al. |
| 2018/0030059 A1 | 2/2018 | Hall et al. |
| 2020/0270586 A1 | 8/2020 | Hall et al. |

FOREIGN PATENT DOCUMENTS

| | | |
|---|---|---|
| WO | WO 2010/127368 | 11/2010 |
| WO | WO 2012/061529 | 5/2012 |
| WO | WO 2012/061530 | 5/2012 |
| WO | WO 2014/093677 | 6/2014 |
| WO | WO 2014/151282 A1 | 9/2014 |
| WO | WO 2014/151736 | 9/2014 |
| WO | WO 2019/241438 | 12/2019 |

OTHER PUBLICATIONS

Ohana et al. Deciphering the Cellular Targets of Bioactive Compounds Using a Chloroalkane Capture Tag. ACS Chem. Biol. 2015, vol. 10, pp. 2316-2324. (Year: 2015).*

Chidley et al., A designed protein for the specific and covalent heteroconjugation of biomolecules. Bioconjug Chem. Sep. 2008;19(9):1753-6.

Feng et al., Improved split fluorescent proteins for endogenous protein labeling. Nat Commun. Aug. 29, 2017;8(1):370.

Foglieni et al., Split GFP technologies to structurally characterize and quantify functional biomolecular interactions of FTD-related proteins. Sci Rep. Oct. 25, 2017;7(1):14013.

Greene, Protective Groups in Organic Synthesis (4th ed.), John Wiley & Sons, NY (2006).

Hudson et al., Engineered antibodies. Nat Med. Jan. 2003;9(1):129-34.

Koraichi et al., High-content tripartite split-GFP cell-based assays to screen for modulators of small GTPase activation. J Cell Sci. Jan. 8, 2018;131(1):jcs210419.

Satpati et al., Preparation and bioevaluation of a 99mTc-labeled chlorambucil analog as a tumor targeting agent. Appl Radiat Isot. Sep. 2009;67(9):1644-9.

International Search Report and Written Opinion for PCT/US2020/064047. Mailed Mar. 17, 2021. 17 pages.

* cited by examiner

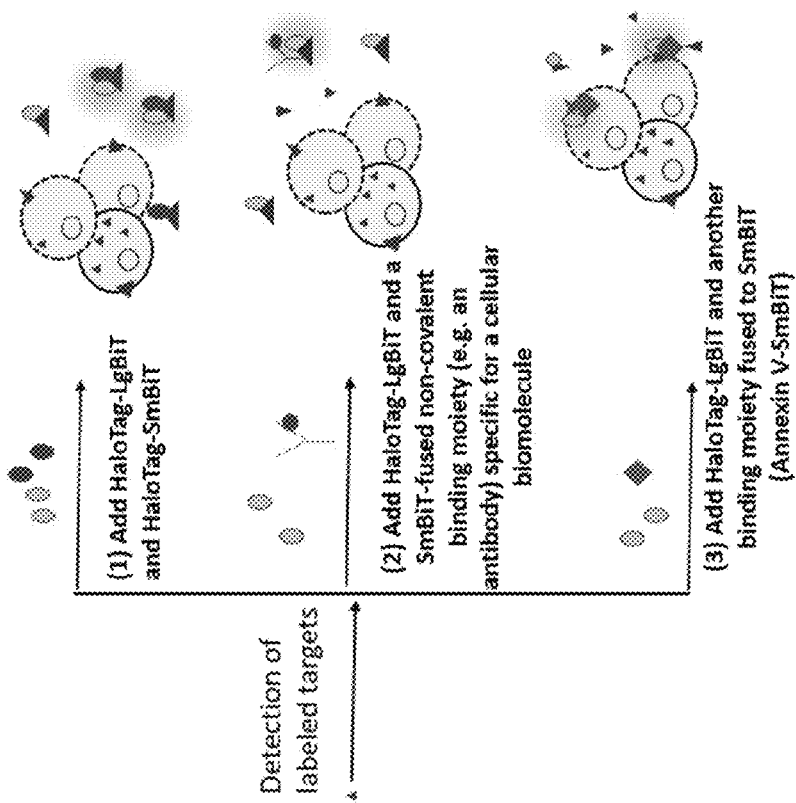
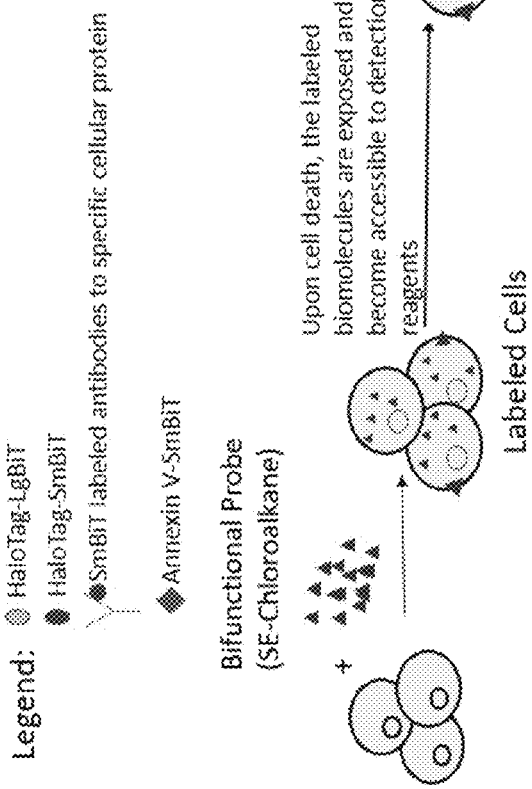
FIG. 1B

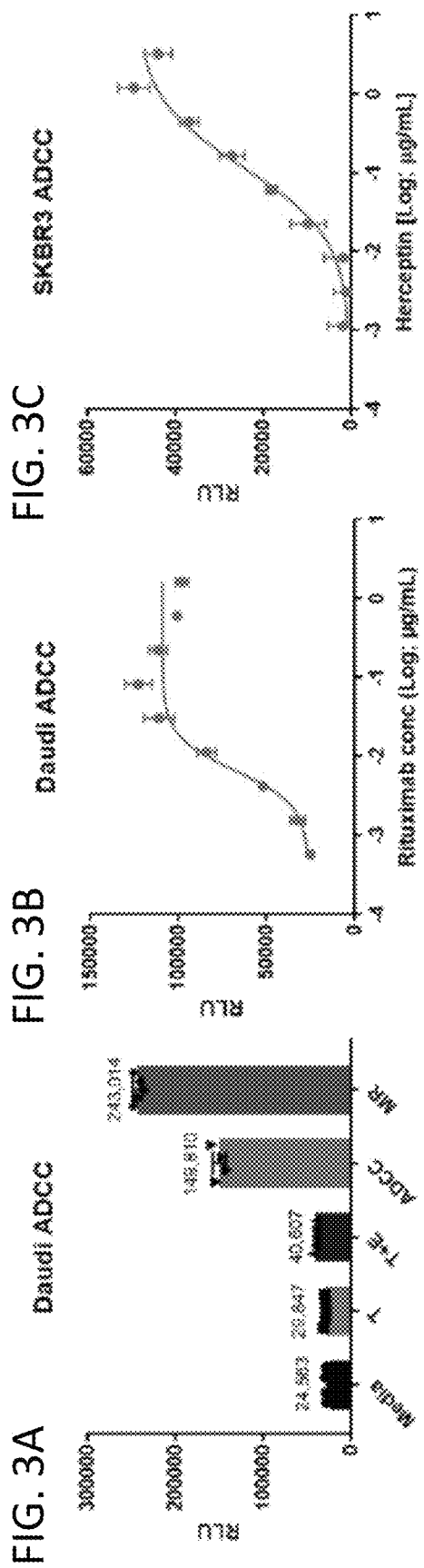

COMPOSITIONS AND METHODS FOR BIOLUMINESCENT DETECTION USING MULTIFUNCTIONAL PROBES

CROSS-REFERENCE TO RELATED APPLICATION

The present application claims priority to U.S. Provisional Patent Application Ser. No. 62/946,237 filed Dec. 10, 2019, which is hereby incorporated by reference in its entirety.

FIELD

Provided herein are materials and methods for performing bioluminescent assays using a multifunctional probe (e.g., bifunctional, trifunctional, etc.). In particular, the present disclosure provides compositions and methods for detecting and/or quantifying a biomolecule and/or assaying a cellular process associated with the biomolecule using a multifunctional probe capable of binding the biomolecule and generating a bioluminescent and/or fluorescent signal.

BACKGROUND

Cell-based assays are an essential part of assessing cellular responses to various environmental stimuli, especially in the context of drug discovery, as they provide a simple, efficient, and cost-effective alternative to animal testing. Since results of cell-based assays are typically reliant on cellular responses to drugs, compounds, external stimuli, etc., the key element to generating consistent and accurate experimental results is the use of cultured cells. Currently, the majority of cell-based assays use traditional two-dimensional (2D) monolayer cells cultured on flat and rigid substrates. Although 2D cell culture has been a valuable method for cell-based studies, it has several limitations. For example, since almost all cells in an in vivo environment are surrounded by other cells and extracellular matrix (ECM) in a three-dimensional (3D) fashion, 2D cell culture does not adequately take into account the natural 3D environment of cells. However, experiments conducted using co-cultured cells, both in the 2D and 3D cell culture formats, are hindered by the technical challenges of specifically labeling one cell population and/or one set of cellular proteins in order to generate accurate data reflecting the responses of the cells to environmental stimuli. For example, it is advantageous to measure the responses of specific cell populations within a heterogenous mixture of cells such as measuring the death of targeted cancer cells caused by cytotoxic T lymphocytes (CTLs) or natural killer (NK) cells with chimeric antigen receptors (CARs). Often times, the non-specific release of labeling probes from the live cells restricts the usefulness of these types of studies to only short-term measurements instead of a more physiologically-relevant timescale. Therefore, there is a need for cell-based assays and systems that facilitate the specific labeling of cells and/or proteins within the context of co-culture environments.

SUMMARY

In some embodiments, provided herein are compositions comprising a compound of formula (I):

A-X-B      (I)

or a salt thereof, wherein: A is a capture element; X is a linker; and B is a biomolecule-reactive group. In some embodiments, A is a covalent substrate for an enzyme. In some embodiments, A comprises a haloalkyl group. In some embodiments, A has the formula —(CH$_2$)$_n$—X, wherein: n is 4, 5, 6, 7, or 8; and X is a halogen. In some embodiments, A has formula —(CH$_2$)$_6$—Cl. In some embodiments, B is a protein-reactive group capable of forming a covalent bond with an amino group on a protein. In some embodiments, B is selected from a succinimidyl ester, a maleimide, an isocyanate, an isothiocyanate, a pentafluorophenyl ester, and a tetrafluorophenyl ester. In some embodiments, B is a succinimidyl ester. In some embodiments, B is maleimide. In some embodiments, the linker comprises one or more groups independently selected from alkylene, arylene, —O—, —NH—, carbamate, and —C(O)— groups. In some embodiments, the linker comprises a group of formula:

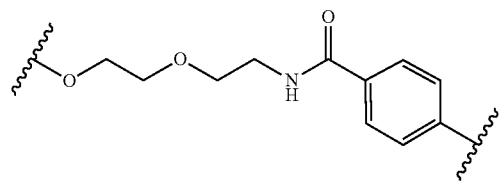

In some embodiments, the linker comprises a carbon or nitrogen atom that is substituted with a second capture element A'. In some embodiments, A' is connected to the carbon or nitrogen atom by a second linker (linker'). In some embodiments, the linker' comprises one or more groups independently selected from alkylene, arylene, —O—, —NH—, carbamate, and —C(O)— groups. In some embodiments, A' comprises a haloalkyl group. In some embodiments, A' has the formula —(CH$_2$)$_6$—Cl. In some embodiments, the linker comprises a carbon or nitrogen atom that is substituted with a fluorophore. In some embodiments, the fluorophore is connected to the carbon or nitrogen atom by a linker (linker"). In some embodiments, linker" comprises one or more groups independently selected from alkylene, arylene, —O—, —NH—, carbamate, and —C(O)— groups. In some embodiments, the compound is cell permeable. In some embodiments, the compound is selected from:

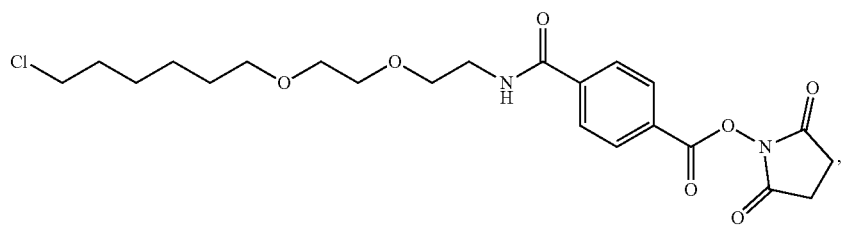

-continued

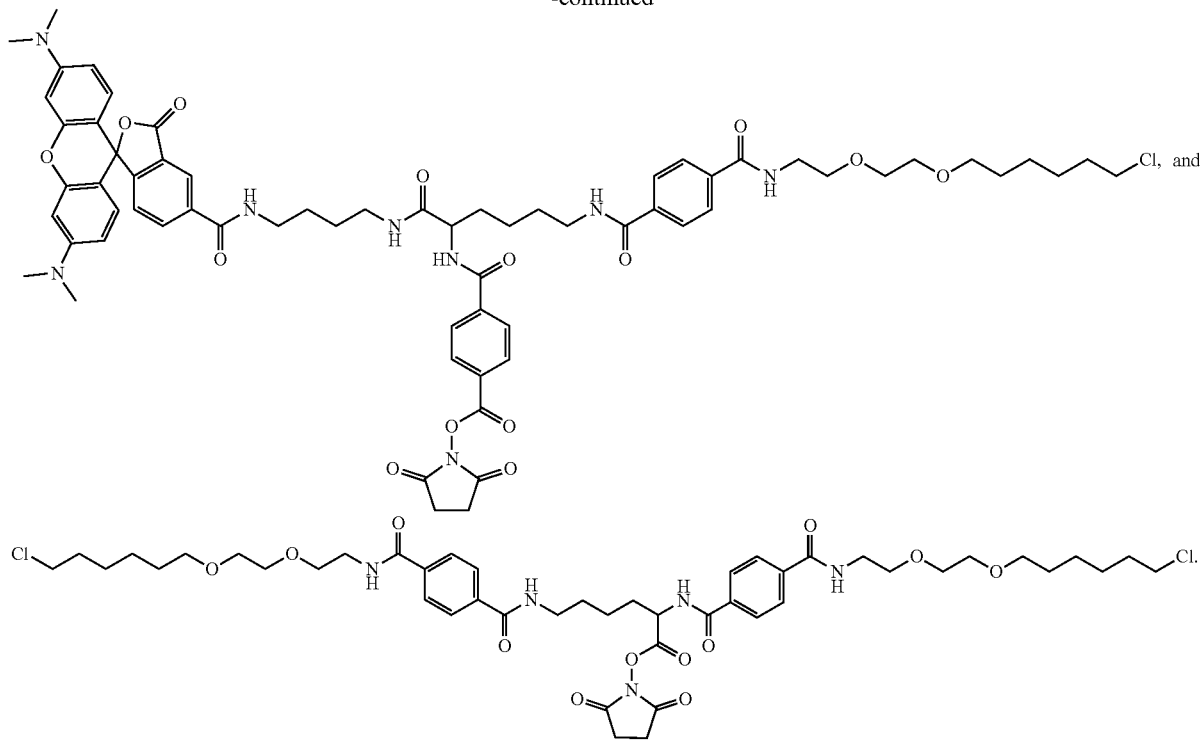

In some embodiments, the compound is cell impermeable.

In some embodiments, provided herein are methods of labeling a cell comprising contacting the cell with an effective amount of a multifunctional probe herein, wherein the biomolecule-reactive group forms a covalent bond with a cell-associated biomolecule on or within the cell, thereby labeling the cell.

In some embodiments, provided herein are cells labeled with an effective amount of a multifunctional probe herein. In some embodiments, the cell is derived from a carcinoma, a sarcoma, a leukemia, a lymphoma, a multiple myeloma, a melanoma, a brain or spinal cord tumor, a germ cell tumor, a neuroendocrine tumor, or a carcinoid tumor.

In some embodiments, provided herein are methods comprising: (a) contacting a cell with an effective amount of a probe comprising a multifunctional probe herein, wherein the biomolecule-reactive group forms a covalent bond with cell-associated biomolecules on or within the cell; (b) contacting the cell with a set of capture/detection reagents; wherein a first capture/detection reagent comprises: (i) one of a complementary peptide or a complementary polypeptide component of a bioluminescent complex, and (ii) a capture agent capable of stably binding to the capture element; wherein a second capture/detection reagent comprises: (i) the other of a complementary peptide or a complementary polypeptide component of a bioluminescent complex, and (ii) one of: a capture agent capable of stably binding to the capture element, or a binding agent capable of binding directly to cell-associated biomolecules on the cell; (c) contacting the cell with a substrate for the bioluminescent complex; and (d) monitoring and/or detecting bioluminescence. In some embodiments, methods further comprise a step of removing unincorporated probe from contact with the cell. In some embodiments, the unincorporated probe is removed from contact with the cell by washing the cell. In some embodiments, the unincorporated probe is removed from contact with the cell by centrifugation. In some embodiments, the unincorporated probe is removed from contact with the cell between steps (a) and (b). In some embodiments, methods further comprise placing the cell into a mixed cell population with unlabeled cells. In some embodiments, methods further comprise exposing the cell to a stimulus or condition. In some embodiments, stimulus or condition results in cell death and/or permeabilization of the cell. In some embodiments, the cell is exposed to the stimulus or condition between steps (a) and (b). In some embodiments, the cell is exposed to the stimulus or condition between steps (b) and (c). In some embodiments, the cell is exposed to the stimulus or condition between steps (c) and (d). In some embodiments, methods further comprise a step of allowing the capture/detection reagents to bind to the capture elements displayed on any biomolecules on or released from the cell and/or directly to cell-associated biomolecules on the cell, wherein binding of capture/detection reagents comprising complementary peptide and polypeptide components of the bioluminescent complex to adjacent capture elements and/or biomolecules will result in the formation of the bioluminescent complex. In some embodiments, the biomolecule-reactive group forms a covalent bond non-specifically with cell-associated biomolecules on or within the cell. In some embodiments, the probe is cell permeable and capable of labeling biomolecules within the cell. In some embodiments, the probe is cell impermeable and capable of labeling biomolecules on the cell surface.

In some embodiments, a first capture/detection reagent comprises: (i) a complementary polypeptide component of a bioluminescent complex and (ii) a capture agent capable of stably binding to the capture element; and wherein a second capture/detection reagent comprises: (i) a complementary peptide component of a bioluminescent complex and (ii) a capture agent capable of stably binding to the capture element.

In some embodiments, a first capture/detection reagent comprises: (i) a complementary polypeptide component of a bioluminescent complex and (ii) a capture agent capable of stably binding to the capture element; and wherein a second capture/detection reagent comprises: (i) the other of a complementary peptide or a complementary polypeptide component of a bioluminescent complex, and (ii) a binding agent capable of binding directly to cell-associated biomolecules on the cell. In some embodiments, the binding agent is an antibody or antibody fragment. In some embodiments, the binding agent is a biomolecule or small molecule. In some embodiments, the binding agent is Annexin V.

In some embodiments, a first capture/detection reagent comprises: (i) a complementary peptide or polypeptide component of a bioluminescent complex and (ii) a capture agent capable of stably binding to the capture element; and wherein a second capture/detection reagent comprises: (i) the other of a complementary peptide or a complementary polypeptide or peptide component of a bioluminescent complex, (ii) one of: a capture agent capable of stably binding to the capture element, a binding agent capable of binding directly to cell-associated biomolecules on the cell, and a fluorophore. In some embodiments, the capture element is a haloalkyl group and the capture agent is a modified dehalogenase enzyme capable of forming a covalent bond with a haloalkane substrate. In some embodiments, the biomolecule-reactive group is a succinimidyl ester capable of forming a covalent bond with amines on intracellular or extracellular proteins of the cell. In some embodiments, the probe is cell permeable. In some embodiments, the modified dehalogenase enzyme comprises at least 70% (e.g., 70%, 75%, 80%, 85%, 90%, 95%, 100%, or ranges therebetween) sequence identity with SEQ ID NO: 16. In some embodiments, the complementary peptide and polypeptide components collectively comprise a sequence having at least 70% (e.g., 70%, 75%, 80%, 85%, 90%, 95%, 100%, or ranges therebetween) sequence identity with SEQ ID NO: 17 and are capable of forming a facilitated bioluminescent complex upon being brought into contact with one another. In some embodiments, the complementary peptide component comprises a sequence having at least 70% (e.g., 70%, 75%, 80%, 85%, 90%, 95%, 100%, or ranges therebetween) sequence identity with SEQ ID NO: 10, and the complementary polypeptide component comprises a sequence having at least 70% (e.g., 70%, 75%, 80%, 85%, 90%, 95%, 100%, or ranges therebetween) sequence identity with SEQ ID NO: 9. In some embodiments, the complementary system includes two peptides and a polypeptide component, wherein one or more of the peptide and polypeptide components is not fused to a capture agent, and collectively comprise a sequence having at least 70% (e.g., 70%, 75%, 80%, 85%, 90%, 95%, 100%, or ranges therebetween) sequence identity with SEQ ID NO: 17 and are capable of forming a facilitated bioluminescent complex upon being brought into contact with one another through binding of the capture agents to the capture elements. In some embodiments, the complementary peptide and polypeptide components, along with one or more additional peptide and polypeptide components not fused to a capture agent, collectively comprise a sequence having at least 70% (e.g., 70%, 75%, 80%, 85%, 90%, 95%, 100%, or ranges therebetween) sequence identity with SEQ ID NO: 17 and are capable of forming a facilitated bioluminescent complex upon being brought into contact with one another through binding of the capture agents to the capture elements. In some embodiments, the complementary peptide component and the additional peptide component comprise sequences collectively having at least 70% (e.g., 70%, 75%, 80%, 85%, 90%, 95%, 100%, or ranges therebetween) sequence identity with SEQ ID NO: 14 and the complementary polypeptide component comprises a sequence having at least 70% (e.g., 70%, 75%, 80%, 85%, 90%, 95%, 100%, or ranges therebetween) sequence identity with SEQ ID NO: 12 or 19. In some embodiments, the complementary peptide component and the additional peptide component comprise sequences having at least 70% (e.g., 70%, 75%, 80%, 85%, 90%, 95%, 100%, or ranges therebetween) sequence identity with SEQ ID NOS: 11 and 13. In some embodiments, the peptide and polypeptide components will not efficiently form a bioluminescent complex in the absence of facilitation by being brought into contact with one another through binding of the capture agents to the capture elements. In some embodiments, efficient formation of a bioluminescent complex comprises a complex that produces more than a background level of bioluminescence. In some embodiments, the amount of bioluminescent complex formation (and detectable bioluminescent signal) is enhanced by bringing the peptide and polypeptide components into contact with one another through binding of the capture agents to the capture elements. In some embodiments, the bioluminescent complex exhibits significantly enhanced bioluminescence in the presence of a suitable substrate when compared to the bioluminescence of any of the individual peptide and polypeptide components, and to any pair of peptide and polypeptide components, in the presence of the suitable substrate. In some embodiments, the substrate for the bioluminescent complex is coelenterazine or a coelenterazine analog. In some embodiments, the stimulus or condition is a therapeutic, immunotherapeutic, or chemotherapeutic. In some embodiments, bioluminescence is monitored using a luminometer.

In some embodiments, provided herein are methods comprising: (a) contacting a cell with an effective amount of a probe comprising a multifunctional probe described herein, wherein the biomolecule-reactive group forms a covalent bond with cell-associated biomolecules on or within the cell; and (b) removing unincorporated probe from contact with the cell. In some embodiments, the unincorporated probe is removed from contact with the cell by washing the cell. In some embodiments, the unincorporated probe is removed from contact with the cell by centrifugation. In some embodiments, methods further comprise placing the cell into a mixed cell population with unlabeled cells. In some embodiments, methods further comprise: (c) contacting the cell with a set of capture/detection reagents; wherein a first capture/detection reagent comprises: (i) one of a complementary peptide or a complementary polypeptide component of a bioluminescent complex, and (ii) a capture agent capable of stably binding to the capture element; wherein a second capture/detection reagent comprises: (i) the other of a complementary peptide or a complementary polypeptide component of a bioluminescent complex, and (ii) one of: a capture agent capable of stably binding to the capture element, a binding agent capable of binding directly to cell-associated biomolecules on the cell; (d) contacting the cell with a substrate for the bioluminescent complex; and (e) monitoring and/or detecting bioluminescence. In some embodiments, methods further comprise exposing the cell to a stimulus or condition. In some embodiments, the stimulus or condition results in cell death and/or permeabilization of the cell. In some embodiments, methods further comprise a step of allowing the capture/detection reagents to bind to the capture elements displayed on any biomolecules on or released from the cell and/or directly to cell-associated biomolecules on the cell, wherein binding of capture/detection reagents comprising complementary peptide and polypeptide components of the bioluminescent complex to adjacent capture elements and/or biomolecules will result in the formation of the bioluminescent complex. In some embodiments, the biomolecule-reactive group forms a covalent bond non-specifically with cell-associated biomolecules on or within the cell. In some embodiments, the probe is cell permeable and capable of labeling biomolecules within the cell. In some embodiments, the probe is cell impermeable and capable of labeling biomolecules on the cell surface. In some embodiments, the capture element is a haloalkyl group, and the capture agent is a modified dehalogenase enzyme capable of forming a covalent bond with a haloalkane substrate. In some embodiments, the biomolecule-reactive group is a succinimidyl ester capable of forming a covalent bond with amines on intracellular or extracellular proteins of the cell. In some embodiments, the biomolecule-reactive group is a maleimide capable of forming a covalent bond with thiols on intracellular or extracellular proteins of the cell. In some embodiments, the probe is cell permeable. In some embodiments, the modified dehalogenase enzyme comprises at least 70% (e.g., 70%, 75%, 80%, 85%, 90%, 95%, 100%, or ranges therebetween) sequence identity with SEQ ID NO: 16. In some embodiments, the complementary peptide and polypeptide components collectively comprise a sequence having at least 70% (e.g., 70%, 75%, 80%, 85%, 90%, 95%, 100%, or ranges therebetween) sequence identity with SEQ ID NO: 17 and are capable of forming a facilitated bioluminescent complex upon being brought into contact with one another. In some embodiments, the complementary peptide component comprises a sequence having at least 70% (e.g., 70%, 75%, 80%, 85%, 90%, 95%, 100%, or ranges therebetween) sequence identity with SEQ ID NO: 10, and the complementary polypeptide component comprises a sequence having at least 70% (e.g., 70%, 75%, 80%, 85%, 90%, 95%, 100%, or ranges therebetween) sequence identity with SEQ ID NO: 9. In some embodiments, the complementary system includes two peptides and a polypeptide component, wherein one or more of the peptide and polypeptide components is not fused to a capture agent, and collectively comprise a sequence having at least 70% (e.g., 70%, 75%, 80%, 85%, 90%, 95%, 100%, or ranges therebetween) sequence identity with SEQ ID NO: 17 and are capable of forming a facilitated bioluminescent complex upon being brought into contact with one another through binding of the capture agents to the capture elements. In some embodiments, the complementary peptide and polypeptide components, along with one or more additional peptide and polypeptide components not fused to a capture agent, collectively comprise a sequence having at least 70% (e.g., 70%, 75%, 80%, 85%, 90%, 95%, 100%, or ranges therebetween) sequence identity with SEQ ID NO: 17 and are capable of forming a facilitated bioluminescent complex upon being brought into contact with one another through binding of the capture agents to the capture elements. In some embodiments, the complementary peptide component and the additional peptide component comprise sequences collectively having at least 70% (e.g., 70%, 75%, 80%, 85%, 90%, 95%, 100%, or ranges therebetween) sequence identity with SEQ ID NO: 14, and the complementary polypeptide component comprises a sequence having at least 70% (e.g., 70%, 75%, 80%, 85%, 90%, 95%, 100%, or ranges therebetween) sequence identity with SEQ ID NO: 12 or 19. In some embodiments, the complementary peptide component and the additional peptide component comprise sequences having at least 70% (e.g., 70%, 75%, 80%, 85%, 90%, 95%, 100%, or ranges therebetween) sequence identity with SEQ ID NOS: 11 and 13. In some embodiments, the peptide and polypeptide components will not efficiently form a bioluminescent complex in the absence of facilitation by being brought into contact with one another through binding of the capture agents to the capture elements. In some embodiments, efficient formation of a bioluminescent complex comprises a complex that produces more than a background level of bioluminescence. In some embodiments, the amount of bioluminescent complex formation (and detectable bioluminescent signal) is enhanced by bringing the peptide and polypeptide components into contact with one another through binding of the capture agents to the capture elements. In some embodiments, the bioluminescent complex exhibits significantly enhanced bioluminescence in the presence of a suitable substrate when compared to the bioluminescence of any of the individual peptide and polypeptide components, and to any pair of peptide and polypeptide components, in the presence of the suitable substrate. In some embodiments, the substrate for the bioluminescent complex is coelenterazine or a coelenterazine analog. In some embodiments, the stimulus or condition is a therapeutic, immunotherapeutic, or chemotherapeutic. In some embodiments, bioluminescence is monitored using a luminometer.

In some embodiments, provided herein are methods comprising: (a) contacting a cell with an effective amount of a probe comprising a multifunctional probe described herein, wherein the biomolecule-reactive group forms a covalent bond with cell-associated biomolecules on or within the cell; (b) contacting the cell with a first capture/detection reagent comprising (i) a complementary polypeptide component of a bioluminescent complex and (ii) a capture agent capable of stably binding to the capture element; (c) contacting the cell with a second capture/detection reagent comprising (i) a complementary peptide component of a bioluminescent complex and (ii) a capture agent capable of stably binding to the capture element; wherein the polypeptide component and the peptide component are capable of forming a bioluminescent complex when brought into proximity of each other; (d) contacting the cell with a substrate for the bioluminescent complex; and (e) monitoring and/or detecting bioluminescence. In some embodiments, methods further comprise removing unincorporated probe from contact with the cell. In some embodiments, the unincorporated probe is removed from contact with the cell by washing the cell. In some embodiments, the unincorporated probe is removed from contact with the cell by centrifugation. In some embodiments, the unincorporated probe is removed from contact with the cell between steps (a) and (b). In some embodiments, methods further comprise placing the cell into a mixed cell population with unlabeled cells. In some embodiments, methods further comprise exposing the cell to a stimulus or condition. In some embodiments, the stimulus or condition results in cell death and/or permeabilization of the cell. In some embodiments, the cell is exposed to the stimulus or condition between steps (a) and (b). In some embodiments, the cell is exposed to the stimulus or condition between steps (c) and (d). In some embodiments, the cell is exposed to the stimulus or condition between steps (d) and (e). In some embodiments, cell death and/or permeabilization of the cell results in exposure and/or release of the biomolecules from the cell. In some embodiments, binding of capture/detection reagents comprising complementary peptide and polypeptide components of the bioluminescent complex to adjacent capture elements and/or biomolecules will result in the formation of the bioluminescent complex.

In some embodiments, the biomolecule-reactive group forms a covalent bond non-specifically with cell-associated biomolecules on or within the cell. In some embodiments, the probe is cell permeable and capable of labeling biomolecules within the cell. In some embodiments, the probe is cell impermeable and capable of labeling biomolecules on the cell surface. In some embodiments, the capture element is a haloalkyl group, and the capture agent is a modified dehalogenase enzyme capable of forming a covalent bond with a haloalkane substrate. In some embodiments, the biomolecule-reactive group is a succinimidyl ester capable of forming a covalent bond with amines on intracellular or extracellular biomolecules (e.g., proteins) of the cell. In some embodiments, the biomolecule-reactive group is a maleimide capable of forming a covalent bond with thiols on intracellular or extracellular biomolecules (e.g., proteins) of the cell. In some embodiments, the modified dehalogenase enzyme comprises at least 70% (e.g., 70%, 75%, 80%, 85%, 90%, 95%, 100%, or ranges therebetween) sequence identity with SEQ ID NO: 16. In some embodiments, the complementary peptide and polypeptide components collectively comprise a sequence having at least 70% (e.g., 70%, 75%, 80%, 85%, 90%, 95%, 100%, or ranges therebetween) sequence identity with SEQ ID NO: 17 and are capable of forming a facilitated bioluminescent complex upon being brought into contact with one another. In some embodiments, the complementary peptide component comprises a sequence having at least 70% (e.g., 70%, 75%, 80%, 85%, 90%, 95%, 100%, or ranges therebetween) sequence identity with SEQ ID NO: 10, and the complementary polypeptide component comprises a sequence having at least 70% (e.g., 70%, 75%, 80%, 85%, 90%, 95%, 100%, or ranges therebetween) sequence identity with SEQ ID NO: 9. In some embodiments, the complementary system includes two peptides and a polypeptide component, wherein one or more of the peptide and polypeptide components is not fused to a capture agent, and collectively comprise a sequence having at least 70% (e.g., 70%, 75%, 80%, 85%, 90%, 95%, 100%, or ranges therebetween) sequence identity with SEQ ID NO: 17 and are capable of forming a facilitated bioluminescent complex upon being brought into contact with one another through binding of the capture agents to the capture elements. In some embodiments, the complementary peptide and polypeptide components, along with one or more additional peptide and polypeptide components not fused to a capture agent, collectively comprise a sequence having at least 70% (e.g., 70%, 75%, 80%, 85%, 90%, 95%, 100%, or ranges therebetween) sequence identity with SEQ ID NO: 17 and are capable of forming a facilitated bioluminescent complex upon being brought into contact with one another through binding of the capture agents to the capture elements. In some embodiments, the complementary peptide component and the additional peptide component comprise sequences collectively having at least 70% (e.g., 70%, 75%, 80%, 85%, 90%, 95%, 100%, or ranges therebetween) sequence identity with SEQ ID NO: 14, and the complementary polypeptide component comprises a sequence having at least 70% (e.g., 70%, 75%, 80%, 85%, 90%, 95%, 100%, or ranges therebetween) sequence identity with SEQ ID NO: 12 or 19. In some embodiments, the complementary peptide component and the additional peptide component comprise sequences having at least 70% (e.g., 70%, 75%, 80%, 85%, 90%, 95%, 100%, or ranges therebetween) sequence identity with SEQ ID NOS: 11 and 13.

In some embodiments, provided herein are methods comprising: (a) contacting a cell with an effective amount of a probe comprising a multifunctional probe described herein, wherein the biomolecule-reactive group forms a covalent bond with cell-associated biomolecules on or within the cell; (b) contacting the cell with a first capture/detection reagent comprising (i) a complementary polypeptide or a peptide component of a bioluminescent complex and (ii) a capture agent capable of stably binding to the capture element; (c) contacting the cell with a second non-covalent binding/detection reagent comprising (i) a complementary peptide or polypeptide component of a bioluminescent complex and (ii) a binding agent capable of directly binding to a biomolecule on the cell; wherein the polypeptide component and the peptide component are capable of forming a bioluminescent complex when brought into proximity of each other; (d) contacting the cell with a substrate for the bioluminescent complex; and (e) monitoring and/or detecting bioluminescence. In some embodiments, methods further comprise removing unincorporated probe from contact with the cell. In some embodiments, the unincorporated probe is removed from contact with the cell by washing the cell. In some embodiments, the unincorporated probe is removed from contact with the cell by centrifugation. In some embodiments, the unincorporated probe is removed from contact with the cell between steps (a) and (b). In some embodiments, methods further comprise placing the cell into a mixed cell population with unlabeled cells. In some embodiments, methods further comprise exposing the cell to a stimulus or condition. In some embodiments, the stimulus or condition results in cell death and/or permeabilization of the cell. In some embodiments, the cell is exposed to the stimulus or condition between steps (a) and (b). In some embodiments, the cell is exposed to the stimulus or condition between steps (c) and (d). In some embodiments, the cell is exposed to the stimulus or condition between steps (d) and (e). In some embodiments, cell death and/or permeabilization of the cell results in exposure and/or release of the biomolecules from the cell. In some embodiments, binding of capture/detection reagents and non-covalent binding/detection moiety comprising complementary peptide and polypeptide components of the bioluminescent complex to adjacent capture elements and/or biomolecules will result in the formation of the bioluminescent complex. In some embodiments, the biomolecule-reactive group forms a covalent bond non-specifically with cell-associated biomolecules on or within the cell. In some embodiments, the probe is cell permeable and capable of labeling biomolecules within the cell. In some embodiments, the probe is cell impermeable and capable of labeling biomolecules on the cell surface. In some embodiments, the binding agent is an antibody or antibody fragment. In some embodiments, the binding agent is a biomolecule or small molecule. In some embodiments, the binding agent is Annexin V. In some embodiments, the capture element is a haloalkyl group, and the capture agent is a modified dehalogenase enzyme capable of forming a covalent bond with a haloalkane substrate. In some embodiments, the biomolecule-reactive group is a succinimidyl ester capable of forming a covalent bond with amines on intracellular or extracellular proteins of the cell. In some embodiments, the biomolecule-reactive group is a maleimide capable of forming a covalent bond with thiols on intracellular or extracellular proteins of the cell. In some embodiments, the modified dehalogenase enzyme comprises at least 70% (e.g., 70%, 75%, 80%, 85%, 90%, 95%, 100%, or ranges therebetween) sequence identity with SEQ ID NO: 16. In some embodiments, the complementary peptide and polypeptide components collectively comprise a sequence having at least 70% (e.g., 70%, 75%, 80%, 85%, 90%, 95%, 100%, or ranges therebetween) sequence identity with SEQ ID NO: 17 and are capable of forming a facilitated bioluminescent complex upon being brought into contact with one another. In some embodiments, the complementary peptide component comprises a sequence having at least 70% (e.g., 70%, 75%, 80%, 85%, 90%, 95%, 100%, or ranges therebetween) sequence identity with SEQ ID NO: 10, and the complementary polypeptide component comprises a sequence having at least 70% (e.g., 70%, 75%, 80%, 85%, 90%, 95%, 100%, or ranges therebetween) sequence identity with SEQ ID NO: 9. In some embodiments, the complementary system includes two peptides and a polypeptide component, wherein one or more of the peptide and polypeptide components are not fused to a capture agent, and collectively comprise a sequence having at least 70% (e.g., 70%, 75%, 80%, 85%, 90%, 95%, 100%, or ranges therebetween) sequence identity with SEQ ID NO: 17 and are capable of forming a facilitated bioluminescent complex upon being brought into contact with one another through binding of the capture agents to the capture elements. In some embodiments, the complementary peptide and polypeptide components one or more additional peptide and polypeptide components not fused to a capture agent, collectively comprise a sequence having at least 70% (e.g., 70%, 75%, 80%, 85%, 90%, 95%, 100%, or ranges therebetween) sequence identity with SEQ ID NO: 17 and are capable of forming a facilitated bioluminescent complex upon being brought into contact with one another through binding of the capture agents to the capture elements. In some embodiments, the complementary peptide component and the additional peptide component comprise sequences collectively having at least 70% (e.g., 70%, 75%, 80%, 85%, 90%, 95%, 100%, or ranges therebetween) sequence identity with SEQ ID NO: 14, and the complementary polypeptide component comprises a sequence having at least 70% (e.g., 70%, 75%, 80%, 85%, 90%, 95%, 100%, or ranges therebetween) sequence identity with SEQ ID NO: 12 or 19. In some embodiments, the complementary peptide component and the additional peptide component comprise sequences having at least 70% (e.g., 70%, 75%, 80%, 85%, 90%, 95%, 100%, or ranges therebetween) sequence identity with SEQ ID NOS: 11 and 13.

In some embodiments, provided herein are methods comprising: (a) contacting a cell population with an effective amount of a probe comprising a multifunctional probe described herein, wherein the biomolecule-reactive group forms a covalent bond with cell-associated biomolecules on or within the cells; (b) removing unincorporated probe and dead cells from the population of labelled live cells; (c) fixing and permeabilizing the population of labelled live cells; (d) contacting the fixed and permeabilized cell population with a first capture/detection reagent comprising: (i) a complementary polypeptide component of a bioluminescent complex and (ii) a capture agent capable of stably binding to the capture element; (e) contacting the fixed and permeabilized cell population with a second capture/detection reagent comprising: (i) a complementary peptide component of a bioluminescent complex, and (ii) a fluorophore; wherein the polypeptide component and the peptide component are capable of forming a bioluminescent complex; and (f) detecting luminescence and/or fluorescence. In some embodiments, luminescence and/or fluorescence is detected by fluorescent imaging, flow cytometry, and/or luminescent measurement. In some embodiments, the capture element is a haloalkyl group, and the capture agent is a modified dehalogenase enzyme capable of forming a covalent bond with a haloalkane substrate. In some embodiments, the biomolecule-reactive group is a succinimidyl ester capable of forming a covalent bond with amines on intracellular or extracellular proteins of the cell. In some embodiments, the modified dehalogenase enzyme comprises at least 70% (e.g., 70%, 75%, 80%, 85%, 90%, 95%, 100%, or ranges therebetween) sequence identity with SEQ ID NO: 16. In some embodiments, the complementary peptide and polypeptide components collectively comprise a sequence having at least 70% (e.g., 70%, 75%, 80%, 85%, 90%, 95%, 100%, or ranges therebetween) sequence identity with SEQ ID NO: 17 and are capable of forming a facilitated bioluminescent complex upon being brought into contact with one another. In some embodiments, the complementary peptide component comprises a sequence having at least 70% (e.g., 70%, 75%, 80%, 85%, 90%, 95%, 100%, or ranges therebetween) sequence identity with SEQ ID NO: 11, and the complementary polypeptide component comprises a sequence having at least 70% (e.g., 70%, 75%, 80%, 85%, 90%, 95%, 100%, or ranges therebetween) sequence identity with SEQ ID NO: 9.

In some embodiments, provided herein are kits comprising a multifunctional probe comprising a multifunctional probe described herein and a set of capture/detection reagents, each capture/detection reagent comprising a fusion of (i) a capture agent capable of stably binding to the capture element and (ii) a complementary peptide or polypeptide component of a bioluminescent complex. In some embodiments, the complementary peptide and polypeptide components collectively comprise 70% or greater (e.g., 70%, 75%, 80%, 85%, 90%, 95%, 100%, or ranges therebetween) sequence identity with a sequence of SEQ ID NO: 17. In some embodiments, a first capture/detection reagent comprises a complementary peptide comprising 70% or greater (e.g., 70%, 75%, 80%, 85%, 90%, 95%, 100%, or ranges therebetween) sequence identity to SEQ ID NO: 11, and a second capture/detection reagent comprises a complementary peptide comprising 70% or greater (e.g., 70%, 75%, 80%, 85%, 90%, 95%, 100%, or ranges therebetween) sequence identity with SEQ ID NO: 13. In some embodiments, kits further comprise a complementary polypeptide comprising 70% or greater (e.g., 70%, 75%, 80%, 85%, 90%, 95%, 100%, or ranges therebetween) sequence identity with SEQ ID NO: 12 or 19. In some embodiments, the capture agent comprises 70% or greater (e.g., 70%, 75%, 80%, 85%, 90%, 95%, 100%, or ranges therebetween) sequence identity to SEQ ID NO: 16. In some embodiments, kits further comprise a coelenterazine substrate or coelenterazine analog substrate.

In some embodiments, provided herein are kits comprising: (a) a first capture/detection reagent comprising a fusion of (i) a capture agent capable of stably binding to the capture element, and (ii) a peptide component capable of forming a bioluminescent complex with a complementary polypeptide component; and (b) a second capture/detection reagent comprising a fusion of (i) a capture agent capable of stably binding to the capture element, and (ii) the polypeptide component capable of forming a bioluminescent complex with the peptide component. In some embodiments, the capture agent comprises 70% or greater (e.g., 70%, 75%, 80%, 85%, 90%, 95%, 100%, or ranges therebetween) sequence identity to SEQ ID NO: 16. In some embodiments, the peptide component and complementary polypeptide component collectively comprise 70% or greater (e.g., 70%, 75%, 80%, 85%, 90%, 95%, 100%, or ranges therebetween) sequence identity with a sequence of SEQ ID NO: 17. In some embodiments, kits further comprise a coelenterazine substrate or coelenterazine analog substrate. In some embodiments, the peptide comprises 70% or greater (e.g., 70%, 75%, 80%, 85%, 90%, 95%, 100%, or ranges therebetween) sequence identity to SEQ ID NO: 10, and the complementary polypeptide comprises 70% or greater (e.g., 70%, 75%, 80%, 85%, 90%, 95%, 100%, or ranges therebetween) sequence identity with SEQ ID NO: 9.

In some embodiments, provided herein are kits comprising: (a) a first capture/detection reagent comprising a fusion of (i) a capture agent capable of stably binding to the capture element, and (ii) a first peptide component capable of forming a bioluminescent complex with complementary peptide and polypeptide components; and (b) a second capture/detection reagent comprising a fusion of (i) a capture agent capable of stably binding to the capture element, and (ii) a second peptide component capable of forming a bioluminescent complex with complementary peptide and polypeptide components; wherein the first peptide component and second peptide component collectively comprise at least 70% (e.g., 70%, 75%, 80%, 85%, 90%, 95%, 100%, or ranges therebetween) sequence identity with SEQ ID NO: 14, and the polypeptide component comprises at least 70% (e.g., 70%, 75%, 80%, 85%, 90%, 95%, 100%, or ranges therebetween) sequence identity with SEQ ID NO: 12 or 19. In some embodiments, the capture agent comprises 70% or greater (e.g., 70%, 75%, 80%, 85%, 90%, 95%, 100%, or ranges therebetween) sequence identity to SEQ ID NO: 16.

In some embodiments, provided herein are methods comprising: (a) contacting a cell with an effective amount of a probe comprising a compound of claim 21, wherein the biomolecule-reactive group forms a covalent bond with biomolecules on the surface of the cell; (b) contacting the cell with a first capture/detection reagent comprising (i) a capture agent capable of stably binding to the capture element, and (ii) a first complementary peptide or polypeptide component of a bioluminescent complex; (c) contacting the cell with a second capture/detection reagent comprising (i) a second biomolecule-reactive group capable of stably binding to a second biomolecule, and (ii) a second complementary peptide or polypeptide component of the bioluminescent complex; (d) contacting the cell with a substrate for the bioluminescent complex; (e) exposing the cell to a stimulus or condition; (f) allowing the capture/detection reagents to bind to the capture element and second biomolecule, respectively, wherein binding of capture/detection reagents at adjacent positions will result in the formation of the bioluminescent complex; and (g) monitoring and/or detecting bioluminescence, in the presence of a bioluminescence substrate, wherein the amount of bioluminescence is proportional to the amount of biomolecules on the outer surface of the cell. In some embodiments, provided herein are methods comprising: (a) contacting a cell with an effective amount of a probe comprising a compound of claim 21, wherein the biomolecule-reactive group forms a covalent bond with biomolecules on the surface of the cell; (b) washing the cell to remove unbound probe from the cell; (c) contacting the cell with a first capture/detection reagent comprising (i) a capture agent capable of stably binding to the capture element, and (ii) a first complementary peptide or polypeptide component of a bioluminescent complex; (d) contacting the cell with a second capture/detection reagent comprising (i) a second biomolecule-reactive/binding group or capable of stably binding to a second biomolecule, and (ii) and a second complementary peptide or polypeptide component of the bioluminescent complex; (e) exposing the cell to a stimulus or condition; (f) contacting the cell with a substrate for the bioluminescent complex; (g) allowing the capture/detection reagents to bind to the capture element and second biomolecule, respectively, wherein binding of capture/detection reagents at adjacent positions will result in the formation of the bioluminescent complex; and (h) monitoring and/or detecting bioluminescence, in the presence of a bioluminescence substrate. In some embodiments, the capture element is a haloalkyl group, and the capture agent is a modified dehalogenase enzyme capable of forming a covalent bond with a haloalkane substrate. In some embodiments, the biomolecule-reactive group is a succinimidyl ester capable of forming a covalent bond with amines on extracellular biomolecules of the cell. In some embodiments, the biomolecule-reactive group is a maleimide capable of forming a covalent bond with thiols on extracellular biomolecules of the cell. In some embodiments, the modified dehalogenase enzyme comprises at least 70% (e.g., 70%, 75%, 80%, 85%, 90%, 95%, 100%, or ranges therebetween) sequence identity with SEQ ID NO: 16. In some embodiments, the complementary peptide and polypeptide components collectively comprise a sequence having at least 70% (e.g., 70%, 75%, 80%, 85%, 90%, 95%, 100%, or ranges therebetween) sequence identity with SEQ ID NO: 17 and are capable of forming a facilitated bioluminescent complex upon being brought into contact with one another. In some embodiments, the complementary system includes two peptides and a polypeptide component, wherein one or more of the peptide and polypeptide components are not fused to a capture agent, and collectively comprise a sequence having at least 70% (e.g., 70%, 75%, 80%, 85%, 90%, 95%, 100%, or ranges therebetween) sequence identity with SEQ ID NO: 17, and are capable of forming a facilitated bioluminescent complex upon being brought into contact with one another through binding of the capture agents to the capture elements. In some embodiments, the complementary peptide and polypeptide components, along with one or more additional peptide and polypeptide components not fused to a capture agent, collectively comprise a sequence having at least 70% (e.g., 70%, 75%, 80%, 85%, 90%, 95%, 100%, or ranges therebetween) sequence identity with SEQ ID NO: 17 and are capable of forming a facilitated bioluminescent complex upon being brought into contact with one another through binding of the capture agents to the capture elements. In some embodiments, the complementary peptide and polypeptide components, along with one or more additional peptide or polypeptide components fused to additional capture agents, collectively comprise a sequence having at least 70% (e.g., 70%, 75%, 80%, 85%, 90%, 95%, 100%, or ranges therebetween) sequence identity with SEQ ID NO: 17 and are capable of forming a facilitated bioluminescent complex upon being brought into contact with one another through binding of the capture agents to the capture elements. In some embodiments, the peptide and polypeptide components will not efficiently form a bioluminescent complex in the absence of facilitation by being brought into contact with one another through binding of the capture agents to the capture elements. In some embodiments, efficient formation of a bioluminescent complex comprises a complex that produces more than a background level of bioluminescence. In some embodiments, the amount of bioluminescent complex formation (and detectable bioluminescent signal) is enhanced by bringing the peptide and polypeptide components into contact with one another through binding of the capture agents to the capture elements. In some embodiments, the bioluminescent complex exhibits significantly enhanced bioluminescence in the presence of a suitable substrate when compared to the bioluminescence of any combination of the peptide and polypeptide components in the presence of the suitable substrate. In some embodiments, the substrate for the bioluminescent complex is coelenterazine or a coelenterazine analog. In some embodiments, the stimulus or condition results in release of the second biomolecule from the cell. In some embodiments, the stimulus or condition results in cell death, membrane permeabilization, active transport mechanisms, an immune response, facilitated diffusion, secretion from the cell, or release in a vesicle. In some embodiments, wherein bioluminescence is monitored using a luminometer.

In some embodiments, provided herein are methods comprising: (a) contacting a cell with an effective amount of a probe comprising a multifunctional probe described herein, wherein the biomolecule-reactive group forms a covalent bond with a cell-associated biomolecule on or within the cell; (b) contacting the cell with a capture/detection reagent comprising a capture agent capable of stably binding to the capture element, and a complementary peptide or polypeptide component of a bioluminescent complex; (c) contacting the cell with a detection reagent comprising a fluorophore tethered to the other of the complementary peptide and polypeptide components of a bioluminescent complex; (d) contacting the cell with a substrate for the bioluminescent complex; (e) allowing the capture/detection reagent to bind to the capture elements and allowing the detection reagent to form a bioluminescent complex with the capture/detection reagent; (f) monitoring and/or detecting fluorescence from the fluorophore and/or bioluminescence, in the presence of a bioluminescence substrate, from the bioluminescent complex. In some embodiments, the complementary peptide comprises at least 70% (e.g., 70%, 75%, 80%, 85%, 90%, 95%, 100%, or ranges therebetween) sequence identity with SEQ ID NO: 11, and the complementary polypeptide comprises at least 70% (e.g., 70%, 75%, 80%, 85%, 90%, 95%, 100%, or ranges therebetween) sequence identity with SEQ ID NO: 9. In some embodiments, methods further comprise exposing the cell to a stimulus or condition that may result in cell death.

In some embodiments, provided herein are kits comprising: (a) a multifunctional probe comprising a biomolecule-reactive group linked to a capture element; (b) a first capture agent fused to a polypeptide component of a bioluminescent complex; (c) a second capture agent or a biomolecule binding agent fused to a peptide component of a bioluminescent complex; and (d) a substrate for the bioluminescent complex; wherein the peptide and polypeptide components form the bioluminescent complex when brought into proper proximity/orientation with one another by binding of the capture agents to adjacent capture elements; and wherein the bioluminescent complex produces luminescence in the presence of the substrate.

In some embodiments, provided herein are methods comprising contacting a cell or a sample comprising a cell with the components of a kit described herein.

In some embodiments, provided herein are kits comprising: (a) a multifunctional probe comprising a biomolecule-reactive group linked to a capture element; (b) a first capture agent fused to a polypeptide component of a bioluminescent complex; (c) a fluorophore tethered to a peptide component of a bioluminescent complex; and (d) a substrate for the bioluminescent complex; wherein the peptide and polypeptide components form the bioluminescent complex when co-localized with one another without external facilitation; and wherein the bioluminescent complex produces luminescence in the presence of the substrate. In some embodiments, the peptide component comprises at least 70% (e.g., 70%, 75%, 80%, 85%, 90%, 95%, 100%, or ranges therebetween) sequence identity with SEQ ID NO: 11, and the polypeptide component comprises at least 70% (e.g., 70%, 75%, 80%, 85%, 90%, 95%, 100%, or ranges therebetween) sequence identity with SEQ ID NO: 9.

In some embodiments, provided herein are kits comprising: (a) a multifunctional probe comprising a biomolecule-reactive group linked to a capture element; (b) a first capture agent fused to a polypeptide or peptide component of a bioluminescent complex; (c) a target-specific binding agent fused to the other of the polypeptide or peptide component of a bioluminescent complex; and (d) a substrate for the bioluminescent complex; wherein the peptide and polypeptide components form the bioluminescent complex when brought into proper proximity/orientation with one another by binding of the capture agent and target-specific binding agent to adjacent capture element and target; and wherein the bioluminescent complex produces luminescence in the presence of the substrate.

In some embodiments, provided herein are kits comprising: (a) a multifunctional probe comprising a biomolecule-reactive group linked to a capture element; (b) a first capture agent fused to a first peptide component of a bioluminescent complex; (c) a second capture agent fused to a second peptide component of a bioluminescent complex; (d) a polypeptide component of a bioluminescent complex; and (e) a substrate for the bioluminescent complex; wherein the peptide and polypeptide components form the bioluminescent complex when the peptide components are brought into proper proximity/orientation with one another by binding of the capture agents to adjacent capture elements; and wherein the bioluminescent complex produces luminescence in the presence of the substrate.

BRIEF DESCRIPTION OF THE DRAWINGS

The patent or application file contains at least one drawing executed in color. Copies of this patent or patent application publication with color drawings will be provided by the Office upon request and payment of the necessary fee.

FIGS. 1A-1C include representative schematic diagrams of cell-based assays that can be performed using the multifunctional probes described herein. (A) Cells are covalently labeled with a cell permeable or impermeable bifunctional probe that contains, for example, a succinimidyl ester group for covalent labeling of multiple cellular targets (biomolecules) and a chloroalkane ligand (for covalent binding to a HALOTAG protein). Note: The plasma membrane proteins represent <5% of total cellular proteins, therefore most of a cell permeable probe is incorporated into intracellular targets. The unincorporated free probes are removed by discarding supernatant after collecting cells by centrifugation. When labeled cells are pre-mixed with unlabeled cells, the fate of labeled cells can be specifically monitored, for example, by measuring the release of labeled biomolecules upon cell death or by detecting the amount of remaining labeled live cells in the sample. For example, in a mixture of labeled tumor cells and unlabeled natural killer cells, NK-mediated tumor cell death is monitored. (B) Detection of labeled targets upon cell death (1) HALOTAG-LgBiT and HALOTAG-SmBiT bind to exposed chloroalkane ligand on labeled targets. When two complementing BiT partners are within proximity a luminescent signal is generated. (2) HALOTAG-LgBiT binds to exposed chloroalkane ligands on labeled biomolecules. When a SmBiT-labeled binding moiety (e.g. an antibody or other binding partner of a biomolecule) to a specific cellular biomolecule (e.g. a protein) binds directly to that biomolecule in close proximity to HALOTAG-LgBiT, a luminescent signal is generated in the presence of a luminogenic substrate (e.g. furimazine). (3) A specific example of 1B(2) where HALOTAG-LgBiT binds to exposed chloroalkane ligands on labeled biomolecules. In this case the SmBiT-labeled binding moiety is Annexin V-SmBiT, which binds noncovalently to the exposed biomolecule, phosphatidylserine (PS), at the plasma membrane. When HALOTAG-LgBiT labeled targets are in close proximity to Annexin-V-SmBiT bound PS, a luminescent signal is generated with a luminogenic substrate.

FIGS. 3A-3C shows representative results of experiments conducted to test antibody dependent cellular cytotoxicity (ADCC) in Daudi (FIGS. 3A-3B), and SKBR3 (FIG. 3C) cells labeled with multifunctional probes and detected using bioluminescent detection components.

DETAILED DESCRIPTION

Figure 1A:
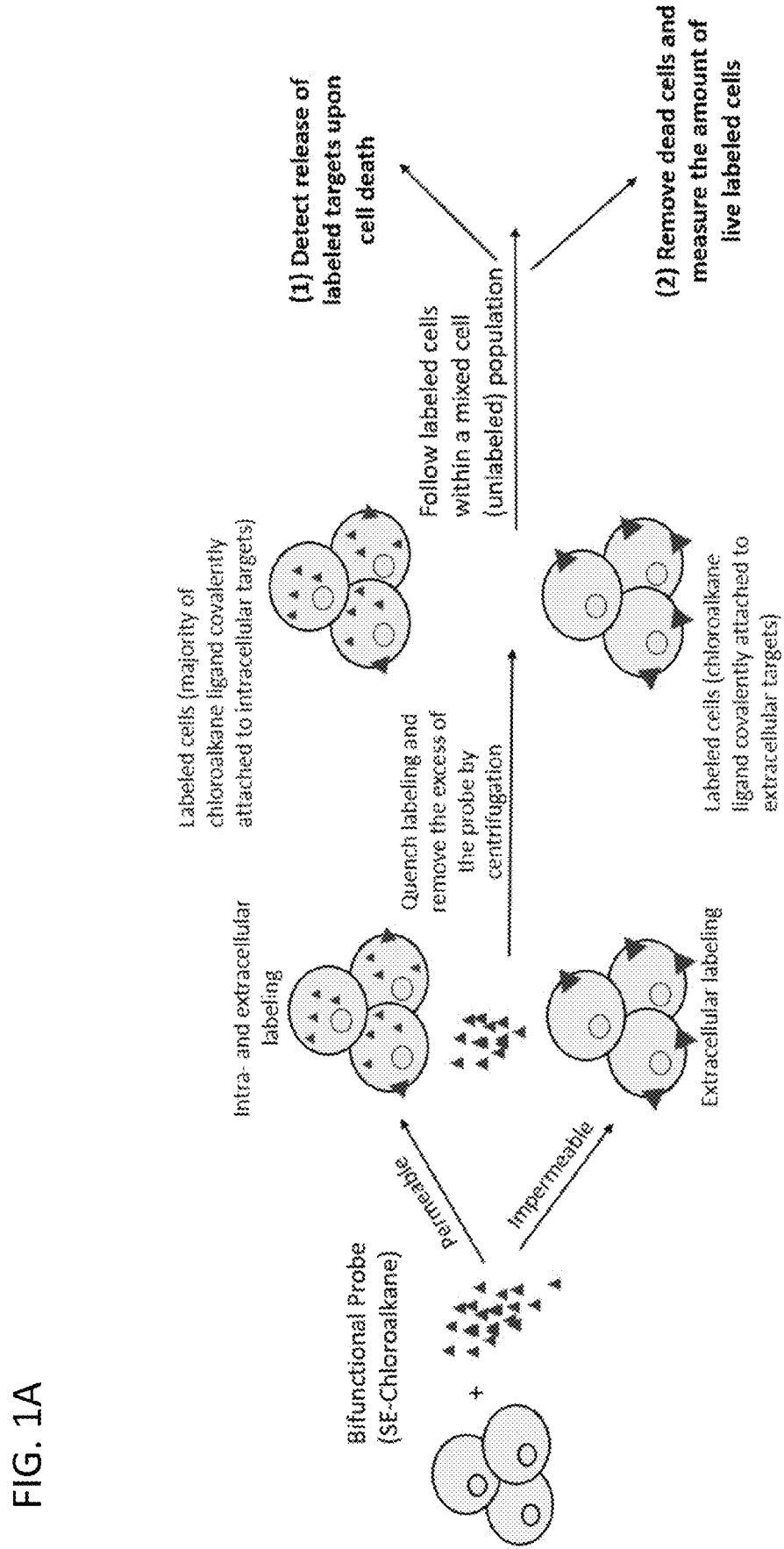
Figure 1C:
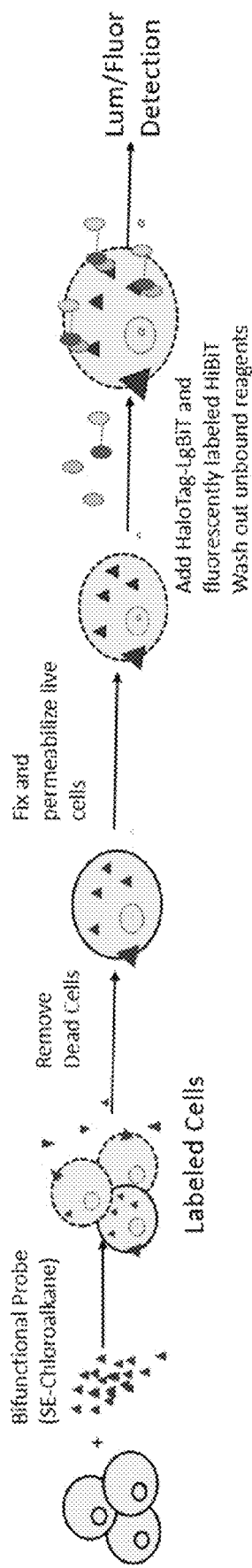

Embodiments of the present disclosure provide materials and methods for performing bioluminescent assays using a multifunctional (e.g., bifunctional, trifunctional, etc.) probe. In particular, the present disclosure provides compositions and methods for detecting and/or quantifying a biomolecule and/or assaying a cellular process associated with the biomolecule using a multifunctional (e.g., bifunctional, trifunctional, etc.) probe capable of binding the biomolecule and generating a bioluminescent and/or fluorescent signal.

The inventive subject matter of the present disclosure addresses the unmet need of providing bioassays, systems, and methods of detecting the responses of specific (e.g., pre-labeled) cell populations, particularly in co-cultured systems containing other unlabeled cells. The assays, systems, and methods of the present disclosure facilitate the measurement and/or quantification of cellular processes/responses (and/or biomolecules associated with a cellular process), particularly within a mixed population of cells. Currently, there are no bioassays available that use cell permeable, multifunctional probes to covalently label intracellular proteins in live cells and then detect their release (e.g., by using NanoLuc® Binary Technology (NanoBiT®), NanoTrip™ Technology, HaloTag® Technology, etc.). Features of the assays, systems, and methods of the present disclosure include, but are not limited to: universality and applicability to multiple cell types; the ability to quantitate changes using standard plate-readers in real time; and adaptability to miniaturization and automation due to the ability to add a single dose of detection reagents in an "add and read" assay format (e.g., homogeneous assay) that does not require washing away components that reduce assay sensitivity (e.g., decreased bioluminescent background). Additionally, embodiments of the present disclosure provide the ability to covalently label intracellular proteins without toxicity issues and with the sensitivity required to detect their release from cells in a quantitative manner using standard plate readers. Embodiments of the present disclosure also minimize the non-specific leakiness of probes from living cells and provide the sensitivity and robustness of bioluminescence detection required to follow the processes/responses of labeled cells over an extended length of time.

Section headings as used in this section and the entire disclosure herein are merely for organizational purposes and are not intended to be limiting.

1. DEFINITIONS

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present disclosure. All publications, patent applications, patents and other references mentioned herein are incorporated by reference in their entirety. The materials, methods, and examples disclosed herein are illustrative only and not intended to be limiting.

The terms "comprise(s)", "include(s)", "having", "has", "can", "contain(s)" and variants thereof, as used herein, are intended to be open-ended transitional phrases, terms, or words that do not preclude the possibility of additional acts or structures. The singular forms "a", "and" and "the" include plural references unless the context clearly dictates otherwise. Many embodiments herein are described using open "comprising" language. Such embodiments encompass multiple closed "consisting of" and/or "consisting essentially of" embodiments, which may alternatively be claimed or described using such language. The present disclosure also contemplates other embodiments "comprising," "consisting of" and "consisting essentially of," the embodiments or elements presented herein, whether explicitly set forth or not.

For the recitation of numeric ranges herein, each intervening number therebetween with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

The term "alkyl", as used herein, means a straight or branched saturated hydrocarbon chain containing from 1 to 16 carbon atoms ($C_1$-$C_{16}$ alkyl), for example 1 to 14 carbon atoms ($C_1$-$C_{14}$ alkyl), 1 to 12 carbon atoms ($C_1$-$C_{12}$ alkyl), 1 to 10 carbon atoms ($C_1$-$C_{10}$ alkyl), 1 to 8 carbon atoms ($C_1$-$C_8$ alkyl), 1 to 6 carbon atoms ($C_1$-$C_6$ alkyl), or 1 to 4 carbon atoms ($C_1$-$C_4$ alkyl). Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl, n-undecyl, and n-dodecyl.

The term "alkylene", as used herein, refers to a divalent group derived from a straight or branched chain hydrocarbon of 1 to 10 carbon atoms ($C_1$-$C_{10}$ alkylene), for example, of 1 to 6 carbon atoms ($C_1$-$C_6$ alkylene). Representative examples of alkylene include, but are not limited to, —$CH_2$—, —$CH_2CH_2$—, —$CH(CH_3)$—, —$CH_2CH_2CH_2$—, —$CH_2CH(CH_3)$—, —$CH_2CH_2CH_2CH_2$—, —$CH_2CH(CH_3)CH_2$—, —$CH_2CH_2CH(CH_3)$—, —$CH_2CH_2CH_2CH_2$—, —$CH_2CH(CH_3)CH_2CH_2$—, —$CH(CH_3)CH_2CH_2CH_2$—, —$CH_2CH_2CH_2CH_2CH_2$—, —$CH_2CH_2CH(CH_3)CH_2CH_2$—, —$CH_2CH(CH_3)CH_2CH_2CH_2$—, and —$CH(CH_3)CH_2CH_2CH_2CH_2$—.

The term "aryl", as used herein, refers to a phenyl group or a bicyclic or tricyclic aromatic-fused ring system. Bicyclic-fused ring systems are exemplified by a phenyl group appended to the parent molecular moiety and fused to a phenyl group. Tricyclic-fused ring systems are exemplified by a phenyl group appended to the parent molecular moiety and fused to two other phenyl groups. Representative examples of bicyclic aryls include, but are not limited to, naphthyl. Representative examples of tricyclic aryls include, but are not limited to, anthracenyl and phenanthrenyl.

The term "arylene", as used herein, refers to a divalent aryl group, e.g., a phenylene group.

The term "halogen" or "halo", as used herein, means F, Cl, Br, or I.

The term "haloalkyl", as used herein, means an alkyl group, as defined herein, in which one or more hydrogen atoms are replaced by a halogen. For example, one, two, three, four, five, six, seven, or eight hydrogen atoms can be replaced by a halogen, or all hydrogen atoms can be replaced by a halogen. Representative examples of haloalkyl include, but are not limited to, fluoromethyl, difluoromethyl, trifluoromethyl, chloromethyl, dichloromethyl, trichloromethyl, 2-fluoroethyl, 2,2-difluoroethyl, 2,2,2-trifluoroethyl, perfluoroethyl, 2-fluoro-2-methylpropyl, 3,3,3-trifluoropropyl, 4-chlorobutyl, 5-chloropentyl, 6-chlorohexyl, 7-chloroheptyl, and 8-chlorooctyl.

"Bioluminescence" refers to production and emission of light by a chemical reaction catalyzed by, or enabled by, an enzyme, protein, protein complex, or other biomolecule (e.g., bioluminescent complex). In typical embodiments, a substrate for a bioluminescent entity (e.g., bioluminescent protein or bioluminescent complex) is converted into an unstable form by the bioluminescent entity; the substrate subsequently emits light.

"Capture element" as used herein refers to a molecular entity that forms a covalent or stable non-covalent interaction (e.g., bond) with a corresponding "capture agent."

"Biomolecule-reactive group" as used herein refers to a molecular entity that non-specifically forms a covalent or stable non-covalent interaction (e.g., bond) with a biomolecule (e.g., a protein, peptide, lipid, polynucleotide, or the like). "Protein-reactive group" as used herein refers to a molecular entity that non-specifically forms a covalent or stable non-covalent interaction (e.g., bond) with protein (e.g., binds to a protein side chain without significant preference for protein identity).

"Complementary" refers to the characteristic of two or more structural elements (e.g., peptide, polypeptide, nucleic acid, small molecule, etc.) of being able to hybridize, dimerize, or otherwise form a complex with each other. For example, a "complementary peptide and polypeptide" are capable of coming together to form a complex. Complementary elements may require assistance to form a complex (e.g., from interaction elements), for example, to place the elements in the proper conformation for complementarity, to co-localize complementary elements, to lower interaction energy for complementation, etc.

"Complex" refers to an assemblage or aggregate of molecules (e.g., peptides, polypeptides, etc.) in direct and/or indirect contact with one another. In one aspect, "contact," or more particularly, "direct contact" means two or more molecules are close enough so that attractive noncovalent interactions such as Van der Waal forces, hydrogen bonding, ionic, and hydrophobic interactions, and the like dominate the interaction of the molecules. In such an aspect, a complex of molecules (e.g., a peptide and polypeptide) is formed under assay conditions such that the complex is thermodynamically favored (e.g., compared to a non-aggregated, or non-complexed, state of its component molecules). As used herein, the term "complex", unless described as otherwise, refers to the assemblage of two or more molecules (e.g., peptides, polypeptides, or a combination thereof).

"Derivative" of an antibody as used herein may refer to an antibody having one or more modifications to its amino acid sequence when compared to a genuine or parent antibody and exhibit a modified domain structure. The derivative may still be able to adopt the typical domain configuration found in native antibodies, as well as an amino acid sequence, which is able to bind to targets (antigens) with specificity. Typical examples of antibody derivatives are antibodies coupled to other polypeptides, rearranged antibody domains, or fragments of antibodies. The derivative may also comprise at least one further compound, such as a protein domain linked by covalent or non-covalent bonds. The linkage can be based on genetic fusion according to the methods known in the art. The additional domain present in the fusion protein comprising the antibody may preferably be linked by a flexible linker, advantageously a peptide linker, wherein said peptide linker comprises plural, hydrophilic, peptide-bonded amino acids of a length sufficient to span the distance between the C-terminal end of the further protein domain and the N-terminal end of the antibody or vice versa. The antibody may be linked to an effector molecule having a conformation suitable for biological activity or selective binding to a solid support, a biologically active substance (e.g., a cytokine or growth hormone), a chemical agent, a peptide, a protein, or a drug, for example.

"Fragment" refers to a peptide or polypeptide that results from dissection or "fragmentation" of a larger whole entity (e.g., protein, polypeptide, enzyme, etc.), or a peptide or polypeptide prepared to have the same sequence as such. Therefore, a fragment is a subsequence of the whole entity (e.g., protein, polypeptide, enzyme, etc.) from which it is made and/or designed. A peptide or polypeptide that is not a subsequence of a preexisting whole protein is not a fragment (e.g., not a fragment of a preexisting protein). A peptide or polypeptide that is "not a fragment of a preexisting bioluminescent protein" is an amino acid chain that is not a subsequence of a protein (e.g., natural or synthetic) that: (1) was in physical existence prior to design and/or synthesis of the peptide or polypeptide, and (2) exhibits substantial bioluminescent activity.

As used herein, the term "antibody fragment" refers to a portion of a full-length antibody, including at least a portion of the antigen binding region or a variable region. Antibody fragments include, but are not limited to, Fab, Fab', F(ab')$_2$, Fv, scFv, Fd, variable light chain, variable heavy chain, diabodies, and other antibody fragments that retain at least a portion of the variable region of an intact antibody. See, e.g., Hudson et al. (2003) Nat. Med. 9:129-134; herein incorporated by reference in its entirety. In certain embodiments, antibody fragments are produced by enzymatic or chemical cleavage of intact antibodies (e.g., papain digestion and pepsin digestion of antibody) produced by recombinant DNA techniques, or chemical polypeptide synthesis. For example, a "Fab" fragment comprises one light chain and the Cm and variable region of one heavy chain. The heavy chain of a Fab molecule cannot form a disulfide bond with another heavy chain molecule. A "Fab'" fragment comprises one light chain and one heavy chain that comprises additional constant region, extending between the $C_{H1}$ and $C_{H2}$ domains. An interchain disulfide bond can be formed between two heavy chains of a Fab' fragment to form a "F(ab')$_2$" molecule. An "Fv" fragment comprises the variable regions from both the heavy and light chains, but lacks the constant regions. A single-chain Fv (scFv) fragment comprises heavy and light chain variable regions connected by a flexible linker to form a single polypeptide chain with an antigen-binding region. Exemplary single chain antibodies are discussed in detail in WO 88/01649 and U.S. Pat. Nos. 4,946,778 and 5,260,203; herein incorporated by reference in their entireties. In certain instances, a single variable region (e.g., a heavy chain variable region or a light chain variable region) may have the ability to recognize and bind antigen. Other antibody fragments will be understood by skilled artisans.

"Isolated polynucleotide" as used herein may mean a polynucleotide (e.g., of genomic, cDNA, or synthetic origin, or a combination thereof) that, by virtue of its origin, the isolated polynucleotide is not associated with all or a portion of a polynucleotide with which the "isolated polynucleotide" is found in nature; is operably linked to a polynucleotide that it is not linked to in nature; or does not occur in nature as part of a larger sequence.

"Non-luminescent" refers to an entity (e.g., peptide, polypeptide, complex, protein, etc.) that exhibits the characteristic of not emitting a detectable amount of light in the visible spectrum (e.g., in the presence of a substrate). For example, an entity may be referred to as non-luminescent if it does not exhibit detectable luminescence in a given assay. As used herein, the term "non-luminescent" is synonymous with the term "substantially non-luminescent". For example, a non-luminescent polypeptide is substantially non-luminescent, exhibiting, for example, a 10-fold or more (e.g., 100-fold, 200-fold, 500-fold, $1\times10^3$-fold, $1\times10^4$-fold, $1\times10^5$-fold, $1\times10^6$-fold, $1\times10^7$-fold, etc.) reduction in luminescence compared to a complex of the polypeptide with its non-luminescent complement peptide. In some embodiments, an entity is "non-luminescent" if any light emission is sufficiently minimal so as not to create interfering background for a particular assay.

"Non-luminescent peptide" and "non-luminescent polypeptide" refer to peptides and polypeptides that exhibit substantially no luminescence (e.g., in the presence of a substrate), or an amount that is beneath the noise, or a 10-fold or more (e.g., 100-fold, 200-fold, 500-fold, $1\times10^3$-fold, $1\times10^4$-fold, $1\times10^5$-fold, $1\times10^6$-fold, $1\times10^7$-fold, etc.) when compared to a significant signal (e.g., luminescent complex) under standard conditions (e.g., physiological conditions, assay conditions, etc.) and with typical instrumentation (e.g., luminometer, etc.). In some embodiments, such non-luminescent peptides and polypeptides assemble, according to the criteria described herein, to form a bioluminescent complex. As used herein, a "non-luminescent element" is a non-luminescent peptide or non-luminescent polypeptide. The term "bioluminescent complex" refers to the assembled complex of two or more non-luminescent peptides and/or non-luminescent polypeptides. The bioluminescent complex catalyzes or enables the conversion of a substrate for the bioluminescent complex into an unstable form; the substrate subsequently emits light. When uncomplexed, two non-luminescent elements that form a bioluminescent complex may be referred to as a "non-luminescent pair." If a bioluminescent complex is formed by three or more non-luminescent peptides and/or non-luminescent polypeptides, the uncomplexed constituents of the bioluminescent complex may be referred to as a "non-luminescent group."

"Cell impermeable" as used herein refers to a compound or moiety that is not capable of passing through a cell membrane to the extent that an effective amount of the compound or moiety is intracellularly delivered.

"Cell permeable" as used herein refers to a compound or moiety that is capable of passing through a cell membrane to the extent that an effective amount of the compound is intracellularly delivered.

"Coelenterazine" as used herein refers to naturally-occurring ("native") coelenterazine. As used herein, the term "coelenterazine analog" or "coelenterazine derivative" refers to synthetic (e.g., derivative or variant) and natural analogs thereof, including furimazine, coelenterazine-n, coelenterazine-f, coelenterazine-h, coelenterazine-hcp, coelenterazine-cp, coelenterazine-c, coelenterazine-e, coelenterazine-fcp, bis-deoxycoelenterazine ("coelenterazine-hh"), coelenterazine-i, coelenterazine-icp, coelenterazine-v, and 2-methyl coelenterazine, in addition to those disclosed in WO 2003/040100; U.S. application Ser. No. 12/056,073 (paragraph [0086]); U.S. Pat. No. 8,669,103; WO 2012/061529, U.S. Pat. Pub. 2017/0233789 and U.S. Pat. Pub. 2018/0030059; the disclosures of which are incorporated by reference herein in their entireties. In some embodiments, coelenterazine analogs include pro-substrates such as, for example, those described in U.S. application Ser. No. 12/056,073; U.S. Pub. No. 2012/0707849; U.S. Pub. No. 2014/0099654; herein incorporated by reference in their entireties.

"Peptide" and "polypeptide" as used herein, and unless otherwise specified, refer to polymer compounds of two or more amino acids joined through the main chain by peptide amide bonds (—C(O)NH—). The term "peptide" typically refers to short amino acid polymers (e.g., chains having fewer than 25 amino acids), whereas the term "polypeptide" typically refers to longer amino acid polymers (e.g., chains having more than 25 amino acids).

"Preexisting protein" refers to an amino acid sequence that was in physical existence prior to a certain event or date. A "peptide that is not a fragment of a preexisting protein" is a short amino acid chain that is not a fragment or subsequence of a protein (e.g., synthetic or naturally-occurring) that was in physical existence prior to the design and/or synthesis of the peptide.

"Sample", "test sample", "specimen", "sample from a subject", and "patient sample" as used herein may be used interchangeable and may be a sample of blood, such as whole blood, tissue, urine, serum, plasma, amniotic fluid, cerebrospinal fluid, placental cells or tissue, endothelial cells, leukocytes, or monocytes. The sample can be used directly as obtained from a patient or can be pre-treated, such as by filtration, distillation, extraction, concentration, centrifugation, inactivation of interfering components, addition of reagents, and the like, to modify the character of the sample in some manner as discussed herein or otherwise as is known in the art.

"Sequence identity" refers to the degree two polymer sequences (e.g., peptide, polypeptide, nucleic acid, etc.) have the same sequential composition of monomer subunits. The term "sequence similarity" refers to the degree with which two polymer sequences (e.g., peptide, polypeptide, nucleic acid, etc.) have similar polymer sequences. For example, similar amino acids are those that share the same biophysical characteristics and can be grouped into the families, e.g., acidic (e.g., aspartate, glutamate), basic (e.g., lysine, arginine, histidine), non-polar (e.g., alanine, valine, leucine, isoleucine, proline, phenylalanine, methionine, tryptophan) and uncharged polar (e.g., glycine, asparagine, glutamine, cysteine, serine, threonine, tyrosine). The "percent sequence identity" (or "percent sequence similarity") is calculated by: (1) comparing two optimally aligned sequences over a window of comparison (e.g., the length of the longer sequence, the length of the shorter sequence, a specified window), (2) determining the number of positions containing identical (or similar) monomers (e.g., same amino acids occurs in both sequences, similar amino acid occurs in both sequences) to yield the number of matched positions, (3) dividing the number of matched positions by the total number of positions in the comparison window (e.g., the length of the longer sequence, the length of the shorter sequence, a specified window), and (4) multiplying the result by 100 to yield the percent sequence identity or percent sequence similarity. For example, if peptides A and B are both 20 amino acids in length and have identical amino acids at all but 1 position, then peptide A and peptide B have 95% sequence identity. If the amino acids at the non-identical position shared the same biophysical characteristics (e.g., both were acidic), then peptide A and peptide B would have 100% sequence similarity. As another example, if peptide C is 20 amino acids in length and peptide D is 15 amino acids in length, and 14 out of 15 amino acids in peptide D are identical to those of a portion of peptide C, then peptides C and D have 70% sequence identity, but peptide D has 93.3% sequence identity to an optimal comparison window of peptide C. For the purpose of calculating "percent sequence identity" (or "percent sequence similarity") herein, any gaps in aligned sequences are treated as mismatches at that position.

"Subject" and "patient" as used herein interchangeably refers to any vertebrate, including, but not limited to, a mammal and a human. In some embodiments, the subject may be a human or a non-human. The subject or patient may be undergoing forms of treatment. "Mammal" as used herein refers to any member of the class Mammalia, including, without limitation, humans and nonhuman primates such as chimpanzees and other apes and monkey species; farm animals such as cattle, sheep, pigs, goats, llamas, camels, and horses; domestic mammals such as dogs and cats; laboratory animals including rodents such as mice, rats, rabbits, guinea pigs, and the like. The term does not denote a particular age or sex. Thus, adult and newborn subjects, as well as fetuses, whether male or female, are intended to be included within the scope of this term.

"Subsequence" refers to peptide or polypeptide that has 100% sequence identify with another, larger peptide or polypeptide. The subsequence is a perfect sequence match for a portion of the larger amino acid chain.

"Substantially" as used herein means that the recited characteristic, parameter, and/or value need not be achieved exactly, but that deviations or variations, including for example, tolerances, measurement error, measurement accuracy limitations and other factors known to skill in the art, may occur in amounts that do not preclude the effect the characteristic was intended to provide. A characteristic or feature that is substantially absent (e.g., substantially non-luminescent) may be one that is within the noise, beneath background, below the detection capabilities of the assay being used, or a small fraction (e.g., <1%, <0.1%, <0.01%, <0.001%, <0.00001%, <0.000001%, <0.0000001%) of the significant characteristic (e.g., luminescent intensity of a bioluminescent protein or bioluminescent complex).

"Variant" is used herein to describe a peptide or polypeptide that differs in amino acid sequence by the insertion, deletion, or conservative substitution of amino acids, but retain at least one biological activity. "SNP" refers to a variant that is a single nucleotide polymorphism. Representative examples of "biological activity" include the ability to be bound by a specific antibody or to promote an immune response. Variant is also used herein to describe a protein with an amino acid sequence that is substantially identical to a referenced protein with an amino acid sequence that retains at least one biological activity. A conservative substitution of an amino acid (e.g., replacing an amino acid with a different amino acid of similar properties, such as hydrophilicity, degree, and distribution of charged regions) is recognized in the art as typically involving a minor change. These minor changes can be identified, in part, by considering the hydropathic index of amino acids, as understood in the art. The hydropathic index of an amino acid is based on a consideration of its hydrophobicity and charge. It is known in the art that amino acids of similar hydropathic indexes can be substituted and still retain protein function. In one aspect, amino acids having hydropathic indexes of ±2 are substituted. The hydrophilicity of amino acids can also be used to reveal substitutions that would result in proteins retaining biological function. A consideration of the hydrophilicity of amino acids in the context of a peptide permits calculation of the greatest local average hydrophilicity of that peptide, a useful measure that has been reported to correlate well with antigenicity and immunogenicity. Substitution of amino acids having similar hydrophilicity values can result in peptides retaining biological activity, for example immunogenicity, as is understood in the art. Substitutions may be performed with amino acids having hydrophilicity values within ±2 of each other. Both the hydrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties.

Unless otherwise defined herein, scientific and technical terms used in connection with the present disclosure shall have the meanings that are commonly understood by those of ordinary skill in the art. For example, any nomenclatures used in connection with, and techniques of, cell and tissue culture, molecular biology, immunology, microbiology, genetics and protein and nucleic acid chemistry and hybridization described herein are those that are well known and commonly used in the art. The meaning and scope of the terms should be clear; in the event, however of any latent ambiguity, definitions provided herein take precedent over any dictionary or extrinsic definition. Further, unless otherwise required by context, singular terms shall include pluralities and plural terms shall include the singular.

In the biologics field, it is advantageous to measure the fate of specific cell populations within a heterogenous mixture of cells, and in particular, to measure the death of targeted cancer cells caused by cytotoxic T lymphocytes (CTLs) or natural killer (NK) cells. One method that has been widely employed for such applications is the chromium release assay, which involves loading cells with radioactive chromium and monitoring its release upon cell death. Similar approaches have been developed to avoid the use of radioactivity such as methods involving the pre-loading the cells with fluorescent dyes and measuring release of the dye into the medium upon cell death. Collectively, a major challenge of such approaches is the non-specific release of labeling probes from the live cell populations, restricting their use to short-term measurements (e.g., 2-4 hours). In many cases, the probes released from dead cells have to be separated from live cells before detection, making it technically challenging to use these types of assays for a more high-throughput "add and read" format (e.g., homogeneous assay), which can increase assay variability. To address these challenges, alternative assays have been developed, for example, introducing reporter genes into the cells-of-interest. In some cases, the introduction of bioluminescence reporters addresses leakiness issues and provides a quantitative approach with high sensitivity, but it also requires cell engineering that is time consuming and can be challenging when working with primary cells. Therefore, a need remains for a non-radioactive approach with minimal leakiness that provides homogeneous, sensitive, and quantitative detection of specific cell death within a mixed cell culture without the need for cell engineering.

2. MULTIFUNCTIONAL PROBES

Embodiments of the present disclosure include multifunctional probes that can be used to detect a biomolecule-of-interest (e.g., a protein, peptide, lipid, polynucleotide, etc.). In some embodiments, the multifunctional probes are cell permeable (e.g., can be provided extracellularly and bind to an intracellular biomolecule). In some embodiments, the multifunctional probes are cell impermeable (e.g., cannot enter a cell when provided extracellularly and are only capable of binding extracellular biomolecules). In some embodiments, the multifunctional probe is capable of being linked to a biomolecule and can facilitate detection of the biomolecule through its attachment to one or more peptides or polypeptides capable of bioluminescence. In some embodiments, bioluminescent detection of the biomolecule is indicative of a cellular response that involves release of the biomolecule (e.g., cell death or apoptosis). In some embodiments, the multifunctional probe is capable of being linked to a biomolecule and can facilitate fluorescent detection and/or imaging through its attachment to one or more fluorescently-labeled peptides or polypeptides capable of bioluminescence (e.g., HiBiT fluorescently-labeled peptide). In some embodiments, the use of multifunctional probes of the present disclosure that are capable of producing both bioluminescent and fluorescent signals allows for the differentiation of one cell type among others based on the presence or absence of the bioluminescent and/or fluorescent signal, which can be indicative of a certain cellular response.

In some embodiments, a multifunctional probe comprises at least one capture element (e.g., chloroalkane group, biotin, etc.) and at least one biomolecule-reactive group (e.g., a functional group capable of forming a stable (e.g., covalent) bond with a biomolecule, such as a protein, a peptide, a lipid, a nucleotide, or the like. For example, in some embodiments, a multifunctional probe comprises at least one protein-reactive group capable of forming a stable (e.g., covalent) bond with a protein (e.g., non-specifically binding to, labeling, tagging, etc.) protein (e.g., in a cellular or other complex environment)) such as a succinimidyl ester moiety or maleimide group. In some embodiments, a multifunctional probe is a bifunctional probe and comprises one capture element (e.g., chloroalkane group) and one biomolecule-reactive group (e.g., a protein-reactive group such as a succinimidyl ester moiety). In some embodiments, in addition to one capture element (e.g., a chloroalkane group) and one biomolecule-reactive group, a multifunctional probe further comprises an additional functional group such as a second capture element, a fluorophore, etc., in which case, such probes may be considered trifunctional. In some embodiments, the various functional groups and moieties of the probes herein are connected by suitable linkers as is described in more detail herein.

In some embodiments, a multifunctional probe is a bifunctional probe comprising two functional elements (e.g., capture element and biomolecule-reactive group) connected directly (e.g., covalent bonded to one another) or via a linker. In some embodiments, such a linker further comprises one or more functional substituents, resulting in a trifunctional or other multifunctional probe.

In some embodiments, a probe herein is a bifunctional probe. For example, bifunctional probes of the present disclosure may include a succinimidyl ester (SE) and chloroalkane (Cl) functional groups. When introduced into live cells, the succinimidyl ester moiety may covalently attach to free amino groups on a biomolecule (e.g., intracellular protein, extracellular protein, membrane protein, lipid, etc.). When these biomolecules labeled with the bifunctional probes are released from live cells (e.g., upon cell death), they can be detected using, for example, a modified haloalkane dehydrogenase protein that covalently binds the chloroalkane functional groups on proteins previously labeled with the bifunctional probe (e.g., HALOTAG as provided in U.S. Pat. No. 7,238,842, which is herein incorporated by reference in its entirety). In some embodiments, the modified halo-alkane dehydrogenase protein is bound to one or more peptides or polypeptides capable of bioluminescent detection.

In other embodiments, bifunctional probes of the present disclosure may use biotin/streptavidin systems. For example, bifunctional probes may include biotin bound to a succinimidyl ester (SE) group (or other functional group) that can covalently attach to free amino groups on a biomolecule (e.g., intracellular protein, extracellular protein, membrane protein, lipid, etc.). These biomolecules can then be detected by binding to the complementary streptavidin bound to one or more peptides or polypeptides capable of bioluminescence. Other systems comprised of complementary binding partners can also be used as would be recognized by one of skill in the art based on the present disclosure.

In some embodiments, multifunctional probes of the present disclosure are capable of being linked to a biomolecule and can facilitate fluorescent detection and/or imaging through attachment to one or more fluorescently-labeled peptides or polypeptides capable of bioluminescence. For example, one or more components of the NanoBiT® system (e.g., SmBiT, HiBiT, LgBiT) are labeled with a fluorescent tag or fluorophore. In accordance with these embodiments, a fluorescent signal can be detected independent of a bioluminescent signal (e.g., generated upon formation of a bioluminescent complex/complementation). The ability to generate bioluminescent and fluorescent signals can facilitate enhanced detection and quantification of a biomolecule and/or a cell associated with the biomolecule.

In embodiments, the disclosure provides a compound of formula (I):

A-X-B    (I)

or a salt thereof, wherein:
A is a capture element;
X is a linker; and
B is a biomolecule-reactive group.

In compounds of formula (I), A is a capture element, which is a molecular entity that forms a covalent bond with a particular capture agent or a stable non-covalent interaction with a particular capture agent. In some embodiments, A is a covalent substrate for an enzyme (e.g., a substrate that a modified enzyme forms a covalent or other stable bond with instead of catalyzing the conversion of the substrate to a product). In some embodiments, the substrate is recognized by a mutant enzyme and forms a covalent bond thereto. In such embodiments, while the interaction of the substrate and a wild-type version of the enzyme results in formation of a product and the regeneration of the wild-type enzyme, interaction of the substrate with the mutant version of the enzyme results in formation of a covalent bond between the enzyme and substrate. The substrate may be any suitable substrate for any mutant enzyme that has been altered to form a stable or covalent bond with its substrate that would ordinarily only transiently bound by the enzyme.

In some embodiments, A comprises a haloalkyl group (e.g., a $C_2$-$C_{12}$ haloalkyl group). In such embodiments, A is a substrate for a dehalogenase, e.g., a haloalkane dehalogenase. Systems comprising mutant hydrolases (e.g., mutant dehalogenases) that covalently bind their substrates (e.g., haloalkyl substrates) are described, for example, in U.S. Pat. Nos. 7,238,842; 7,425,436; 7,429,472; 7,867,726; each of which is herein incorporated by reference in its entirety. HALOTAG is a commercially-available modified dehalogenase enzyme that forms a stable (e.g., covalent) bond (e.g., ester bond) with its haloalkyl substrate, which finds use in embodiments herein.

In some embodiments, A has the formula —$(CH_2)_n$—X, wherein n is 4, 5, 6, 7, or 8, and X is a halogen (i.e., F, Cl, Br, or I). In some embodiments, X is Cl. In some embodiments, n is 6 and X is Cl, such that A has formula —$(CH_2)_6$—Cl. In some embodiments, the haloalkyl group may be further substituted with substituents that do not interfere with interaction with the mutant dehalogenase.

In some embodiments, a capture element is an "affinity molecule", and the corresponding capture agent is an "acceptor" (e.g., small molecule, protein, antibody, etc.) that selectively interacts with such an affinity molecule. Examples of such pairs would include: an antigen as the capture element and an antibody as the capture agent; a small molecule as the capture element and a protein with high affinity for the small molecule as the capture agent (e.g., streptavidin and biotin), and the like.

In compounds of formula (I), B is a biomolecule-reactive group. In some embodiments, the biomolecule-reactive group is a group that can react with a biomolecule of interest, such as a protein, a peptide, a lipid, a polynucleotide, or the like. In some embodiments, a biomolecule-reactive group reacts non-specifically with one or more classes of biomolecules (e.g., proteins, peptides, lipids, polynucleotides, etc.). The biomolecule may be any biomolecule associated with the cell, such as an intracellular or extracellular biomolecule. In some embodiments, B is a protein-reactive group. In some embodiments, B is a functional group capable of forming a covalent bond with a protein (e.g., an intracellular protein, an extracellular protein, a membrane protein, etc.). For example, in some embodiments, B is a functional group that is capable of reacting with an amino acid side chain to form a covalent bond. In some embodiments, B is selected from a succinimidyl ester, a maleimide, an isocyanate, an isothiocyanate, a pentafluorophenyl ester, and a tetrafluorophenyl ester. In some embodiments, B is a succinimidyl ester, which can react with free amino groups of proteins, such as an amino group of a lysine side chain, to form an amide bond. In some embodiments, B is a functional group capable of forming a covalent bond with a lipid. In some embodiments, B is a functional group that acts as a suicide substrate for an enzyme, such that a covalent bond is formed between the compound of formula (I) and the enzyme.

In compounds of formula (I), X is a linker. A wide variety of linkers can be used in compounds of formula (I). In some embodiments, the linker comprises alkylene, arylene, —O—, —NH—, carbamate, and —C(O)— groups. For example, the linker may include various combinations of such groups to provide linkers having ester (—C(O)O—), amide (—C(O)NH—), carbamate (—NHC(O)O—), urea (—NHC(O)NH—), phenylene (e.g., 1,4-phenylene), straight or branched chain alkylene, and/or oligo- and polyethylene glycol (—$(CH_2CH_2O)_x$—) linkages, and the like. In some embodiments, the linker may include 2 or more atoms (e.g., 2-200 atoms, such as 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 110, 120, 130, 140, 150, 160, 170, 180, 190, or 200 atoms, or any range therebetween (e.g., 2-20, 5-10, 15-35, 25-100, etc.)). For example, in some embodiments, the linker comprises a group of formula:

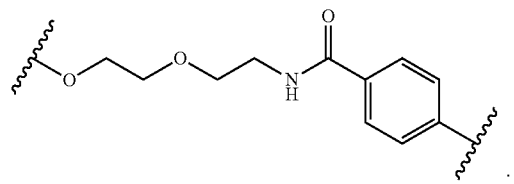 [SMILES: *OCCOCCNC(=O)c1ccc(*)cc1]

In some embodiments, the linker comprises a carbon or nitrogen atom that is substituted with a suitable substituent. In some embodiments, a suitable substituent comprises a third functional group (e.g., rendering an otherwise bifunctional probe trifunctional). For example, in some embodiments, the linker may include a carbon or nitrogen atom that is substituted with a second capture element A'. In some embodiments, A' is any group described herein for group A, such as a haloalkyl group (e.g., a $C_2$-$C_{12}$ haloalkyl group, such as a group of formula —$(CH_2)_n$—X, wherein n is 4, 5, 6, 7, or 8, and X is a halogen such as Cl). In some embodiments, A' has formula —$(CH_2)_6$—Cl. In some embodiments, the linker comprises a carbon or nitrogen atom that is substituted with a fluorophore. Suitable fluorophores include, but are not limited to, fluorescein and fluorescein dyes (e.g., fluorescein isothiocyanate or FITC, naphthofluorescein, 4',5'-dichloro-2',7'-dimethoxy-fluorescein, 6-carboxyfluoresceins (e.g., FAM)), rhodamine dyes (e.g., carboxytetramethylrhodamine or TAMRA, carboxyrhodamine 6G, carboxy-X-rhodamine (ROX), lissamine rhodamine B, rhodamine 6G, rhodamine Green, rhodamine Red, tetramethylrhodamine or TMR), coumarin and coumarin dyes (e.g., methoxycoumarin, dialkylaminocoumarin, hydroxycoumarin and aminomethylcoumarin or AMCA), Oregon Green Dyes (e.g., Oregon Green 488, Oregon Green 500, Oregon Green 514), Texas Red, Texas Red-X, SPECTRUM RED™, SPECTRUM GREEN™, cyanine dyes (e.g., CY-3™, CY-S™, CY-3.5™, CY-5.5™), Alexa Fluor dyes (e.g., Alexa Fluor 350, Alexa Fluor 488, Alexa Fluor 532, Alexa Fluor 546, Alexa Fluor 568, Alexa Fluor 594, Alexa Fluor 633, Alexa Fluor 660 and Alexa Fluor 680), BODIPY dyes (e.g., BODIPY FL, BODIPY R6G, BODIPY TMR, BODIPY TR, BODIPY 530/550, BODIPY 558/568, BODIPY 564/570, BODIPY 576/589, BODIPY 581/591, BODIPY 630/650, BODIPY 650/665), IRDyes (e.g., IRD40, IRD 700, IRD 800), and the like. Examples of other suitable fluorescent dyes that can be used and methods for linking or incorporating fluorescent dyes to oligonucleotides, such as probes, can be found in RP Haugland, "The Handbook of Fluorescent Probes and Research Chemicals", Molecular Probes, Inc., Eugene, Oreg. (June 1992)). In some embodiments, the fluorophore is carboxytetramethylrhodamine (TAMRA). In other embodiments, the linker comprises a carbon or nitrogen atom that is substituted with a second biomolecule-reactive group (B'). In some embodiments, B' is any group described herein for group B, such as a SE group or maleimide. In other embodiments, a linker comprises a carbon or nitrogen atom that is substituted with a peptide capable of forming a bioluminescent complex with one or more additional peptide or polypeptide components (e.g., a NanoBiT® (See, e.g., U.S. Pat. No. 9,797,889; herein incorporated by reference in its entirety) or NanoTrip™ peptide (See, e.g., Intl. App. No. PCT/US19/36844; herein incorporated by reference in its entirety). In still other embodiments, a linker comprises a carbon or nitrogen atom that is substituted with any suitable functional moiety of chemical group, such as a handle, detectable moiety, tag, peptide, epitope, etc.

Suitable compounds comprise any combinations of the above A, X, and B (and/or A', B', or additional moieties (e.g., fluorophores)). In some embodiments, the compound is selected from:

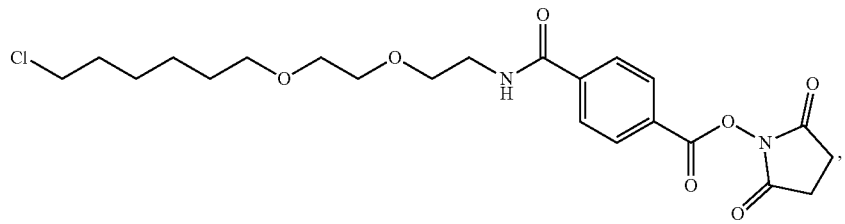

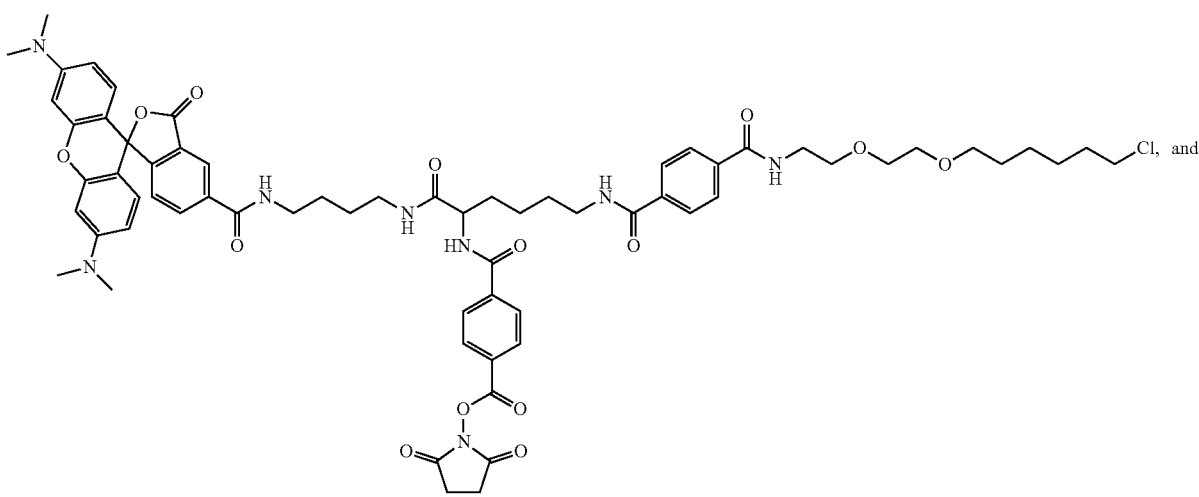

-continued

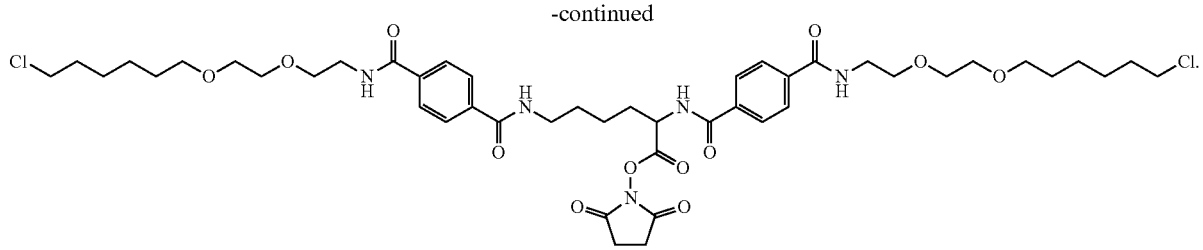

In some embodiments, the compound of formula (I) is cell-permeable. This property allows the compounds to be used, for example, in the methods described herein, such as methods in which compounds of formula (I) are used to covalently label intracellular proteins in live cells.

A compound of formula (I) may be in the form of a salt. The salts may be prepared during the final isolation and purification of the compounds or separately, for example by reacting a basic group of the compound (e.g., an amino group) with a suitable acid or by reacting an acidic group of the compound (e.g., a carboxylic acid group) with a suitable base.

Acid salts may be prepared during the final isolation and purification of the compounds or separately by reacting a suitable group of the compound such as an amino group with a suitable acid. For example, a compound may be dissolved in a suitable solvent, such as but not limited to methanol and water, and treated with at least one equivalent of an acid such hydrochloric acid. The resulting salt may precipitate out and be isolated by filtration and dried under reduced pressure. Alternatively, the solvent and excess acid may be removed under reduced pressure to provide a salt. Representative salts include acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, formate, isethionate, fumarate, lactate, maleate, methanesulfonate, naphthylenesulfonate, nicotinate, oxalate, pamoate, pectinate, persulfate, 3-phenylpropionate, picrate, oxalate, maleate, pivalate, propionate, succinate, tartrate, trichloroacetate, trifluoroacetate, glutamate, para-toluenesulfonate, undecanoate, hydrochloric, hydrobromic, sulfuric, phosphoric, and the like. The amino groups of the compounds may also be quaternized with alkyl chlorides, bromides and iodides such as methyl, ethyl, propyl, isopropyl, butyl, lauryl, myristyl, stearyl, and the like.

Basic addition salts may be prepared during the final isolation and purification of the disclosed compounds by reaction of a carboxyl group with a suitable base such as the hydroxide, carbonate, or bicarbonate of a metal cation such as lithium, sodium, potassium, calcium, magnesium, or aluminum, or an organic primary, secondary, or tertiary amine. Quaternary amine salts can be prepared, such as those derived from methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine and N,N'-dibenzylethylenediamine, ethylenediamine, ethanolamine, diethanolamine, piperidine, piperazine, and the like.

Compounds of formula (I) may be synthesized by a variety of methods, including those illustrated in Scheme 1.

Scheme 1.

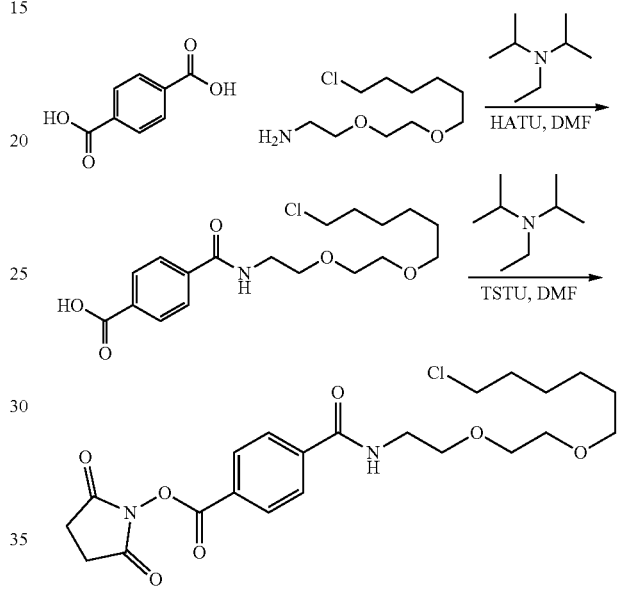

Routine experimentations, including appropriate manipulation of the reaction conditions, reagents and sequence of the synthetic route, protection of any chemical functionality that cannot be compatible with the reaction conditions, and deprotection at a suitable point in the reaction sequence of the method are included in the scope of the disclosure. Suitable protecting groups and the methods for protecting and deprotecting different substituents using such suitable protecting groups are well known to those skilled in the art; examples of which can be found in PGM Wuts and TW Greene, in Greene's book titled Protective Groups in Organic Synthesis (4' ed.), John Wiley & Sons, NY (2006), which is incorporated herein by reference in its entirety. Synthesis of the compounds of the disclosure can be accomplished by methods analogous to those described in the synthetic schemes described herein and in specific examples.

3. BIOLUMINESCENCE

The present disclosure provides assays, systems, and methods for detecting and/or measuring the responses of specific cell populations (e.g., pre-labeled) in co-culture systems (e.g., containing non-labeled cells). In accordance with these embodiments, the present disclosure provides materials and methods for the detection and/or quantification of a biomolecule and/or a cellular response associated with a biomolecule using multifunctional (e.g., bifunctional) probes that link bioluminescent/fluorescent polypeptides and/or bioluminescent/fluorescent complexes (of peptide or polypeptide components) to the biomolecule. In some embodiments, the bioluminescent/fluorescent polypeptides and/or bioluminescent/fluorescent complexes are linked to a multifunctional probe using a protein agent (e.g., modified halo-alkane dehydrogenase protein (e.g., HALOTAG), etc.) that covalently binds a functional group (e.g., haloalkane) on the multifunctional probe that is bound to the biomolecule. In other embodiments, the protein agent can be a specific binding partner or ligand for the biomolecule (e.g., a ligand binding to a cell surface receptor), which can provide greater specificity for labeling a cell population expressing only that biomolecule. In some embodiments, the protein agent can be modified such that it forms a covalent bond with its biomolecule binding partner upon interacting at the cell surface.

In some embodiments, provided herein are materials and methods related to bioassays for the detection of biomolecules released from cells. Biomolecule release from cells may occur as the result of (e.g., in reaction to) a stimulus or cellular response to a stimulus. In some embodiments, biomolecule release can occur as a result of cell death, cytotoxicity, membrane permeabilization (e.g., caused by a small molecule, protein/peptide, or electrical stimulus), active transport mechanisms, an immune response, facilitated diffusion, and the like. In some embodiments, biomolecule release occurs via secretion of the biomolecule itself from the cell. In other embodiments, a biomolecule is released in a vesicle, including but not limited to, an exosome, a lysosome, a microvesicle, an extracellular vesicle, and the like. In some embodiments, a biomolecule is released from a vesicle that is secreted from a cell, or a biomolecule is present on the surface of the vesicle membrane (a cell-associated biomolecule). In accordance with these embodiments, the biomolecule can be a protein, a lipid, a polynucleotide (e.g., DNA or RNA), or a combination thereof that is present in the vesicle (e.g., exosome), on the vesicle membrane, and/or excreted from the vesicle.

In some embodiments of the present disclosure, a biomolecule (e.g., intracellular protein, extracellular protein, membrane protein, lipid, etc.) is (non-specifically) labeled (e.g., at amino groups) with a multifunctional probe comprising (i) a biomolecule-reactive group (e.g., for attachment of the probe to the intracellular biomolecule) and (ii) a capture element. If labeled biomolecules are released from the cell (e.g., due to cell permeabilization or cell death), the capture agent is made available for binding by an extracellular capture element. In some embodiments, binding of the capture agent to the biomolecule-bound capture elements allows for detection of the biomolecule and correlation to its release from the cell (e.g., cell permeabilization, cell death, etc.).

In some embodiments, capture agents are bound to (e.g., fusions with) peptide and/or polypeptide components of a bioluminescent complex such that upon binding of capture agents to the capture elements on the labeled biomolecules, a bioluminescent complex is formed of the peptide and polypeptide components, and bioluminescence can be detected. In some embodiments, the capture agents are not cell permeable, and therefore bioluminescence is only generated upon escape of the labelled protein from cells. In some embodiments, the level of bioluminescence is proportional to a stimulus or cellular response. In some embodiments, the level of bioluminescence is proportional to cellular death and/or permeabilization.

In some embodiments, provided herein are bioassays that incorporate multifunctional (e.g., bifunctional) probes and bioluminescent polypeptides and/or bioluminescent complexes (of peptide(s) and/or polypeptide components that exhibit enhanced luminescence upon complex formation) that are based on (e.g., structurally, functionally, etc.) the luciferase of Oplophorus gracilirostris, the NanoLuc® luciferase (Promega Corporation; U.S. Pat. Nos. 8,557,970; 8,669,103; herein incorporated by reference in their entireties), the NanoBiT® (U.S. Pat. No. 9,797,889; herein incorporated by reference in its entirety), NanoTrip' (U.S. Prov. Appln. Ser. No. 62/684,014; herein incorporated by reference in its entirety), and/or other multipartite bioluminescent technologies (Intl. App. No. PCT/US19/36844; herein incorporated by reference in its entirety). As described herein, bioassays can incorporate commercially available NanoLuc®-based technologies (e.g., NanoLuc® luciferase, NanoBRET™, NanoBiT®, NanoTrip™, NanoGlo®, etc.), but in other embodiments, various combinations, variations, or derivations from the commercially available NanoLuc®-based technologies are employed.

a. NANOLUC

PCT Appln. No. PCT/US2010/033449, U.S. Pat. No. 8,557,970, PCT Appln. No. PCT/2011/059018, and U.S. Pat. No. 8,669,103 (each of which is herein incorporated by reference in their entirety and for all purposes) describe compositions and methods comprising bioluminescent polypeptides. Such polypeptides find use in embodiments herein and can be used in conjunction with the compositions, assays, and methods described herein. In some embodiments, compositions, assays, and methods provided herein comprise a bioluminescent polypeptide of SEQ ID NO: 5 or having at least 60% (e.g., 60%, 65%, 70%, 75%, 80%, 85%, 90%, 95%, 96%, 97%, 98%, 99%, 100%, or ranges therebetween) sequence identity with SEQ ID NO: 5. In some embodiments, any of the aforementioned bioluminescent polypeptides are linked (e.g., fused, chemically linked, etc.) to a modified dehalogenase (e.g., HALOTAG) or utilize another system comprised of complementary binding partners b. Bioluminescent Complexes The native Oplophorus gracilirostris luciferase (OgLuc) and commercially-available NANOLUC luciferase (Promega Corporation) each comprise polypeptides of 10 β (beta) strands ($\beta 1$, $\beta 2$, $\beta 3$, $\beta 4$, $\beta 5$, $\beta 6$, $\beta 7$, $\beta 8$, $\beta 9$, $\beta 10$). U.S. Pat. No. 9,797,889 (herein incorporated by reference in its entirety) describes development and use of a complementation system comprising a $\beta 1$-9-like polypeptide and a $\beta 10$-like peptide (the actual polypeptide and peptide sequences in U.S. Pat. No. 9,797,889 differ from the corresponding sequences in NANOLUC and wild-type native OgLuc).

Multipartite complementation systems (e.g., bipartite, tripartite, etc.) have been developed by combining peptides and polypeptides that collectively correspond to the full set of 10 β (beta) strands of these luciferases. Upon combination of the set of complementary peptides and polypeptides, under appropriate conditions (e.g., facilitated by the binding of capture reagents fused to the complementation components to capture elements), a bioluminescent complex is formed. In some embodiments, peptide and polypeptide components of the bioluminescent complexes find use as detection reagents (e.g., fused to capture agents) for the detection of protein labeled by the compositions and methods herein (and thereby cell death is detected). These multipartite complementation systems are described in, for example, PCT Appln. No. PCT/US14/26354; U.S. Pat. No. 9,797,889; U.S. Prov. Appln. Ser. No. 62/684,014; and Intl. App. No. PCT/US19/36844 (herein incorporated by reference in their entireties and for all purposes); and examples of these technologies are described below.

1. NanoBiT® and Related Bipartite Technologies

PCT Appln. No. PCT/US14/26354 and U.S. Pat. No. 9,797,889 (each of which is herein incorporated by reference in their entirety and for all purposes) describe compositions and methods for the assembly of bioluminescent complexes; such complexes, and the peptide and polypeptide components thereof, find use in embodiments herein and can be used in conjunction with the compositions, assays, and methods described herein. In some embodiments, NanoBiT® and other related technologies utilize a peptide component and a polypeptide component that, upon assembly into a complex, exhibit significantly-enhanced (e.g., 2-fold, 5-fold, 10-fold, $10^2$-fold, $10^3$-fold, $10^4$-fold, or more) luminescence in the presence of an appropriate substrate (e.g., coelenterazine or a coelenterazine analog) when compared to the peptide component and polypeptide component alone.

In some embodiments, provided herein are polypeptide components having at least 60% (e.g., 60%, 65%, 70%, 75%, 80%, 85%, 90%, 95%, 96%, 97%, 98%, 99%, 100%, or ranges therebetween) sequence identity with SEQ ID NO: 9. In some embodiments, polypeptides have less than 100% (e.g., <99%, <98%, <97%, <96%, <95%, <94%, <93%, <92%, <91%, <90%) sequence identity with SEQ ID NO: 1, SEQ ID NO: 2, SEQ ID NO: 5, and/or SEQ ID NO: 6. In some embodiments, provided herein are peptide components having at least 60% (e.g., 60%, 65%, 70%, 75%, 80%, 85%, 90%, 95%, 96%, 97%, 98%, 99%, 100%, or ranges therebetween) sequence identity with SEQ ID NO: 10. In some embodiments, peptides have less than 100% (e.g., <99%, <98%, <97%, <96%, <95%, <94%, <93%, <92%, <91%, <90%) sequence identity with SEQ ID NO: 1, SEQ ID NO: 4, SEQ ID NO: 5, and/or SEQ ID NO: 8. In some embodiments, provided herein are peptide components having at least 60% (e.g., 60%, 65%, 70%, 75%, 80%, 85%, 90%, 95%, 96%, 97%, 98%, 99%, 100%, or ranges therebetween) sequence identity with SEQ ID NO: 11. In some embodiments, peptides have less than 100% (e.g., <99%, <98%, <97%, <96%, <95%, <94%, <93%, <92%, <91%, <90%) sequence identity with SEQ ID NO: 1, SEQ ID NO: 4, SEQ ID NO: 5, and/or SEQ ID NO: 8. In some embodiments, any of the aforementioned peptide or polypeptide components of a bioluminescent complex are linked (e.g., fused, chemically linked, etc.) to a modified dehalogenase (e.g., HALOTAG), or utilize another system comprised of complementary binding partners. In some embodiments, provided herein are peptide components having at least 60% (e.g., 60%, 65%, 70%, 75%, 80%, 85%, 90%, 95%, 96%, 97%, 98%, 99%, 100%, or ranges therebetween) sequence identity with SEQ ID NO: 10. In some embodiments, peptides have less than 100% (e.g., <99%, <98%, <97%, <96%, <95%, <94%, <93%, <92%, <91%, <90%) sequence identity with SEQ ID NO: 1, SEQ ID NO: 4, SEQ ID NO: 5, and/or SEQ ID NO: 8. In some embodiments, any of the aforementioned peptide or polypeptide components of a bioluminescent complex are linked (e.g., fused, chemically linked, etc.) to a modified dehalogenase (e.g., HALOTAG), or utilize another system comprised of complementary binding partners.

2. Multipartite NanoLuc® and Related Multipartite Technologies

U.S. Prov. Appln. Ser. No. 62/684,014 and Intl. App. No. PCT/US19/36844 (herein incorporated by reference in their entireties and for all purposes) describes compositions, systems, and methods for the assembly of bioluminescent complexes from three or more peptide and polypeptide components. Such complexes, and the peptides and polypeptide components thereof, can be used in conjunction with the compositions, assays, and methods described herein.

In some embodiments, provided herein are polypeptide components having at least 60% (e.g., 60%, 65%, 70%, 75%, 80%, 85%, 90%, 95%, 96%, 97%, 98%, 99%, 100%, or ranges therebetween) sequence identity with SEQ ID NO: 12 or 19. In some embodiments, polypeptides have less than 100% (e.g., <99%, <98%, <97%, <96%, <95%, <94%, <93%, <92%, <91%, <90%) sequence identity with SEQ ID NO: 1, SEQ ID NO: 2, SEQ ID NO: 5, SEQ ID NO: 6, and/or SEQ ID NO: 9.

In some embodiments, provided herein are peptide components having at least 60% (e.g., 60%, 65%, 70%, 75%, 80%, 85%, 90%, 95%, 96%, 97%, 98%, 99%, 100%, or ranges therebetween) sequence identity with SEQ ID NO: 11. In some embodiments, peptides have less than 100% (e.g., <99%, <98%, <97%, <96%, <95%, <94%, <93%, <92%, <91%, <90%) sequence identity with SEQ ID NO: 1, SEQ ID NO: 4, SEQ ID NO: 5, and/or SEQ ID NO: 8.

In some embodiments, provided herein are peptide components having at least 60% (e.g., 60%, 65%, 70%, 75%, 80%, 85%, 90%, 95%, 96%, 97%, 98%, 99%, 100%, or ranges therebetween) sequence identity with SEQ ID NO: 13. In some embodiments, peptides have less than 100% (e.g., <99%, <98%, <97%, <96%, <95%, <94%, <93%, <92%, <91%, <90%) sequence identity with SEQ ID NO: 1, SEQ ID NO: 3, SEQ ID NO: 5, and/or SEQ ID NO: 7.

In some embodiments, provided herein are peptide components having at least 60% (e.g., 60%, 65%, 70%, 75%, 80%, 85%, 90%, 95%, 96%, 97%, 98%, 99%, 100%, or ranges therebetween) sequence identity with SEQ ID NO: 14. In some embodiments, peptides have less than 100% (e.g., <99%, <98%, <97%, <96%, <95%, <94%, <93%, <92%, <91%, <90%) sequence identity with SEQ ID NO: 1, SEQ ID NO: 3, SEQ ID NO: 4, SEQ ID NO: 5, SEQ ID NO: 7, and/or SEQ ID NO: 8. In some embodiments, any of the aforementioned peptide and/or polypeptide components are linked (e.g., fused, chemically linked, etc.) to a modified dehalogenase (e.g., HALOTAG), or utilize another system comprised of complementary binding partners.

c. NanoBRET™

PCT Appln. No. PCT/US13/74765 and U.S. patent application Ser. No. 15/263,416 (herein incorporated by reference in their entireties and for all purposes) describes bioluminescence resonance energy transfer (BRET) compositions, assays, and methods (e.g., incorporating NanoLuc®-based technologies); such compositions, assays and methods, and the bioluminescent polypeptide and fluorophore-conjugated components thereof, can be used in conjunction with the compositions, assays, and methods described herein. In some embodiments, any of the NanoLuc®-based, NanoBiT®-based, and/or multipartite NanoLuc®-based or related peptides, polypeptides, complexes, fusions, and conjugates may find use in BRET-based applications with the compositions, assays, and methods described herein.

As used herein, the term "energy acceptor" refers to any small molecule (e.g., chromophore), macromolecule (e.g., autofluorescent protein, phycobiliproteins, nanoparticle, surface, etc.), or molecular complex that produces a readily detectable signal in response to energy absorption (e.g., resonance energy transfer). In certain embodiments, an energy acceptor is a fluorophore or other detectable chromophore. Suitable fluorophores include, but are not limited to: xanthene derivatives (e.g., fluorescein, rhodamine, Oregon green, eosin, Texas red, etc.), cyanine derivatives (e.g., cyanine, indocarbocyanine, oxacarbocyanine, thiacarbocyanine, merocyanine, etc.), naphthalene derivatives (e.g., dansyl and prodan derivatives), oxadiazole derivatives (e.g., pyridyloxazole, nitrobenzoxadiazole, benzoxadiazole, etc.), pyrene derivatives (e.g., cascade blue), oxazine derivatives (e.g., Nile red, Nile blue, cresyl violet, oxazine 170, etc.), acridine derivatives (e.g., proflavin, acridine orange, acridine yellow, etc.), arylmethine derivatives (e.g., auramine, crystal violet, malachite green, etc.), tetrapyrrole derivatives (e.g., porphin, phtalocyanine, bilirubin, etc.), CF dye (Biotium), BODIPY (Invitrogen), ALEXA FLuoR (Invitrogen), DYLIGHT FLUOR (Thermo Scientific, Pierce), ATTO and TRACY (Sigma Aldrich), FluoProbes (Interchim), DY and MEGASTOKES (Dyomics), SULFO CY dyes (CYANDYE, LLC), SETAU AND SQUARE DYES (SETA BioMedicals), QUASAR and CAL FLUOR dyes (Biosearch Technologies), SURELIGHT DYES (APC, RPE, PerCP, Phycobilisomes)(Columbia Biosciences), APC, APCXL, RPE, BPE (Phyco-Biotech), autofluorescent proteins (e.g., YFP, RFP, mCherry, mKate), quantum dot nanocrystals, etc. In some embodiments, a fluorophore is a rhodamine analog (e.g., carboxy rhodamine analog), such as those described in U.S. patent application Ser. No. 13/682,589, herein incorporated by reference in its entirety. In some embodiments, a fluorophore of a multifunctional probe is an acceptor in a BRET application of the technology herein.

e. Luminogenic Substrates

The assays and methods of the present disclosure include the use of a luminogenic substrate. Bioluminescence, as described herein, generally refers to production and emission of light by a chemical reaction catalyzed by, or enabled by, an enzyme, protein, protein complex, or other biomolecule (e.g., bioluminescent complex). In typical embodiments, a luminogenic substrate for a bioluminescent entity (e.g., bioluminescent protein or bioluminescent complex) is converted into an unstable form by the bioluminescent entity; the substrate subsequently emits light. In the presence of detection reagents (e.g., polypeptide component(s) of a bioluminescent complex) and substrate (e.g., coelenterazine or coelenterazine analog), a bioluminescent signal is produced. Provided herein are compositions that include a luminogenic substrate such as coelenterazine or an analog or derivative thereof. Exemplary coelenterazine analogs include coelenterazine-h, coelenterazine-h-h, and furimazine.

In some embodiments, the substrate is coelenterazine, which has the following structure:

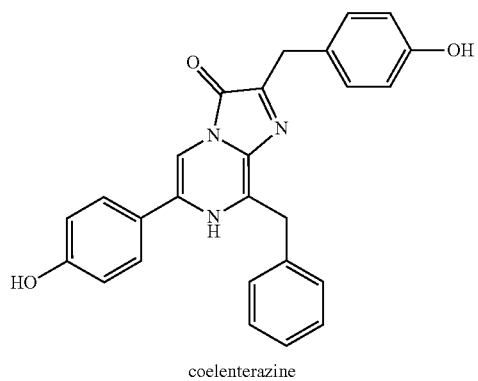 [SMILES: O=c1c(Cc2ccc(O)cc2)nc2c(Cc3ccccc3)[nH]c(-c3ccc(O)cc3)cn1-2]

coelenterazine

In some embodiments, the substrate is a coelenterazine analog or derivative. Exemplary coelenterazine analogs include coelenterazine-h (2-deoxycoelenterazine or 2,8-dibenzyl-6-(4-hydroxyphenyl)imidazo[1,2-a]pyrazin-3 (7H)-one), coelenterazine-h-h (dideoxycoelenterazine or 2,8-dibenzyl-6-phenylimidazo[1,2-a]pyrazin-3(7H)-one), and furimazine (8-benzyl-2-(furan-2-ylmethyl)-6-phenylimidazo[1,2-a]pyrazin-3(7H)-one), which have the following structures:

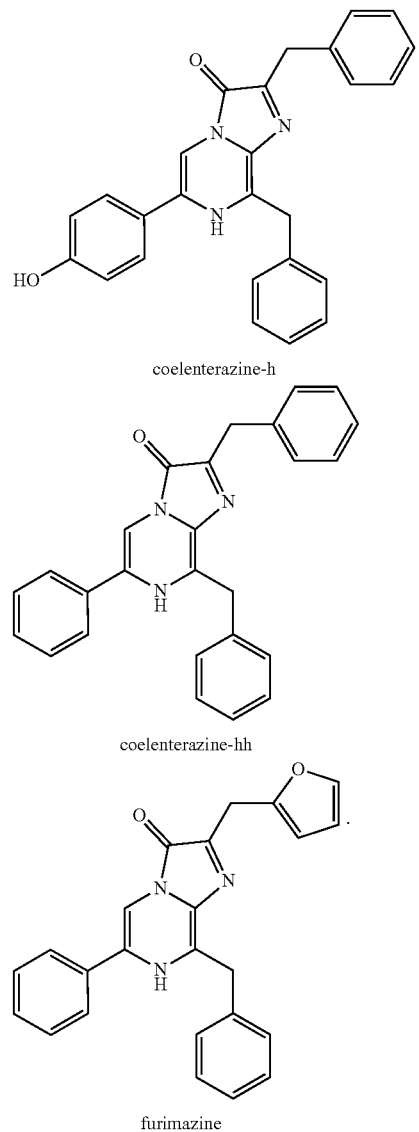

coelenterazine-h coelenterazine-hh furimazine

Additional exemplary coelenterazine analogs include coelenterazine-n, coelenterazine-f, coelenterazine-hcp, coelenterazine-cp, coelenterazine-c, coelenterazine-e, coelenterazine-fcp, coelenterazine-i, coelenterazine-icp, coelenterazine-v, 2-methyl coelenterazine, and the like. In some embodiments, the compound may be a coelenterazine analog described in WO 2003/040100; U.S. application Ser. No. 12/056,073 (paragraph [0086]); U.S. Pat. No. 8,669,103; WO 2012/061529, U.S. Pat. Pub. 2017/0233789 and U.S. Pat. Pub. 2018/0030059; the disclosures of which are incorporated by reference herein in their entireties. In some embodiments, coelenterazine analogs or derivatives include pro-substrates such as, for example, those described in U.S. application Ser. No. 12/056,073; U.S. Pub. No. 2012/0707849; U.S. Pub. No. 2014/0099654; herein incorporated by reference in their entireties. In some embodiments, the compound is furimazine.

Coelenterazine and analogs and derivatives thereof may suffer from challenges associated with their reconstitution into buffer systems used in many assays such as the bioluminogenic methods described herein. For example, coelenterazines, or analogs or derivatives thereof, such as furimazine, may dissolve slowly and/or inconsistently in buffer solutions (e.g., due to the heterogeneous microcrystalline nature of the solid material). While dissolution in organic solvent prior to dilution with buffer may provide faster and more consistent results, coelenterazine compounds may suffer from instability in organic solutions on storage, including both thermal instability and photo-instability. In some embodiments, the composition further comprises a polymer. As further described herein, the presence of the polymer may stabilize the compound against decomposition, and the presence of the polymer may improve the solubility of the compound in water or in aqueous solutions.

The polymer may be a naturally-occurring biopolymer or a synthetic polymer. In some embodiments, the polymer is a naturally-occurring biopolymer. Suitable naturally-occurring biopolymers are carbohydrates, including disaccharides (e.g., trehalose and maltose), and polysaccharides (e.g., pullulan, dextran, and cellulose). Mixtures of naturally-occurring biopolymers may also be used. In some embodiments, the polymer is pullulan, which is a polysaccharide that includes maltotriose repeating units. Maltotriose is a trisaccharide that includes three glucose units that are linked via α-1,4 glycosidic bonds. The maltotriose units within the pullulan polymer are linked to each other via α-1,6 glycosidic bonds.

In some embodiments, the polymer is a synthetic polymer. A synthetic polymer may be a homopolymer, copolymer, or block copolymer (e.g., diblock copolymer, triblock copolymer, etc.). Non-limiting examples of suitable polymers include, but are not limited to polyamines, polyethers, polyamides, polyesters, polycarbamates, polyureas, polycarbonates, polystyrenes, polyimides, polysulfones, polyurethanes, polyacetylenes, polyethylenes, polyethyeneimines, polyisocyanates, polyacrylates, polymethacrylates, polyacrylonitriles, and polyarylates. Non-limiting examples of specific polymers include poly(caprolactone) (PCL), ethylene vinyl acetate polymer (EVA), poly(lactic acid) (PLA), poly(L-lactic acid) (PLLA), poly(glycolic acid) (PGA), poly (lactic acid-co-glycolic acid) (PLGA), poly(L-lactic acid-co-glycolic acid) (PLLGA), poly(D,L-lactide) (PDLA), poly (L-lactide) (PLLA), poly(D,L-lactide-co-caprolactone), poly(D,L-lactide-co-caprolactone-co-glycolide), poly(D,L-lactide-co-PEO-co-D,L-lactide), poly(D,L-lactide-co-PPO-co-D,L-lactide), polyalkyl cyanoacrylate, polyurethane, poly-L-lysine (PLL), hydroxypropyl methacrylate (HPMA), poly(ethylene glycol), poly-L-glutamic acid, poly(hydroxy acids), polyanhydrides, polyorthoesters, poly(ester amides), polyamides, poly(ester ethers), polycarbonates, polyalkylenes (e.g., polyethylene and polypropylene), polyalkylene glycols (e.g., poly(ethylene glycol) (PEG)), polyalkylene terephthalates (e.g., poly(ethylene terephthalate), etc.), polyvinyl alcohols (PVA), polyvinyl ethers, polyvinyl esters (e.g., poly(vinyl acetate), etc.), polyvinyl halides (e.g., poly(vinyl chloride) (PVC), etc.), polyvinylpyrrolidone, polysiloxanes, polystyrene (PS), polyurethanes, derivatized celluloses (e.g., alkyl celluloses, hydroxyalkyl celluloses, cellulose ethers, cellulose esters, nitro celluloses, hydroxypropylcellulose, carboxymethylcellulose, etc.), polymers of acrylic acids ("polyacrylic acids") (e.g., poly(methyl(meth) acrylate) (PMMA), poly(ethyl(meth)acrylate), poly(butyl (meth)acrylate), poly(isobutyl(meth)acrylate), poly(hexyl (meth)acrylate), poly(isodecyl(meth)acrylate), poly(lauryl (meth)acrylate), poly(phenyl(meth)acrylate), poly(methyl acrylate), poly(isopropyl acrylate), poly(isobutyl acrylate), poly(octadecyl acrylate), polydioxanone and its copolymers (e.g., polyhydroxyalkanoates, polypropylene fumarate), polyoxymethylene, poloxamers, poly(ortho)esters, poly(butyric acid), poly(valeric acid), poly(lactide-co-caprolactone), trimethylene carbonate, and mixtures and copolymers thereof.

In addition to the compound and the polymer, the composition may include additional components such as buffers, surfactants, salts, proteins, or any combination thereof. For example, the composition may include a buffer such as a phosphate buffer, a borate buffer, an acetate buffer, or a citrate buffer, or other common buffers such as bicine, tricine, tris(hydroxymethyl)aminomethane (tris), N-[tris(hydroxymethyl)methyl]-3-aminopropanesulfonic acid (TAPS), 3-[N-tris(hydroxymethyl)methylamino]-2-hydroxypropanesulfonic acid (TAPSO), 2-[4-(2-hydroxyethyl) piperazin-1-yl]ethanesulfonic acid (HEPES), N-[tris(hydroxymethyl)methyl]-2-aminoethanesulfonic acid (TES), piperazine-N,N'-bis(2-ethanesulfonic acid) (PIPES), 2-(N-morpholino)ethanesulfonic acid (MES), or the like.

In some embodiments, the composition may include a surfactant. Exemplary surfactants include non-ionic surfactants, anionic surfactants, cationic surfactants, and zwitterionic surfactants. For example, the surfactant may be a non-ionic surfactant such as sorbitan 20. In some embodiments, the composition may include a salt, such as sodium chloride, potassium chloride, magnesium chloride, or the like. In some embodiments, the composition may include a protein. For example, the composition can include a carrier protein to prevent surface adsorption of luminogenic enzymes that may be added in downstream assays. In some embodiments, the protein may be bovine serum albumin (BSA).

4. DETECTION ASSAYS

Embodiments of the present disclosure include compositions, assays, and methods for labeling cells using a multifunctional (e.g., bifunctional, trifunctional, etc.) probe and detecting the labeled cells using bioluminescence. In particular embodiments, the assays herein provide for detecting escape of labeled intracellular protein from cells. Such escapes may occur as the result of an external stimulus and/or as the result of a cellular response to an external stimulus. In accordance with these embodiments, described below are exemplary assays and methods for use with various embodiments described herein. The following assays and methods should not be viewed as limiting the full scope of the embodiments, as described in the present disclosure.

As shown in FIGS. 1A-1B, bioluminescent assays can be performed using the complementary components of NanoLuc® Binary Technology (NanoBiT®) and a cell permeable multifunctional probe. As shown in FIG. 1B, the multifunctional probe can include, for example, a succinimidyl ester group for covalent labeling of intracellular proteins and a chloroalkane ligand for covalent binding to a HaloTag® protein. However, other multifunctional probes can also be used as would be recognized by one of ordinary skill in the art based on the present disclosure. For example, as shown in FIG. 1A, a population of cells can be labeled using a multifunctional probe capable of binding a biomolecule within the cells or located on the extracellular surface of the cells (a cell-associated biomolecule). The biomolecule can be a protein, a lipid, a polynucleotide (e.g., DNA or RNA), or a combination thereof that is present in the cell, located on the extracellular surface of the cell, and/or present in/on a vesicle associated with the cell (e.g., exosome). In some embodiments, the labeled cells can be combined or co-cultured with non-labeled cells. In some embodiments, a stimulus is applied directly (e.g., drug treatment) or applied indirectly (e.g., non-labeled cells exert an effect on the labeled cells) to the labeled cells, which causes a change in one or more aspects of the cells and/or the labeled biomolecules in/on the cells, which can be indicative of a cellular response.

Figure 7B:
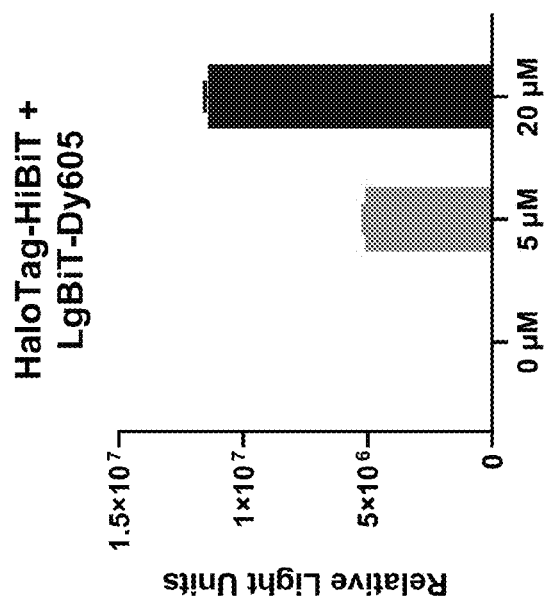
FIGS. 7A-7B include representative results of experiments conducted to detect both fluorescence and luminescence using HALOTAG-HiBiT and a fluorescently tagged LgBiT (LgBiT-Dy605) in cells labeled with a multifunctional chloroalkane probe.
Figure 7A:
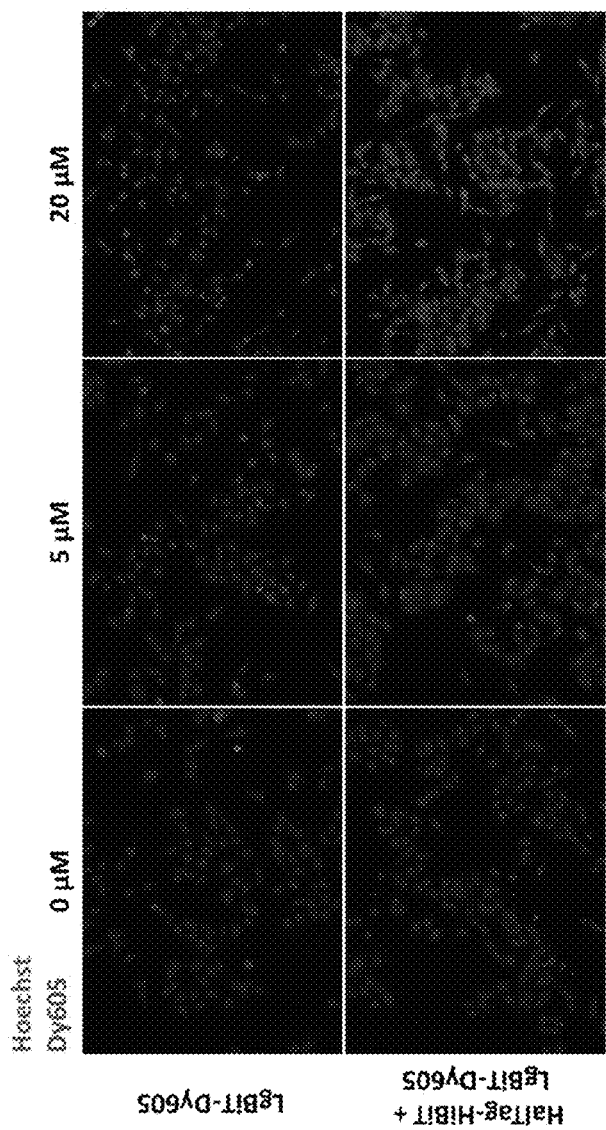

In accordance with these embodiments, the biomolecule is released from the cells, and this release can occur a result of cell death, cytotoxicity, membrane permeabilization (e.g., caused by a small molecule, protein/peptide, or electrical stimulus), active transport mechanisms, an immune response, facilitated diffusion, and the like. In some embodiments, biomolecule release occurs via secretion of the biomolecule itself from the cell. As shown in FIG. 1A, once released, the biomolecule can be detected and/or quantified using bioluminescent complexes, fluorescent tags, or combinations of both. For example, a HaloTag® protein can be fused to LgBiT and SmBiT (e.g., HALOTAG-SmBiT and HALOTAG-LgBiT), and their complementation upon binding the biomolecule via the multifunctional probe generates a bioluminescent signal that can be detected and/or quantified. Additionally, one or more components of the NanoBiT® system (e.g., HiBiT) can be labeled with a fluorescent tag or fluorophore to facilitate detection of both bioluminescent and fluorescent signals, which can provide enhanced signal detection and quantification (FIGS. 7A-7B). Additionally, one or more components of the NanoBiT® system (e.g., SmBiT) can be labeled with a specific antibody to facilitate detection of a bioluminescent signal when a complementary component of the NanoBiT® system (e.g., LgBiT) binds to the same target protein as the antibody, thus providing the ability to detect both a specific protein and a specific cellular response (e.g., detection of cytokines secreted from an immune cell in response to a stimulus). The various aspects of the above-described detection assays can be combined with each other and with other aspects of cell-based detection assays, as would be recognized by one of ordinary skill in the art based on the present disclosure.

In some embodiments, as shown in FIG. 1B, a specific cell population can be labeled with a cell-permeable multifunctional probe that includes a succinimidyl ester group for covalent labeling of intracellular proteins and a chloroalkane ligand for covalent binding to a HaloTag® protein. The succinimidyl ester reacts non-specifically with exposed amines (e.g., of lysine residues) on cellular biomolecules (e.g., intracellular protein). The chloroalkane ligands are then displayed on the surface of such biomolecules. The pre-labeled cells can then be used to monitor a cell-specific response within a cell population (e.g., mixed cell population) or detect/image a biomolecule. If the labeled biomolecules release the cells, the chloroalkane ligand on the biomolecule becomes available for extracellular binding by a modified dehalogenase (e.g., HALOTAG). The dehalogenase-bound protein can be detected/imaged, and the rate or amount of biomolecule release from the labelled cell population can be monitored/quantitated. In some embodiments, the rate/amount of protein release from the cells provides a measure of the rate/amount of cell permeabilization and/or cell death.

In some embodiments, the capture agent (e.g. modified dehalogenase (e.g., HALOTAG) is linked to, or is provided as a fusion with, a detectable moiety. In some embodiments, the detectable moiety becomes detectable (or its signal is enhanced) when the capture agent binds to the probe-labeled biomolecule. In some embodiments, the detectable moiety becomes detectable (or its signal is enhanced) when two or more capture agents bind to capture elements located on adjacent or proximal sites on a biomolecule. For example, in certain embodiments herein, capture agents are provided as fusions with the multiple peptide/polypeptide components necessary to form a bioluminescent complex (e.g., via NanoBiT®, NanoLuc® multipartite components, or other multipartite technologies (U.S. Prov. Appln. Ser. No. 62/684,014; Intl. App. No. PCT/US19/36844; PCT Appln. No. PCT/US14/26354; and/or U.S. Pat. No. 9,797,889; herein incorporated by reference in their entireties)). When the capture agents bind to adjacent capture elements displayed on labeled proteins, a bioluminescent complex of the components is formed; the resulting bioluminescence provides a read-out for biomolecule release, cell permeabilization, and/or cell death. In some embodiments, the peptide/polypeptide components are incapable of efficiently forming the bioluminescent complex without facilitation (e.g., without being brought into proximity the dehalogenases they are fused to).

In some embodiments, the bifunctional probes and bioluminescent complexes of the present disclosure are used to measure cell death/apoptosis of a target cell population within a mixed cell culture. Biomolecules (e.g., proteins) within the target cells can be labeled with a cell-permeable multifunctional (e.g., bifunctional) probe. When the labeled proteins are released into the medium (e.g., protein escape), NanoBiT® components, NanoLuc® multipartite components, and/or components of a related multipartite technology fused to HaloTag® protein (components 1 and 2), bind the chloroalkane ligands on the biomolecule; when they are brought in close proximity, the active luciferase complex is generated. Upon addition of appropriate substrate (e.g., coelenterazine, a coelenterazine analog, NanoGlo®, etc.), the light generated is directly proportional to the amount of biomolecule released from dead cells. (FIG. 1A).

As depicted in FIG. 1B, in some embodiments the multifunctional (e.g., bifunctional) probe contains succinimidyl ester (SE) and chloroalkane (Cl) functional groups. When introduced into live cells, the succinimidyl ester moiety covalently attaches to free amino groups on biomolecules (e.g., intracellular proteins). When these labeled biomolecules are released from live cells upon cell death, they can be detected using a HaloTag® protein (modified halo-alkane dehydrogenase) that covalently binds the chloroalkane functional groups on proteins previously labeled with the bifunctional probe. In one embodiment, quantitative detection of released labeled biomolecules uses HaloTag®-SmBiT and HaloTag®-LgBiT fusion proteins. Detection is facilitated when two succinimidyl ester-chloroalkane ligands non-selectively bind to amino groups on a protein that are located in close proximity. The location of the two succinimidyl ester-chloroalkane ligands to the protein brings the HaloTag®-SmBiT component and the complementary HaloTag®-LgBiT component into sufficiently close proximity to produce a complementary bioluminescent peptide/polypeptide complex. In the presence of a luciferase substrate, light is produced in direct proportion to the amount of labeled protein released from the dead or dying cells, which is directly proportional to the number of dead or dying target cells. At a sufficiently high labeling density, bioluminescent complementation will occur to the extent necessary for sensitive detection.

Without limitation, target cells can include any cell from any source that is capable of being labeled using the materials and methods provided herein. In some embodiments, a target cell is derived from a patient. In some embodiments, a target cell is of a cell type that is commonly used in cell culture experiments and/or in a clinical setting. In some embodiments, a target cell is derived from a carcinoma, a sarcoma, a leukemia, a lymphoma, a multiple myeloma, a melanoma, a brain or spinal cord tumor, a germ cell tumor, a neuroendocrine tumor, or a carcinoid tumor. In some embodiments, a target cell is any cancerous or non-cancerous primary cell. In some embodiments, a target cell is a stem cell, or a cell derived from a stem cell, from a variety of difference sources, including, but not limited to, bone marrow, embryonic blastocysts or yolk sac, spleen, blood, including peripheral blood and umbilical cord blood, adipose tissue and other tissues and organs. In some embodiments, a target cell is a hematopoietic stem cell, an endothelial progenitor cell, an embryonic stem cell, or a mesenchymal stem cell.

The cell-permeable bifunctional probes of the present disclosure provide the ability to pre-label a certain cell type of interest, including, but not limited to, primary cells or cells isolated from patient samples without having to genetically engineering the cells. This type of specific call labeling allows one to follow the fate of the labeled cell population using a sensitive and quantitative bioluminescence approach. The changes can be measured as an end point or in real time using a convenient "add and read" format that is high-throughput and amenable to many different assay platforms.

Embodiments herein are not limited to the HALOTAG, SmBiT, and LgBiT components depicted in FIG. 1B. Rather, other capture agents (e.g., other modified dehalogenases (See, e.g., U.S. Pat. Nos. 7,238,842; 7,425,436; 7,429,472; 7,867,726; each of which is herein incorporated by reference in its entirety)) and complementary detection systems (e.g., other bipartite, tripartite, and multipartite bioluminescent complex systems (See, e.g., U.S. Prov. Appln. Ser. No. 62/684,014; Intl. App. No. PCT/US19/36844; PCT Appln. No. PCT/US14/26354; and/or U.S. Pat. No. 9,797,889; herein incorporated by reference in their entireties) also find use in embodiments herein. Capture reagents may also include fluorescent proteins or fragments or non-fluorescent subunits of fluorescent proteins that form a fluorescent moiety upon complementation. For example, fluorescent proteins or fragments or non-fluorescent subunits of fluorescent proteins can include those disclosed in Feng et al., (Nature Communications, vol. 8, "Improved split fluorescent proteins for endogenous protein labeling" (2017)), Foglieni et al., (Scientific Reports, vol. 7, "Split GFP technologies to structurally characterize and quantify functional biomolecular interactions of FTD-related proteins" (2017)), and Koraichi et a., (Journal of Cell Science, vol. 131, "High-content tripartite split-GFP cell-based assays to screen for modulators of small GTPase activation" (2018)).

As would be recognized by one of ordinary skill in the art based on the present disclosure, the methods and assays herein are capable of detecting any cellular response that leads, either directly or indirectly, to the release of an intracellular biomolecule from a cell and/or involves the detection of a biomolecule on the extracellular surface of a cell (a cell-associated biomolecule). In some embodiments, the cellular response occurs as a result of the cell itself responding to a physiological stimulus (e.g., apoptosis induced by a CART cell). In other embodiments, the cellular response occurs as a result of experimental manipulation to release a biomolecule from a cell (e.g., treatment with a cell permeabilizing agent). In some embodiments, biomolecule release or exposure can occur as a result of cell death, cytotoxicity, membrane permeabilization (e.g., caused by a small molecule, protein/peptide, or electrical stimulus), active transport mechanisms, an immune response, facilitated diffusion, and the like. In some embodiments, biomolecule release or exposure occurs via secretion of the biomolecule itself from the cell. In other embodiments, a biomolecule is released in a vesicle, including but not limited to, an exosome, a lysosome, a microvesicle, an extracellular vesicle and the like.

In some embodiments, the methods, assays, materials, and reagents herein find use in assays to determine the effectiveness of a particular treatment or therapy to kill disease cells (e.g., cancer cells, tumor cells, etc.). For example, methods are provided herein for assaying the sensitivity of biopsied tumor cells to chemotherapeutic. Methods are also provided for determining in vitro drug-sensitivity and/or chemosensitivity of a target cell type (e.g., within a mixed cell population). In some embodiments, biomolecules (e.g., protein) of a target population of cells are labeled with multifunctional reagent described herein. The labelled cells are subjected to a treatment or therapy, and the assays herein are used to monitor the effectiveness of the therapy in killing the target cells. In some embodiments, an assay uses patient-specific cells (e.g., obtained via biopsy) to determine the effectiveness of a treatment/therapy for a particular patient. In other embodiments, an assay uses a cell line or other model cell population to test the general effectiveness of a treatment/therapy. In some embodiments, the target cells are mixed and/or cultured with other non-labeled cells prior to administration of the treatment/therapy. In some embodiments, the assays herein allow for monitoring cell death of the target cells in the presence of other non-target cells (e.g., in cell culture, in situ, in vitro, etc.).

In some embodiments, the methods, assays, materials, and reagents herein find use in assays to determine the toxicity of a particular agent or condition on a cell population. For example, the toxicity of a particular chemical can be assayed to determine the safety of the chemical, the toxicity of a therapeutic/therapy can be assayed on a cell type that is adjacent to a treatment site (e.g., cells adjacent to a tumor) or that will be exposed to the therapeutic/therapy as a result of its administration to treat a disease or condition.

In some embodiments, the target cells may be of any suitable type that a researcher, clinician, or other user wishes to monitor the death of. Cells may be solid tumor cells (e.g., from cell culture, biopsied from a subject, etc.), non-solid cancer cells, non-cancer cells. Healthy human cells, cells from a model animal, a cell line, etc.

In some embodiments, the methods, assays, materials, and reagents herein find use in drug development. In some embodiments, potential drugs are tested against one or more cell types to determine their toxicity (e.g., against non-target cells) and/or their efficacy (e.g., in killing target cells). The methods herein are amenable to high-throughput assays, for example, for testing the capacity of a library of agents to kill cells. In some embodiments, one or more steps of the methods herein are carried out by a robotic or otherwise automated system.

In some embodiments, the methods, assays, materials, and reagents provided herein can be used to assess the efficacy of a potentially therapeutic treatment for a target cell (e.g., cancer cell). For example, an effector cell such as an effector B cell, an effector T cell (e.g., cytotoxic T lymphocyte), a natural killer (NK) cell, or a peripheral blood mononuclear cell (PBMC) can be co-cultured with pre-labeled tumor cells, and the ability of these effector cells to target the pre-labeled tumor cells can be assessed by measuring/ quantifying the bioluminescent signal produced upon activation of the effector cells (e.g., treatment with an antibody to induce ADCC) and subsequent lysis of the tumor cells (e.g., apoptosis). Representative results demonstrating these effects are provided in FIGS. 3-5 of the present disclosure. In accordance with these embodiments, the methods, assays, materials, and reagents provided herein can be used to identify novel therapeutic antibodies that facilitate ADCC in the target cells.

In some embodiments, assessing the efficacy of an effector cell for inducing apoptosis of a target cell can include obtaining target and/or effector cells directly from a subject as a potential basis for treatment (e.g., T cell therapy). For example, tumor cells from a subject can be pre-labeled with the multifunctional probes of the present disclosure and then co-cultured with T cells isolated from the patient. In some embodiments, the T cells are engineered to recognize the tumor cells (e.g., engineered to express chimeric antigen receptors (CARs) that bind to an antigen expressed on the surface of the tumor cell). Once co-cultured, the ability of the engineered T cell to target and lyse a tumor cell can be measured/quantified based on the amount of bioluminescent signal produced from the apoptotic tumor cells. In some embodiments, the T cells are not isolated from a subject but are isolated from heathy donors (e.g., allogenic T cell treatment). In accordance with these embodiments, the methods, assays, materials, and reagents provided herein can be used to identify novel therapeutic T cell treatments that can be used to target cancer cells in a subject.

5. KITS

Embodiments of the present disclosure also include kits comprising the various components described herein. Embodiments of the present disclosure can include a kit comprising a multifunctional probe (e.g., bifunctional probe, trifunctional probe, tetrafunctional probe, etc.) and one or more components of a bioluminescent complex (e.g., each component fused or linked to a capture agent). In some embodiments, the kit may also include a luminogenic substrate. A kit can include a container and/or instructions. A kit may also include at least one of a DNA molecule, an RNA molecule, a peptide, a polypeptide, a protein, or any combinations or derivatives thereof. In some embodiments, the kit includes a donor DNA template comprising a sequence encoding a peptide or polypeptide (e.g., HiBiT, LgBiT) or a modified dehalogenase protein (e.g., HALOTAG).

In some embodiments, the kit may include various detection reagents, including, but not limited to, a container comprising a multifunctional probe (e.g., bifunctional probe, trifunctional probe, tetrafunctional probe, etc.), a container comprising a first component of a bioluminescent complex (e.g., fused to a capture agent (e.g., HALOTAG), a container comprising a second component of a bioluminescent complex (e.g., fused to a capture agent (e.g., HALOTAG), and, in some cases, a container comprising a third component of a bioluminescent complex (e.g., fused to a capture agent (e.g., HALOTAG). In some embodiments, the components of the bioluminescent complex are provided to a single container or separate containers. The kit may also comprise a luminogenic substrate (e.g., Nano-Glo® Luciferase Assay Substrate) and digitonin. The kit may also include various buffers and other reagents required to perform a bioluminescence bioassay.

6. COMPONENT MODULARITY

Experiments conducted during development of embodiments herein, as well as previous research on several of the components of the assays, kits, etc. herein demonstrate that the modularity of the various components. For example, the biomolecule-reactive group (e.g., succinimidyl ester, a maleimide, an isocyanate, an isothiocyanate, a pentafluorophenyl ester, and a tetrafluorophenyl ester, etc.) may be attached (e.g., directly, by a variety of different linkers, etc.) to various capture agents (e.g., haloalkyl group). Similarly, the capture agent (e.g., HALOTAG or a structurally- or functionally-related dehalogenase) may be fused or tethered to various other components of the assays and kits herein (e.g., a bioluminescent polypeptide, a peptide or polypeptide components of a multipartite complementation systems (e.g., bipartite (e.g., NanoBiT®), tripartite (e.g., NanoTrip™), etc.), a fluorophore, etc. without altering the function of the capture agent. The peptide or polypeptide components of a multipartite complementation systems (e.g., bipartite (e.g., NanoBiT®), tripartite (e.g., NanoTrip™), etc.) can be fused or tethered to various other components, such as a fluorophore, a capture agent (e.g., HALOTAG or a structurally- or functionally-related dehalogenase), and antibody or antibody fragment, etc. which retaining the capacity to form an active bioluminescent complex.

In light of the modularity of the components described herein, any combinations of such components (e.g., as fusions, as tethered pairs, in a kit or assay together, etc.) is contemplated and within the scope herein.

In some embodiments, a kit comprises a multifunctional probe comprising a biomolecule-reactive group (e.g., succinimidyl ester, a maleimide, an isocyanate, an isothiocyanate, a pentafluorophenyl ester, and a tetrafluorophenyl ester, etc.) linked to a capture element (e.g., haloalkyl group); a capture agent (e.g., HALOTAG or a structurally- or functionally-related dehalogenase) fused to a polypeptide component of a bioluminescent complex; and a capture agent (e.g., HALOTAG or a structurally- or functionally-related dehalogenase) fused to a peptide component of a bioluminescent complex (e.g., a peptide that exhibits lower affinity for the polypeptide component (e.g., requires facilitation for complex formation); wherein the peptide and polypeptide components form the bioluminescent complex when brought into proper proximity/orientation with one another. In some embodiments, a kit further comprises a substrate for the bioluminescent complex. In some embodiments, an assay is provided that utilizes the aforementioned components.

In some embodiments, a kit comprises a multifunctional probe comprising a biomolecule-reactive group (e.g., succinimidyl ester, a maleimide, an isocyanate, an isothiocyanate, a pentafluorophenyl ester, and a tetrafluorophenyl ester, etc.) linked to a capture element (e.g., haloalkyl group); a capture agent (e.g., HALOTAG or a structurally- or functionally-related dehalogenase) fused to a polypeptide component of a bioluminescent complex; and fluorophore tethered to a peptide component of a bioluminescent complex (e.g., a peptide that exhibits hi affinity for the polypeptide component); wherein the peptide and polypeptide components form the bioluminescent complex upon co-localization. In some embodiments, a kit further comprises a substrate for the bioluminescent complex. In some embodiments, an assay is provided that utilizes the aforementioned components.

In some embodiments, a kit comprises a multifunctional probe comprising a biomolecule-reactive group (e.g., succinimidyl ester, a maleimide, an isocyanate, an isothiocyanate, a pentafluorophenyl ester, and a tetrafluorophenyl ester, etc.) linked to a capture element (e.g., haloalkyl group); a capture agent (e.g., HALOTAG or a structurally- or functionally-related dehalogenase) fused to a polypeptide component of a bioluminescent complex; and an antibody (or antibody fragment or other suitable specific binding moiety, aptamer, etc.) fused to a peptide component of a bioluminescent complex (e.g., a peptide that exhibits lower affinity for the polypeptide component (e.g., requires facilitation for complex formation); wherein the peptide and polypeptide components form the bioluminescent complex when brought into proper proximity/orientation with one another. In some embodiments, a kit further comprises a substrate for the bioluminescent complex. In some embodiments, an assay is provided that utilizes the aforementioned components.

In some embodiments, a kit comprises a multifunctional probe comprising a biomolecule-reactive group (e.g., succinimidyl ester, a maleimide, an isocyanate, an isothiocyanate, a pentafluorophenyl ester, and a tetrafluorophenyl ester, etc.) linked to a capture element (e.g., haloalkyl group); a capture agent (e.g., HALOTAG or a structurally- or functionally-related dehalogenase) fused to a first peptide component of a bioluminescent complex; a capture agent (e.g., HALOTAG or a structurally- or functionally-related dehalogenase) fused to a second peptide component of a bioluminescent complex; and a polypeptide component of he bioluminescent complex; wherein the first peptide, second peptide, and the polypeptide components form the bioluminescent complex when the capture agents bind to capture elements resulting in the peptide components being brought into proper proximity/orientation with one another. In some embodiments, a kit further comprises a substrate for the bioluminescent complex. In some embodiments, an assay is provided that utilizes the aforementioned components.

7. EXAMPLES

It will be readily apparent to those skilled in the art that other suitable modifications and adaptations of the methods of the present disclosure described herein are readily applicable and appreciable and may be made using suitable equivalents without departing from the scope of the present disclosure or the aspects and embodiments disclosed herein. Having now described the present disclosure in detail, the same will be more clearly understood by reference to the following examples, which are merely intended only to illustrate some aspects and embodiments of the disclosure and should not be viewed as limiting to the scope of the disclosure. The disclosures of all journal references, U.S. patents, and publications referred to herein are hereby incorporated by reference in their entireties.

The present disclosure has multiple aspects, illustrated by the following non-limiting examples.

Example 1

Compound Syntheses 4-((2-(2-(((6-chlorohexyl)oxy)ethoxy)ethyl)carbamoyl)benzoic Acid

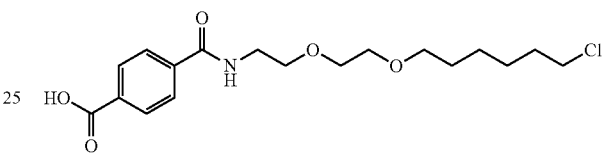

To a solution of terephthalic acid (2.97 g, 17.9 mmol) in anhydrous DMF (40 ml), diisopropyl ethylamine (12.5 ml, 71.5 mmol) followed by HATU (hexafluorophosphate azabenzotriazole tetramethyl uronium, 3.40 g, 8.94 mmol) was added. The solution was stirred for 10 min, and 2-(2-((6-chlorohexyl)oxy)ethoxy)ethan-1-amine (2.0 g, 8.94 mmol) was added slowly. The resulting reaction mixture was then stirred overnight. The solution was extracted with ethyl acetate and acetic acid solution (2M) and washed with brine. After dried over sodium sulfate, the organic solvent was evaporated, and the residue was purified by flash chromatography. $^1$H NMR (400 MHz, CDCl$_3$) δ 8.11 (m, 2H), 7.85 (m, 2H), 6.83 (s, 1H), 3.70-3.59 (m, 8H), 3.52-3.45 (m, 4H), 1.75-1.69 (m, 2H), 1.58-1.54 (m, 2H), 1.43-1.33 (m, 4H); MS m/z 371 [M+H].

2,5-dioxopyrrolidin-1-yl 4-((2-(2-(((6-chlorohexyl)oxy)ethoxy)ethyl)carbamoyl)benzoate

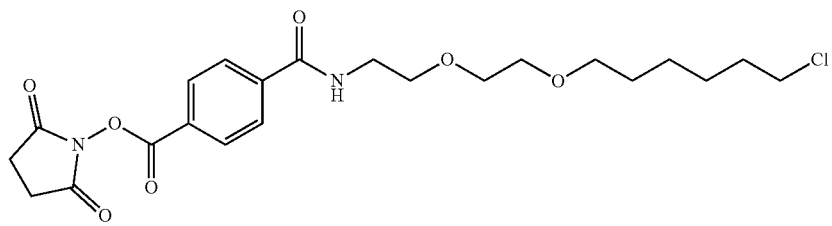 [SMILES: O=C(NCCOCCOCCCCCCCl)c1ccc(C(=O)ON2C(=O)CCC2=O)cc1]

To a solution of 4-((2-(2-(((6-chlorohexyl)oxy)ethoxy)ethyl)carbamoyl)benzoic acid (1.02 g, 2.76 mmol) in dichloromethane, diisopropyl ethylamine (0.96 ml, 5.51 mmol) was added. TSTU (N,N,N',N'-tetramethyl-O—(N-succinimidyl)uronium tetrafluoroborate, 0.91 g, 3.03 mmol) was subsequently added, and the reaction mixture was stirred for 20 min. The solvent was evaporated, and the residue was purified by flash chromatography. $^1$H NMR (400 MHz, DMSO) δ 8.84 (t, J=8.0 Hz, 1H), 8.20 (m, 2H), 8.08 (m, 2H), 3.62-3.54 (m, 6H), 3.50-3.43 (m, 4H), 3.38-3.30 (m, 2H), 2.91 (s, 4H), 1.71-1.64 (m, 2H), 1.49-1.42 (m, 2H), 1.39-1.22 (m, 4H); MS m/z 468 [M+H].

N2,N6-bis(4-((2-(2-(((6-chlorohexyl)oxy)ethoxy)ethyl)carbamoyl)benzoyl)lysine

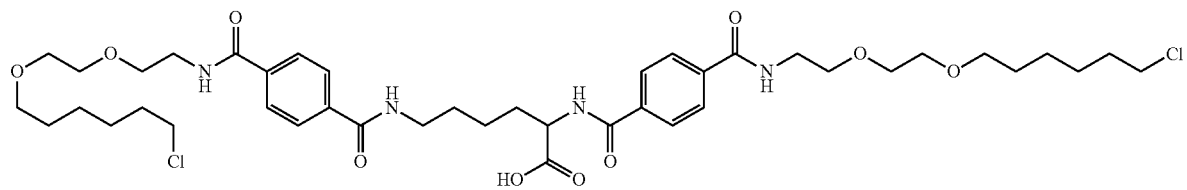 [SMILES: O=C(NCCCCC(NC(=O)c1ccc(C(=O)NCCOCCOCCCCCCCl)cc1)C(=O)O)c1ccc(C(=O)NCCOCCOCCCCCCCl)cc1]

To a solution of 2,5-dioxopyrrolidin-1-yl 4-((2-(2-(((6-chlorohexyl)oxy)ethoxy)ethyl)carbamoyl)benzoate (0.11 g, 0.23 mmol) in anhydrous DMF, diisopropyl ethylamine (0.09 g, 0.7 mmol) was added. L-lysine (0.017 g, 0.12 mmol) in PBS buffer (100 mM, pH 7.4) was subsequently added, and the reaction mixture was stirred overnight. The resulting solution was purified by preparative HPLC to give the product. MS m/z 854 [M+H].

2,5-dioxopyrrolidin-1-yl N2,N6-bis(4-((2-(2-(((6-chlorohexyl)oxy)ethoxy)ethyl)carbamoyl)benzoyl)lysinate

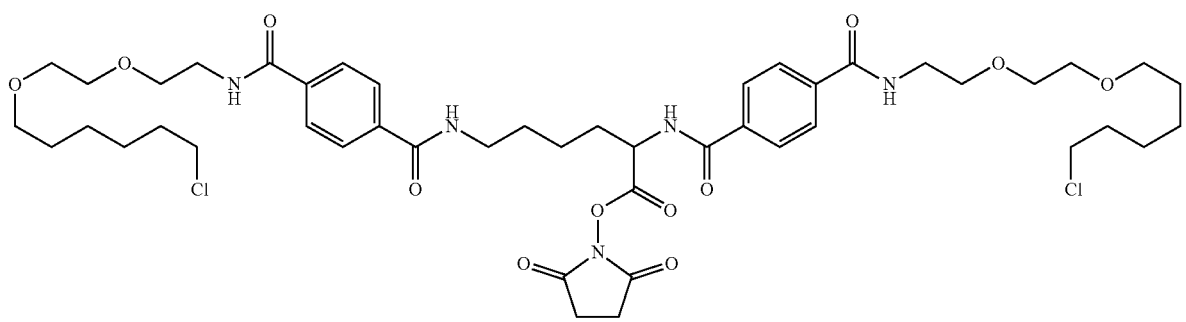 [SMILES: O=C(NCCCCC(NC(=O)c1ccc(C(=O)NCCOCCOCCCCCCCl)cc1)C(=O)ON1C(=O)CCC1=O)c1ccc(C(=O)NCCOCCOCCCCCCCl)cc1]

To a solution of N2,N6-bis(4-((2-(2-(((6-chlorohexyl)oxy)ethoxy)ethyl)carbamoyl)benzoyl)lysine (31 mg, 0.036 mmol) in anhydrous DMF, diisopropyl ethylamine (0.014 g, 0.11 mmol) was added. TSTU (N,N,N',N'-tetramethyl-O—(N-succinimidyl)uronium tetrafluoroborate, 0.013 g, 0.043 mmol) was subsequently added, and the reaction mixture was stirred for 20 min. The resulting solution was then purified by preparative HPLC to give the product. MS m/z 951 [M+H].

51

N-(4-aminobutylamino)-3-oxo-3H-spiro[isobenzofuran-1-9'-xanthene}-5-carboxamide

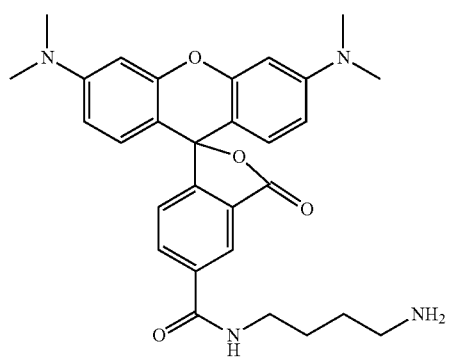 [SMILES: CN(C)c1ccc2c(c1)Oc1cc(N(C)C)ccc1C21OC(=O)c2cc(C(=O)NCCCCN)ccc21]

To a solution of 5-carboxytetramethylrhodamine (72.8 mg, 169.1 μmol) in anhydrous DMF (10 mL), diisopropyl ethylamine (60 μL, 338.2 μmol) was added. TSTU (N,N,N',N'-tetramethyl-O—(N-succinimidyl)uronium tetrafluoroborate, 56.01 mg, 186.0 μmol) was subsequently added, and the reaction mixture was stirred for 20 min. Diaminobutane (14.87 mg, 168.7 μmol) was slowly added, and the reaction mixture was allowed to stir for 20 mins. The reaction mixture was purified by prep-HPLC. MS m/z 501 [M+H].

52

$N^6$-(((9H-fluoren-9-yl)methoxy)carbonyl)-$N^2$-(4-(tert-butodycarbonyl)benzoyl)lysine To a solution of 4-(tert-butoxycarbonyl)benzoic acid (500 mg, 2.3 mmol) in anhydrous DMF (20 mL), TSTU (N,N,N',N'-tetramethyl-O—(N-succinimidyl)uronium tetrafluoroborate, 677.3 mg, 2.25 mmol) was added. Diisopropyl ethyl amine (883.8 μL, 6.75 mmol) was subsequently added slowly, and the reaction mixture was allowed to stir for 15 min. $N^6$-(((9H-fluoren-9-yl)methoxy)carbonyl)lysine (994.69 mg, 2.70 mmol) was added, and the resulting reaction mixture was then stirred overnight. The solution was extracted with ethyl acetate and washed with brine. After dried over sodium sulfate, the organic solvent was evaporated, and the residue was purified by flash chromatography. $^1$H NMR (400 MHz, DMSO) δ 12.62 (s, 1H), 8.72-8.79 (d, 1H), 7.98 (s, 4H), 7.84-7.91 (d, 2H), 7.64-7.71 (d, 2H), 7.36-7.41 (t, 2H), 7.26-7.35 (m, 3H), 4.32-4.42 (m, 1H), 4.23-4.31 (m, 2H), 4.15-4.23 (m, 1H), 3.18 (d, 2H), 1.71-1.88 (m, 2H), 1.57 (s, 9H), 1.35-1.50 (m, 3H), 1.34-1.14 (m, 1H); MS m/z 573 [M+H].

$N^2$-(4-(tert-butoxycarbonyl)benzoyl-$N^6$-(4-((2-(2-((6-chlorohexyl)oxy)ethoxy)ethyl)carbanmoyl)benzoyl)lysine

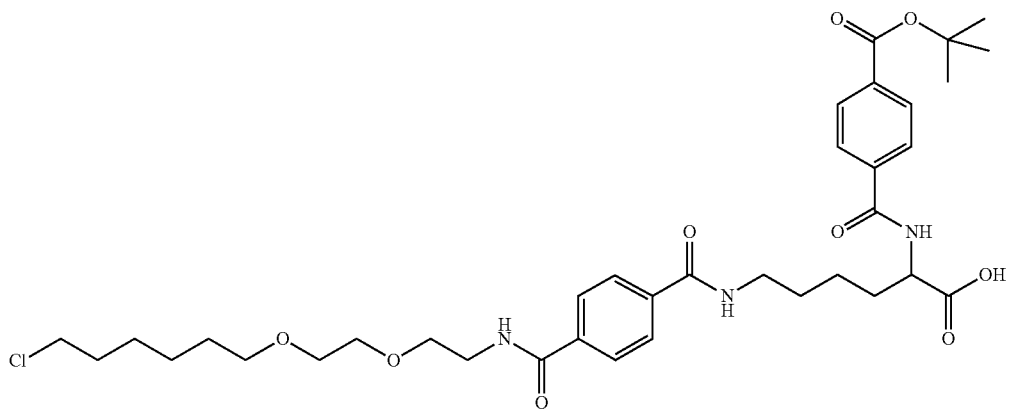 [SMILES: CC(C)(C)OC(=O)c1ccc(C(=O)NC(CCCCNC(=O)c2ccc(C(=O)NCCOCCOCCCCCCCl)cc2)C(=O)O)cc1]

To a solution of N⁶-(((9H-fluoren-9-yl)methoxy)carbonyl)-N²-(4-(tert-butodycarbonyl)benzoyl)lysine (599.0 mg, 1.05 mmol) in anhydrous DMF (10 mL), 3,4,6,7,8,9,10,10a-octahydropyrimido[1,2-a]azepine (625.7 µL, 4.18 mmol) was added. The reaction mixture was allowed to stir for 30 min. A separate solution of 2,5-dioxopyrrolidin-1-yl 4-((2-(2-((6-chlorohexyl)oxy)ethoxy)ethyl)carbamoyl)benzoate (490.5 mg, 1.05 mmol) in anhydrous DMF (2 mL) was subsequently added drop wise to the reaction mixture and was allowed to stir for 2 hr. The reaction mixture was purified using prep-HPLC. MS m/z 704 [M+H].

Tert-butyl 4-((1-((4-(3',6'-bis(dimethylamino)-3-oxo-3H-spiro[isobenzofuran-1-9'-xanthene]-5-carboxamido)butyl)amino)-6-(4-((2-(2-((6-chlorohexyl)oxy)ethoxy)ethyl)carbamoyl)benzamido)-1-oxohexan-2-yl)carbamoyl)benzoate

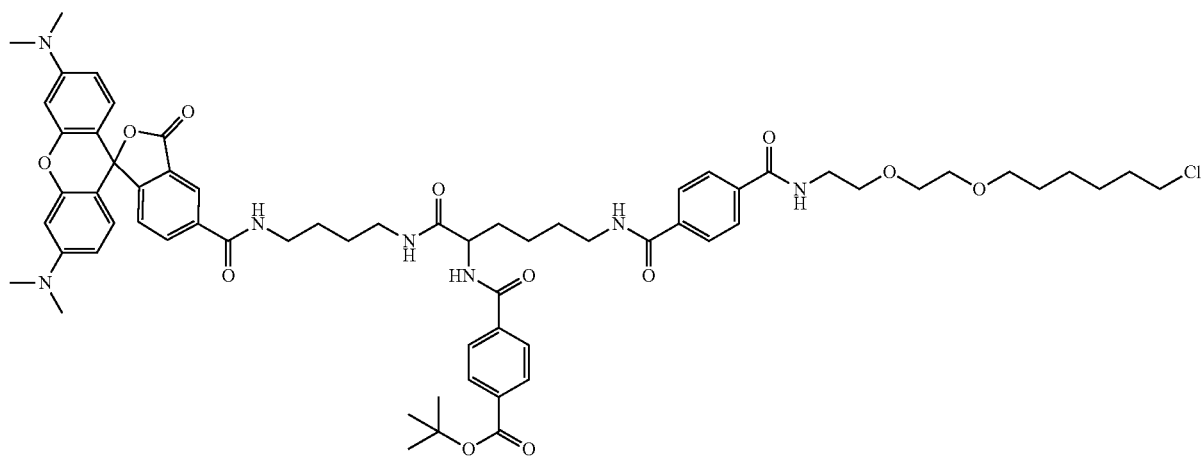 [SMILES: CN(C)c1ccc2c(c1)Oc1cc(N(C)C)ccc1C21OC(=O)c2cc(C(=O)NCCCCNC(=O)C(CCCCNC(=O)c3ccc(C(=O)NCCOCCOCCCCCCCl)cc3)NC(=O)c3ccc(C(=O)OC(C)(C)C)cc3)ccc21]

To a solution of N²-(4-(tert-butoxycarbonyl)benzoyl-N⁶-(4-((2-(2-((6-chlorohexyl)oxy)ethoxy)ethyl)carbanmoyl)benzoyl)lysine (44.0 mg, 62.48 µmol) in anhydrous DMF (10 mL), TSTU (N,N,N',N'-Tetramethyl-O—(N-succinimidyl)uronium tetrafluoroborate (20.7 mg, 68.7 µmol) was added. Diisopropyl ethyl amine (32.7 µL, 187.4 µmol) was subsequently added slowly, and the reaction mixture was allowed to stir for 20 min. N-(4-aminobutylamino)-3-oxo-3H-spiro[isobenzofuran-1-9'-xanthene}-5-carboxamide (31.28 mg, 62.5 µmol) was added, and the resulting reaction mixture was stirred for 1 hr. The reaction mixture was purified using prep-HPLC. ¹H NMR (400 MHz, MeOD₄) δ 8.54 (d, 1H), 8.04 (m, 1H), 8.01 (m, 1H), 7.99 (d, 1H), 7.90-7.97 (m, 2H), 7.85 (s, 4H), 7.32 (dd, 1H), 7.23 (d, 2H), 6.96-7.03 (m, 2H), 6.89-6.93 (m, 2H), 4.54 (dd, 1H), 3.63-3.74 (m, 5H), 3.55-3.63 (m, 5H), 3.52-3.55 (m, 2H), 3.45-3.51 (m, 5H), 3.41 (t, 2H), 3.29 (s, 12H), 1.82-2.06 (m, 2H), 1.64-1.80 (m, 9H), 1.58-1.63 (m, 11H), 1.48-1.58 (m, 5H), 1.28-1.48 (m, 5H); MS m/z 1187 [M+H].

4-((1-((4-(3',6'-bis(dimethylamino)-3-oxo-3H-spiro[isobenzofuran-1-9'-xanthene]-5-carboxamido)butyl)amino)-6-(4-((2-(2-((6-chlorohexyl)oxy)ethoxy)ethyl)carbamoyl)benzamido)-1-oxohexan-2-yl)carbamoyl)benzoic Acid

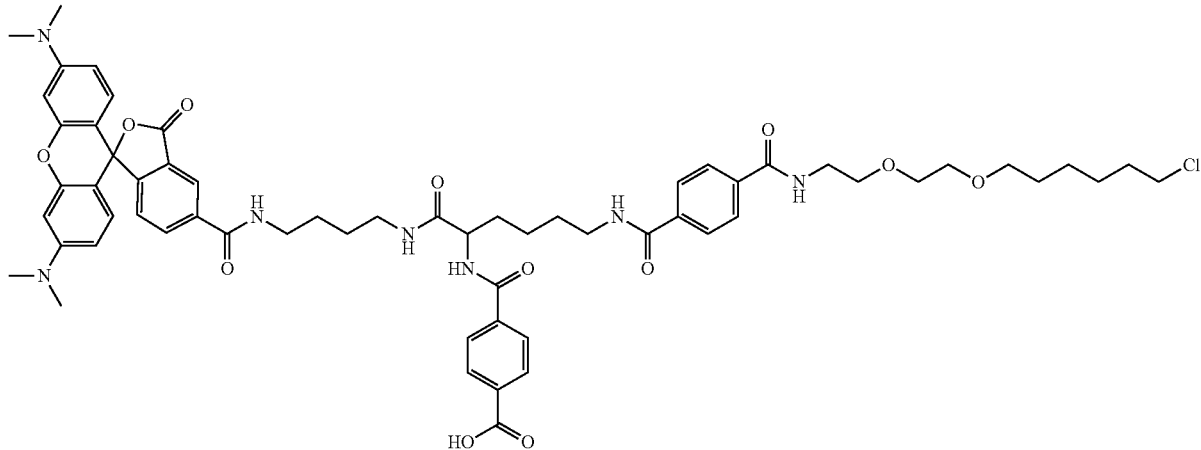 [SMILES: CN(C)c1ccc2c(c1)Oc1cc(N(C)C)ccc1C21OC(=O)c2cc(C(=O)NCCCCNC(=O)C(CCCCNC(=O)c3ccc(C(=O)NCCOCCOCCCCCCCl)cc3)NC(=O)c3ccc(C(=O)O)cc3)ccc21]

A solution of 1:1 TFA:DCM (6 mL) was prepared and tert-butyl 4-((1-((4-(3',6'-bis(dimethylamino)-3-oxo-3H-spiro[isobenzofuran-1-9'-xanthene]-5-carboxamido)butyl)amino)-6-(4-((2-(2-((6-chlorohexyl)oxy)ethoxy)ethyl)carbamoyl)benzamido)-1-oxohexan-2-yl)carbamoyl)benzoate was slowly added. The reaction mixture was allowed to stir for 40 min. The reaction mixture was concentrated and was allowed to dry overnight on a high vacuum. MS m/z 1130 [M+H].

2,5-dioxopyrrolidin-1-yl 4-((1-((4-(3',6'-bis(dimethylamino)-3-oxo-3H-spiro[isobenzofuran-1,9'-xanthene]-5-carboxamido0butyl)amino)-6-(4-((2-(2-((6-chlorohexyl)oxy)ethoxy)ethyl)carbomyl)benzamido)-1-1-oxohexan-2-yl)carbamoyl)benzoate To a solution of 4-((1-((4-(3',6'-bis(dimethylamino)-3-oxo-3H-spiro[isobenzofuran-1-9'-xanthene]-5-carboxamido)butyl)amino)-6-(4-((2-(2-((6-chlorohexyl)oxy)ethoxy)ethyl)carbamoyl)benzamido)-1-oxohexan-2-yl)carbamoyl)benzoic acid (7.7 mg, 6.8 μmol) in anhydrous DMF (2 mL), TSTU (N,N,N',N'-tetramethyl-O—(N-succinimidyl)uronium tetrafluoroborate (2.1 mg, 6.8 μmol) was added. Diisopropyl ethyl amine (2.4 μL, 13.6 μmol) was subsequently added slowly, and the reaction mixture was allowed to stir for 10 min. The reaction mixture was purified using prep-HPLC. $^1$H NMR (400 MHz, MeOD$_4$) δ 8.55 (d, 1H), 8.13-8.19 (m, 2H), 7.99-8.07 (m, 3H), 7.86 (d, 4H), 7.34 (d, 1H), 7.21-7.26 (d, 2H), 6.97-7.02 (dd, 2H), 6.93 (t, 2H), 4.60 (s, 1H), 3.63-3.73 (m, 9H), 3.52-3.62 (m, 9H), 3.40-3.52 (m, 9H), 3.37-3.39 (m, 3H), 3.14-3.16 (m, 2H), 2.93 (s, 4H), 1.65-1.78 (m, 7H), 1.47-1.60 (m, 3H), 1.28-1.47 (m, 12H), 1.07-1.11 (dd, 2H), 0.83-1 (m, 4H); MS m/z 1227.6 [M+H].

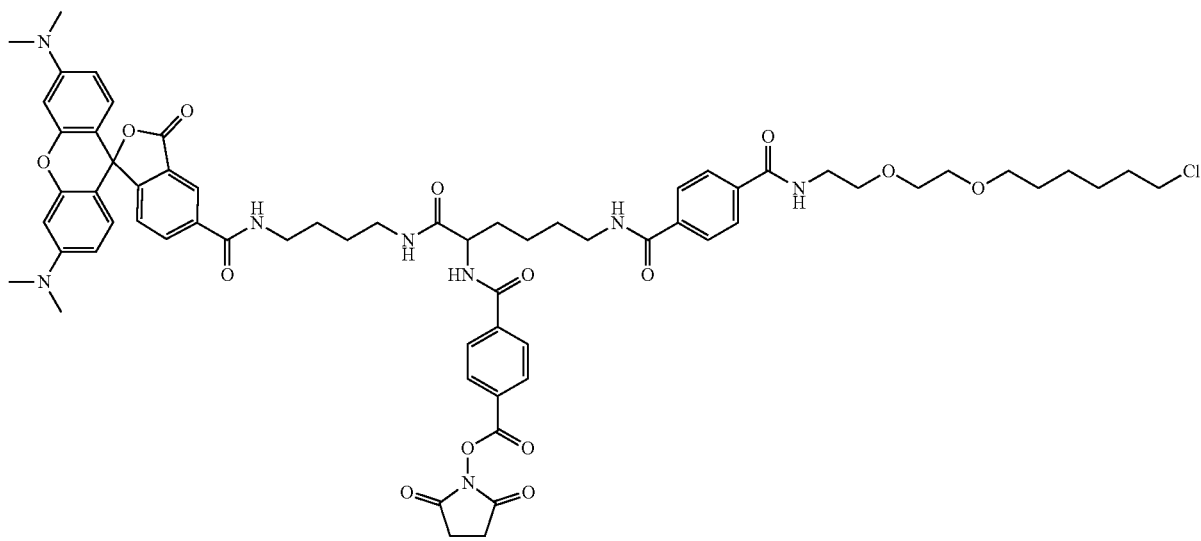 [SMILES: CN(C)c1ccc2c(c1)Oc1cc(N(C)C)ccc1C21OC(=O)c2cc(C(=O)NCCCCNC(=O)C(CCCCNC(=O)c3ccc(C(=O)NCCOCCOCCCCCCCl)cc3)NC(=O)c3ccc(C(=O)ON4C(=O)CCC4=O)cc3)ccc21]

Example 2

Methods for Cell Labeling and Detection

Generally, assay protocols include two parts: cell labeling and measuring release of labeled proteins from dead cells using a bioluminescence approach. In some embodiments, the cells can be labeled at a final probe concentration from 0.1-100 µM, and in some cases, 0.5-10 µM. The higher probe concentration generally increases labeling efficiency, but can lead to adverse effects in the cells. To achieve required assay performance (sensitivity, linearity, and assay window) without significant effect on cell physiology, labeling conditions, and assay set up should be optimized based on cell type and experimental conditions. Optimization examples are shown below in Table 1.

Next, the bifunctional labeling probe was thawed at room temperature and mixed. The probe was generally contained in DMSO. The bifunctional probe was added to the cells at a final concentration between about 0.5-10 µM. The cells were then mixed by gently pipetting and incubated for 30 minutes at 37° C. To inactivate unreactive free labeling probe, a 10× volume of pre-warmed (37° C.) cell culture medium containing 10% FBS was added, and the cells incubated for additional 5 minutes. The labeled cells were then spun down, and the labeling media removed. The cells were resuspended in fresh cell culture media at the concentration required for the experiment.

In some embodiments, one or more components of the NanoBiT® system can be used for measuring cell death of pre-labeled cell population in mixed cell cultures. Here, an exemplary protocol is described for using this assay in 96-well plates in 100 µL/well: 50 µl of sample+50 µl of Detection Reagent+25 µl of Nano-Glo® Luciferase Assay substrate.

Labeled cells (1,250-10,000 cells/well) were plated with experimental treatment conditions (e.g., drug, effector cells, etc.) in 50 µl of appropriate medium. Wells without cells were included as negative controls to determine background luminescence in the media. Separate wells were included with pre-labeled cells for determining maximum release of labeled proteins. Detection Reagents were assembled: about 1 ml of Detection Reagent buffer (2×) was combined with about 1.25 µl of Detection Component 1 and 1.25 µl of Detection Component 2. If maximum release determination was needed, the required amount of prepared Detection Reagent (50 µl/per sample) was removed, and digitonin at 0.12 mg/ml concentration added (for example, add 6 µl to 1 ml of Detection Reagent).

About 50 µl of prepared Detection Reagent was added into all assay wells and negative (media) control wells. Detection Reagent with Digitonin was added into control wells for determining maximum release. The cells were placed into a tissue culture incubator, and the treatment continued up to 24 hours. Nano-Glo® Luciferase Assay Substrate was prepared by diluting (1:50) substrate into assay medium. The assay plate was then removed from the tissue culture incubator and equilibrated to room temperature for about 5 mins. About 25 µL of prepared substrate was added to the assay wells, mixed, and luminescence was read.

Percent (%) cytotoxicity can be calculated using the following equation:

% Cytotoxicity=100×(Experimental RLUs−Medium Background)/(Maximum Cytotoxicity [digitonin control]−Medium Background)

Assay background and luminescence signal can vary in different media. The majority of experiments were performed using 10% serum. In the media without serum, in some cases, the background can be higher and addition of 0.1% BSA final concentration might reduce the background and increase assay window.

The nondestructive nature of the assays and methods described herein make them compatible with multiple other fluorescence and luminescence assays. Additionally, these assays and methods can be multiplexed with various viability/toxicity, for example CellTiter-Glo and LDH-Glo as well as other functional assays including flow analysis.

Most standard plate readers are designed for measuring luminescence and are suitable for the assays described herein. Some instruments do not require gain adjustment, while others might require optimizing the gain settings to achieve sensitivity and dynamic range. Opaque, white multi-well plates were generally used, which are compatible with a luminometer (e.g., Corning Costar® #3917 96-well or Costar® #3570 384-well plates). Light signal is diminished in black plates. Clear plates are not recommended for luminescence readout. The relative light output (RLU values) shown in the figures will vary depending on the plates and luminometers. However, if the signal is above machine background and within linear range of the instrument detection, it should not affect assay performance (calculated signal above assay background in live versus dead cells).

For assay optimization, labeling the cells at different probe concentrations and setting up cell titration curves can be advantageous. To evaluate effect of labeling on cell viability, different viability/toxicity assays can also be used. Here, an example of assay optimization is provided using Raji and K562 cells. As shown in Table 1, both Raji and K562 cells were labeled at 5 and showed increase in light output upon cell death. However, labeling efficiency, toxicity, assay linearity, and assay window differed depending on the cell line and labeling conditions. K562 cells showed more robust labeling at 5 µM as compared to 2 µM with assay linearity up to 5,000 cells/well. Labeling K562 at 2 µM extended linear range of the assay up to 20,000 cells/well, however assay window decreased from 18-fold to 7-8-fold. Importantly, no decrease in cell viability was measured with CellTiter-Glo, and the increase in light output within the linear range of the assay in live cells as compared to media control was less than 2-fold (general indication that the labeling is not toxic). Labeling Raji cells with 5 µM resulted in more than 40% decrease in cell viability as measured by CellTiter-Glo (data not shown) that also corresponded to significant increase in luminescence signal in live cells as compared to media control (>2-fold increase from media only control). Decreasing labeling concentration to 1 µM allowed to label Raji cells with acceptable assay window above >5-fold and linearity for up to 20,000 cells/well without significant effect on cell viability.

For assay optimization, labeling the cells at different probe concentrations and setting up cell titration curves can be advantageous. To evaluate effect of labeling on cell viability, different viability/toxicity assays can also be used. Here, an example of assay optimization is provided using Raji and K562 cells. As shown in Table 1, both Raji and K562 cells were labeled at 5 µM and showed increase in light output upon cell death. However, labeling efficiency, toxicity, assay linearity, and window differed depending on the cell line and labeling conditions. K562 cells showed more robust labeling at 5 µM as compared to 2 µM with assay linearity up to 5,000 cells/well. Labeling K562 at 2 µM extended linear range of the assay up to 20,000 cells/well, however assay window decreased from 18-fold to 7-8-fold. Importantly, no decrease in cell viability was measured with CellTiter-Glo, and the increase in light output within the linear range of the assay in live cells as compared to media control was less than 2-fold (general indication that the labeling is not toxic). Labeling Raji cells with 5 µM resulted in more than 40% decrease in cell viability as measured by CellTiter-Glo (data not shown) that also corresponded to significant increase in luminescence signal in live cells as compared to media control (>2-fold increase from media only control). Decreasing labeling concentration to 1 µM allowed to label Raji cells with acceptable assay window above >5-fold and linearity for up to 20,000 cells/well without significant effect on cell viability.

TABLE 1

Assay optimization for K562 and Raji cells.

| Probe | | Cells/well | 0 | 1,250 | 2,500 | 5,000 | 10,000 | 20,000 |
|---|---|---|---|---|---|---|---|---|
| K562 | 2 µM | Live, RLUs | 34,252 | 37,113 | 40,600 | 42,059 | 47,861 | 51,528 |
| | | Dead, RLUs | 55,243 | 69,663 | 88,448 | 114,346 | 154,018 | 192,283 |
| | | Dead/Live | | 5.0 | 5.2 | 7.6 | 7.3 | 7.9 |
| | 5 µM | Live, RLUs | 33,155 | 43,298 | 50,284 | 60,873 | 76,596 | 78,093 |
| | | Dead, RLUs | 52,887 | 236,022 | 373,598 | 591,060 | 620,751 | 477,185 |
| | | Dead/Live | | 18.1 | 18.7 | 19.4 | 13.1 | 9.4 |
| Raji | 1 µM | Live, RLUs | 63,897 | 71,937 | 78,455 | 88,466 | 107,531 | 134,572 |
| | | Dead, RLUs | 64,915 | 112,901 | 164,403 | 257,879 | 403,731 | 731,355 |
| | | Dead/Live | | 6.0 | 6.8 | 7.9 | 7.8 | 9.4 |
| | 5 µM | Live, RLUs | 60,321 | 210,695 | 317,452 | 508,581 | 672,232 | 645,489 |
| | | Dead, RLUs | 63,422 | 1222,161 | 2,179,562 | 3,826,655 | 4,916,472 | 3,314,700 |
| | | Dead/Live | | 7.7 | 8.2 | 8.4 | 7.9 | 5.6 |

As shown in Table 1, K562 and Raji cells were labeled at different probe concentrations. No labeling control was included for toxicity evaluation. After labeling, the cells were resuspended in appropriate medium, counted, and plated into wells of a 96-well plate at two-fold serial dilution starting from 20,000 cells/well. The Detection Reagents with or without digitonin were added as described above, and the plates were placed into a tissue culture incubator. After incubation, Nano-Glo® Luciferase Assay substrate was added to the samples, and luminescence was read. After reading luminescence, an equal volume of CellTiter-Glo was added to the samples to measure changes in viability. Data show raw relative light units (RLU) in live and dead (digitonin treated cells) at different cell densities. The linear range of the assay is underlined. Dead/Live is the ratio between luminescence signal of dead and live cells calculated after assay background subtraction (media control).

TABLE 2

Labeling concentrations and example signal windows for different cells.

| Cell Type | Final Labeling Probe Concentration | Dead/Live at 5,000 cells/well |
|---|---|---|
| Raji | 2 µM | 35.4 at 4 h/21.7 at 24 h |
| SKBR3 | 10 µM | 10.1 at 4 h/10.9 at 24 h |
| HCT116 | 10 µM | 8.1 at 4 h/6.7 at 24 h |
| K562 | 5 µM | 18.3 at 4 h/19.0 at 24 h |
| A431 | 10 µM | 7.4 at 4 h/6.2 at 24 h |

Example 3

Bioluminescent Detection of Cells Labeled with Bifunctional Probes

Figure 2B:
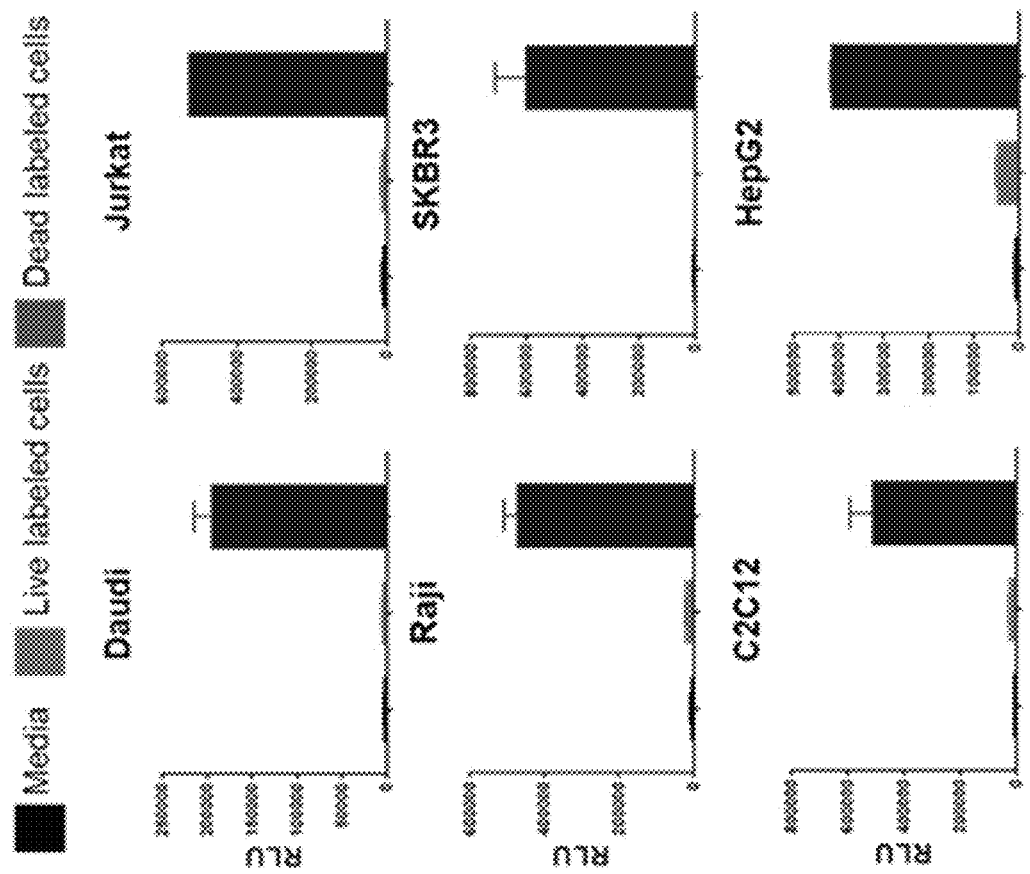
FIGS. 2A-2B include a representative schematic diagram of a method of labeling target cells with the multifunctional probes of the present disclosure (FIG. 2A) and results of experiments conducted to detect bioluminescence in various cell types labeled with the multifunctional probes (FIG. 2B).
Figure 2A:
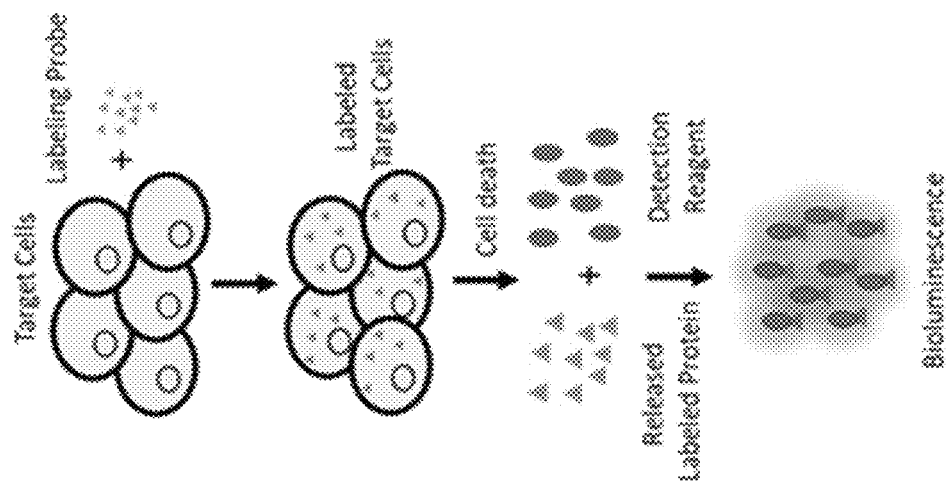

As shown in FIGS. 2A-2B, a variety of cells were labeled with the bifunctional probes of the present disclosure. FIG. 2A is a representative schematic diagram of a method used to label the various target cells identified in FIG. 2B. As shown in FIG. 2B, the cell permeable bifunctional probes of the present disclosure (SE-Cl probes) were successfully taken up by every cell tested. Robust luminescence was detected from the labeled proteins released after cell death, which were quantified using the NanoBiT® system, while little luminescence was detected in the media and live cells.

In accordance with these experiments, the various cell types tested were collected by centrifugation for 5 mins at 300 g followed by aspiration of the media and resuspension in PBS. The bifunctional probe was then added to the media and allowed to incubate for 30 mins at 37° C. Pre-warmed (37° C.) complete media containing 10% serum was then added to the cells and incubated for 5 mins at 37° C. The labeled cells were then collected by centrifugation for 5 mins at 300 g and excess media was removed, and the labeled cells were then resuspended in the desired media. NanoBiT® detection reagents were then added to the labeled cells and allowed to incubate for 30 mins at 37° C. prior to reading luminescence (RLUs).

Example 4

Bifunctional Probes to Test Antibody Dependent Cellular Cytotoxicity

As shown in FIGS. 3A-3C, experiments were conducted to test antibody dependent cellular cytotoxicity (ADCC) in Daudi (FIGS. 3A-3B) and SKBR3 (FIG. 3C) cells labeled with the bifunctional probes of the present disclosure. Daudi and SKBR3 cells were labeled with 1 µM and 10 µM Labeling Probe respectively and co-cultured with peripheral blood mononuclear cells (PBMC; Cellular Technologies Limited) at an E:T ratio of 20:1 (100,000 effector to 5,000 target) with indicated antibody titrations for 5 hours at 37° C. prior to Nano-Glo® Luciferase Assay Substrate addition. FIG. 3A shows average raw relative light units (RLU) for assay background (media+detection), labeled target cells only (T), labeled target cells mixed with effector cells (T+E), T+E with Rituximab, and maximal release (MR). Curves in FIGS. 3B and 3C were generated following assay background subtraction (RLU [Target cells+Effector cells+Detection Components]–RLU [Media+Detection Components]) using a four parametric variable slope algorithm in Prism. Calculated EC50 values were 6.8 ng/mL and 0.11 μg/mL for Rituximab and Herceptin respectively.

Example 5

Bispecific T-Cell Engager (BiTE) Assays

Figure 4:
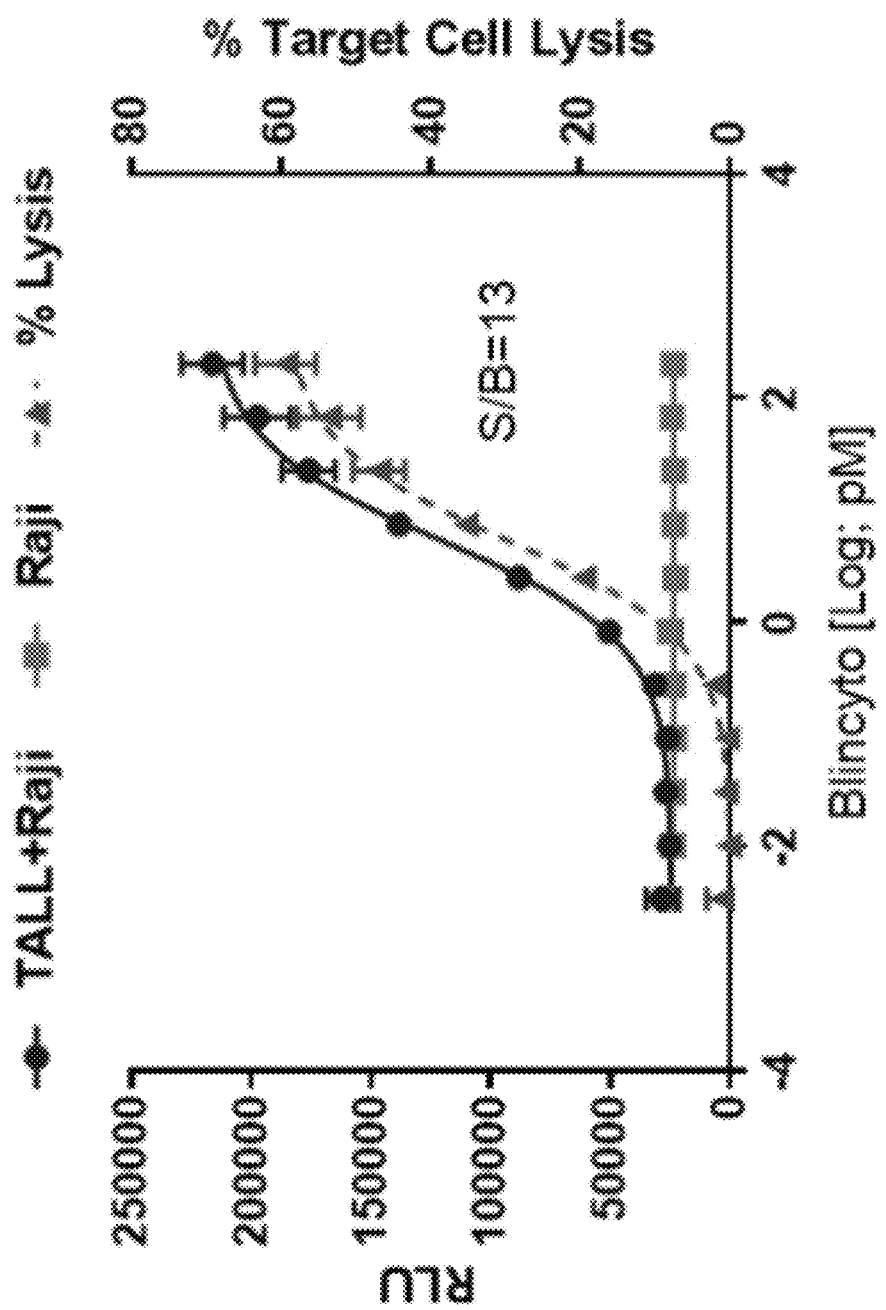
FIG. 4 shows representative results of experiments conducted to test target cell lysis using bispecific T-cell engagers (BiTE) in cells labeled with multifunctional probes and detected using the bioluminescent detection components

As shown in FIG. 4, experiments were conducted to test target cell lysis using bispecific T-cell engagers (BiTE) in cells labeled with bifunctional probes and detected using the bioluminescent detection components. BiTEs are a class of artificial bispecific monoclonal antibodies that are investigated for the use as anti-cancer drugs as they are used to direct the T cells' cytotoxic activity to target cells (e.g., cancer cells). As shown, Raji target cells (1.67 μM Labeling probe) and TALL-104 effector cells were co-cultured at 2.5:1 ratio (12,500 effector to 5,000 target) in a 96-well assay plate. Bincyto was titrated at indicated concentrations and assay plate was incubated for 6 hours at 37° C. prior to Nano-Glo® Luciferase Assay Substrate addition. Curves were generated following assay background subtraction as described in above. EC50=5.38 μM. S/B=BiTE/no BiTE. % antibody dependent target cell lysis=100×(RLU [target+effector+antibody]–RLU [target+ effector])/(RLU [target+effector+digitonin]–RLU [target+ effector]).

Example 6

ADCC Assay Kinetics

Figure 5:
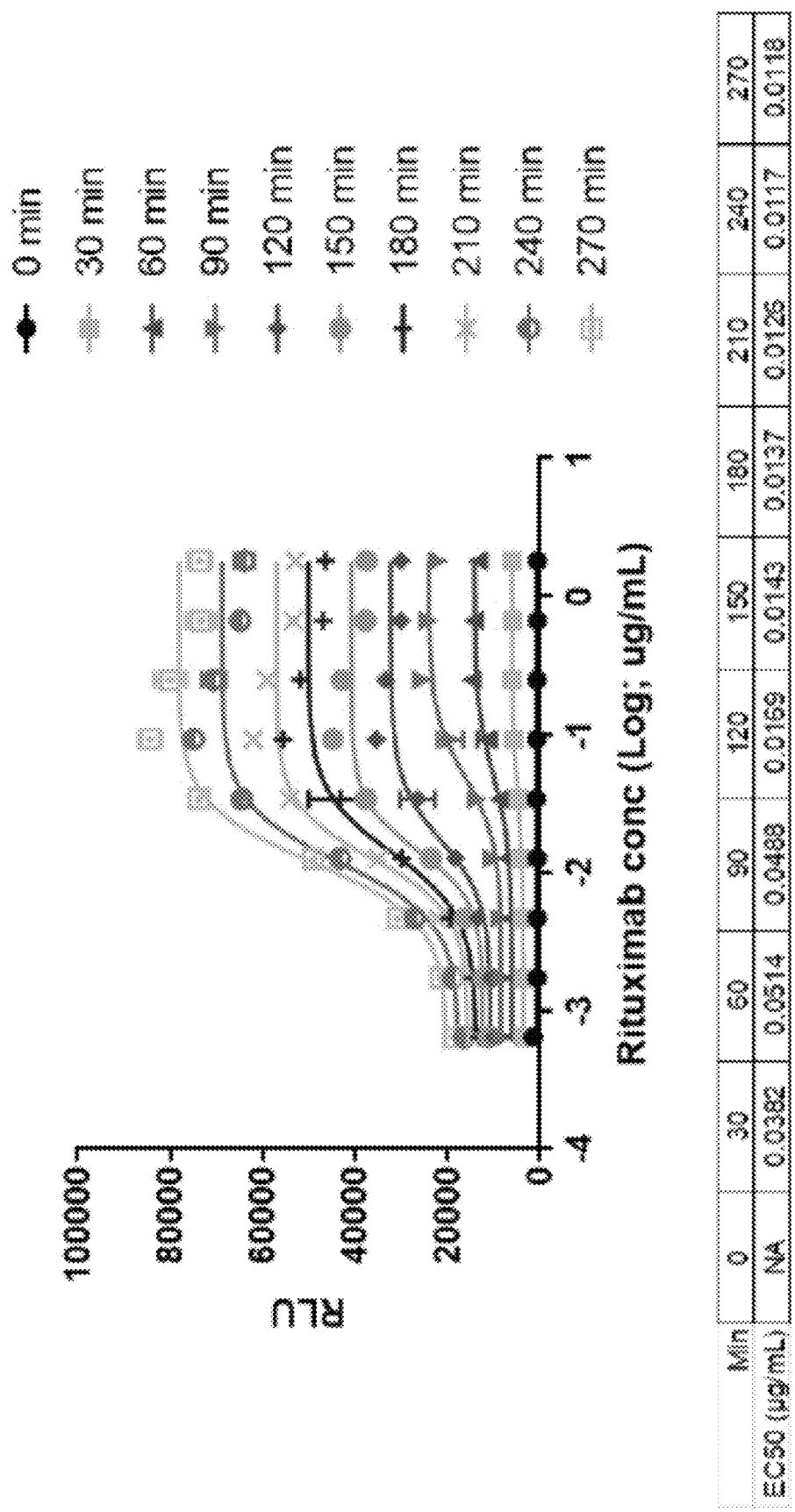
FIG. 5 shows representative results of experiments conducted to test antibody dependent cellular cytotoxicity (ADCC) kinetics in Daudi cells labeled with multifunctional probes and detected using bioluminescent detection components (co-cultured with PBMCs).

As shown in FIG. 5, experiments were conducted to test antibody dependent cellular cytotoxicity (ADCC) kinetics in Daudi cells labeled with bifunctional probes and detected using bioluminescent detection components (co-cultured with PBMCs). Labeled Daudi were co-cultured with PBMCs (Cellular Technologies Limited) at an E:T ratio of 20:1 (100,000 effector to 5,000 target) with indicated antibody titrations in the presence of NanoGlo® Vivazine™ Live Cell substrate. The assay plate was incubated at 37° C. and read at indicated times. Curves were generated following using a four parametric variable slope algorithm in Prism without background subtraction.

Example 7

Cell Death Assays

Figure 6A:
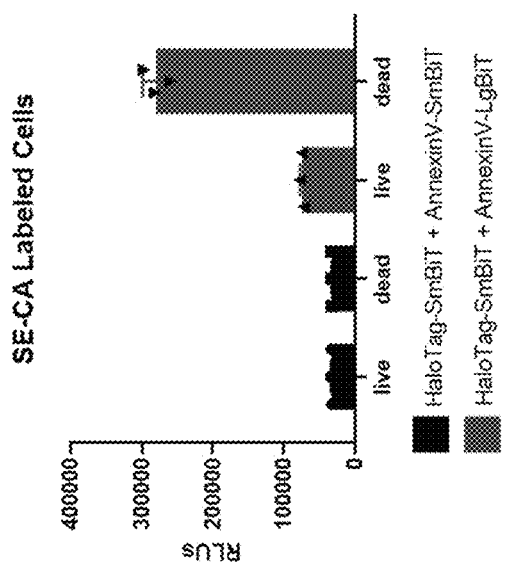
FIGS. 6A-6B include representative schematic diagrams depicting the use of multifunctional probes of the present disclosure to assess cell death based on endogenous phosphatidyl serine (PS) translocation (FIG. 6A), and representative results from cells using complementary and non-complementary bioluminescent components (FIG. 6B).
Figure 6B:
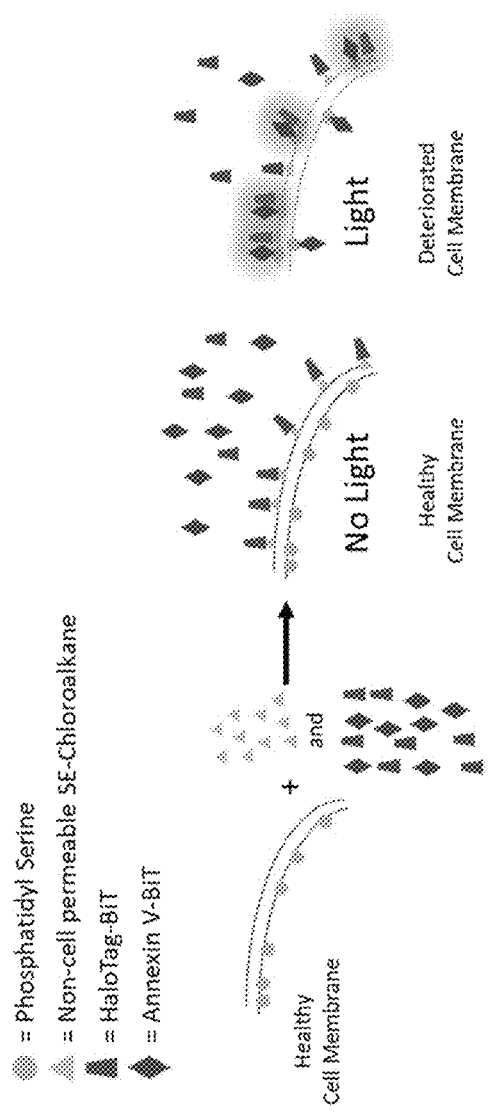

As shown in FIGS. 6A-6B, the multifunctional probes of the present disclosure can be used to detect and/or quantify various cellular responses, including, for example, cell death based on endogenous phosphatidyl serine (PS) translocation (FIG. 6A). Cells are labeled with a multifunctional probe and mixed with HALOTAG-BiTs and complementary AnnexinV-BiTs. In healthy cells, HALOTAG-BiTs bind exposed chloroalkane (CA) ligands (labeled biomolecules) on the extracellular surface of the cells, whereas the PS remains unbound by the AnnexinV-BiTs. In unhealthy cells, however, PS is translocated to the outer leaflet of the cell membrane and is able to be bound by the AnnexinV-BiTs, thus indicating early stages of apoptosis. As the cell membrane begins to degrade and gaps are created, the AnnexinV-BiTs can enter the cell and bind to PS on the inner leaflet. When two complementing BiT partners are within functional proximity (e.g., AnnexinV-LgBiT and HHALOTAG-SmBiT), a luminescent signal is generated. FIG. 6B includes representative data in live and dead SE-CA labeled cells using non-complementary (first and second bars from the left) and complementary (third and fourth bars from the left) BiT pairs. These results demonstrate the ability of the multifunctional probes of the present disclosure to differentiate among cell populations based on a physiologically relevant responses.

Example 8

Dual Fluorescence and Luminescence Detection

As shown in FIGS. 7A-7B, experiments were conducted to detect both fluorescence and luminescence using the multifunctional probes of the present disclosure. In this embodiment, cells were labeled with multifunctional chloroalkane probe at the indicated concentrations and detected using HALOTAG-HiBiT (high affinity) and LargeBiT (LgBiT) tagged with a fluorophore, Dy605 (red). FIG. 7A includes representative fluorescence images of cells stained with LgBiT-Dy605 (upper row) or HALOTAG-HiBiT+LgBiT-Dy605 (lower row). Cell nuclei were co-stained with Hoechst (blue). FIG. 7B includes representative quantitative data corresponding to luminescence relative light units.

Example 9

Dual Fluorescence and Luminescence Detection

The following example used a cell permeable bifunctional maleimide-chloroalkane labeling probe, PBI-8158. Rather than binding to free amines as with the other probes disclosed previously, this probe irreversibly binds to Thiol groups. Proteins in cells are labeled with the probe, and the release of protein-bound probe is detected using HALOTAG-BiTs.

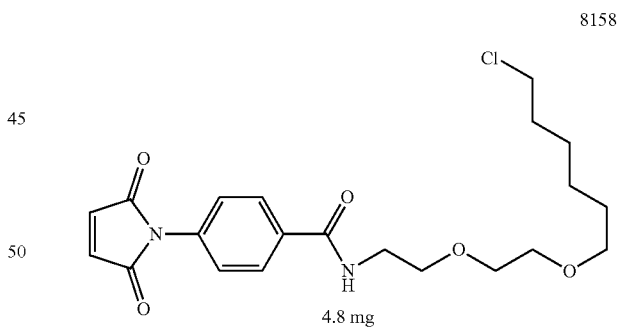

8158

4.8 mg

Figure 8A:
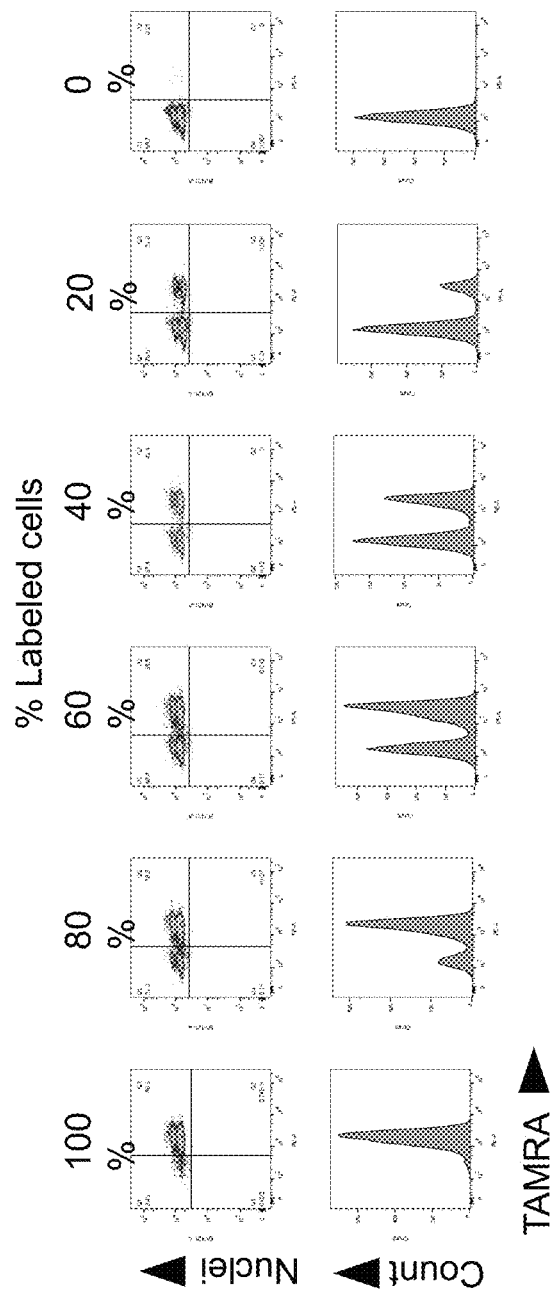
FIGS. 8A-8B include representative results of cellular thiol groups labeled using a maleimide ligand containing a chloroalkane linker for HALOTAG binding. Labeled cells were mixed with unlabeled cells in indicated percentages and detected using HALOTAG-HiBiT and TAMRA conjugated LgBiT. Representative dot blots (upper; y axis=nuclei+, x axis=TAIVIRA+) and histograms (lower; y axis=cell count, x axis=TAMRA+) measured by flow cytometry (FIG. 8A). An XY plot comparing predicted % labeled cells (x-axis) and measured % labeled cells (y-axis) (FIG. 8B).
Figure 8B:
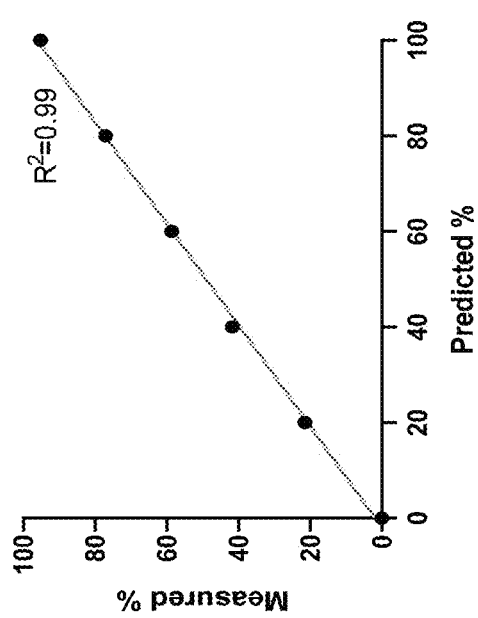

For this experiment, labeled and unlabeled cells were mixed at varying percentages (100, 80, 60, 40, 20, and 0%) to test whether a fraction of labeled cells could be detected in a mixed population using flow cytometry. Mixed cells were fixed with 4% paraformaldehyde followed by permeabilization with PBS containing 0.1% triton. The permeabilization step allows for the BiTs to enter the cell. HALOTAG-HiBiT was added to the cells to bind the chloroalkane linker for 2 hours at 37° C. Cells were subsequently washed with PBS containing 0.1% Tween20 (PBST) to remove unbound HiBiT. LgBiT conjugated to TAMRA was added to the cells and incubated for 30 minutes at room temp followed by washing with PBST. Nuclei were stained using Hoechst (1:2500 in PBS). Single cells positive for Hoechst were gated, and TAMRA positive cells were detected using a BD LSR Fortessa cytometer. FIG. 8 includes representative results of cellular thiol groups labeled using a maleimide ligand containing a chloroalkane linker for HALOTAG binding.

Example 10

Detection in Pre-Labeled Cells in 3D Cultures

Figure 9:
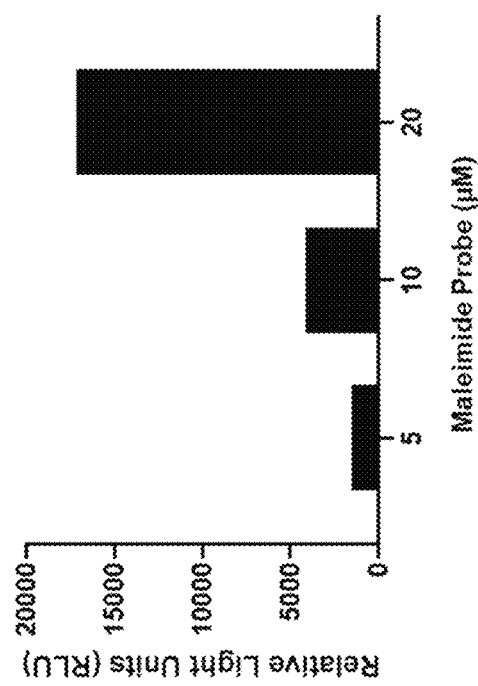
FIG. 9 shows relative light units generated by hepatic spheroids labeled with 5, 10, and 20 μM of maleimide/chloroalkane bifunctional probe in the presence of HALOTAG-SmBiT and HALOTAG-LgBiT.

Primary hepatocytes were collected and pre-labeled with a bifunctional probe containing a maleimide moiety coupled with a chloroalkane linker for binding HALOTAG protein. Hepatic spheroids were formed over a period of 7 days in ultralow attachment 96-well tissue culture plates. After 7 days, the medium was removed, and the spheroids were fixed using 4% paraformaldehyde. Hepatic spheroids were subsequently permeabilized using PBS containing 0.1% Triton X-100 following by three washes in PBS containing 0.1% bovine serum albumin (BSA). For detection, HALOTAG-SmBiT and HALOTAG-LgBiT (50 nM each in PBS containing 0.1% BSA) were added to the labeled spheroids. After a 2-hour incubation at 37° C., the Nano-Glo® Live Cell Assay System was added, and the plate was read using a GloMax® luminometer at 0.5 second integration. Data shown in FIG. 9 are relative light units generated by hepatic spheroids labeled with 5, 10, and 20 µM bifunctional probe.

Example 11

Detection of Pre-Labeled Live Cells Using HALOTAG-LgBiT and HALOTAG-SmBiT

Figure 10:
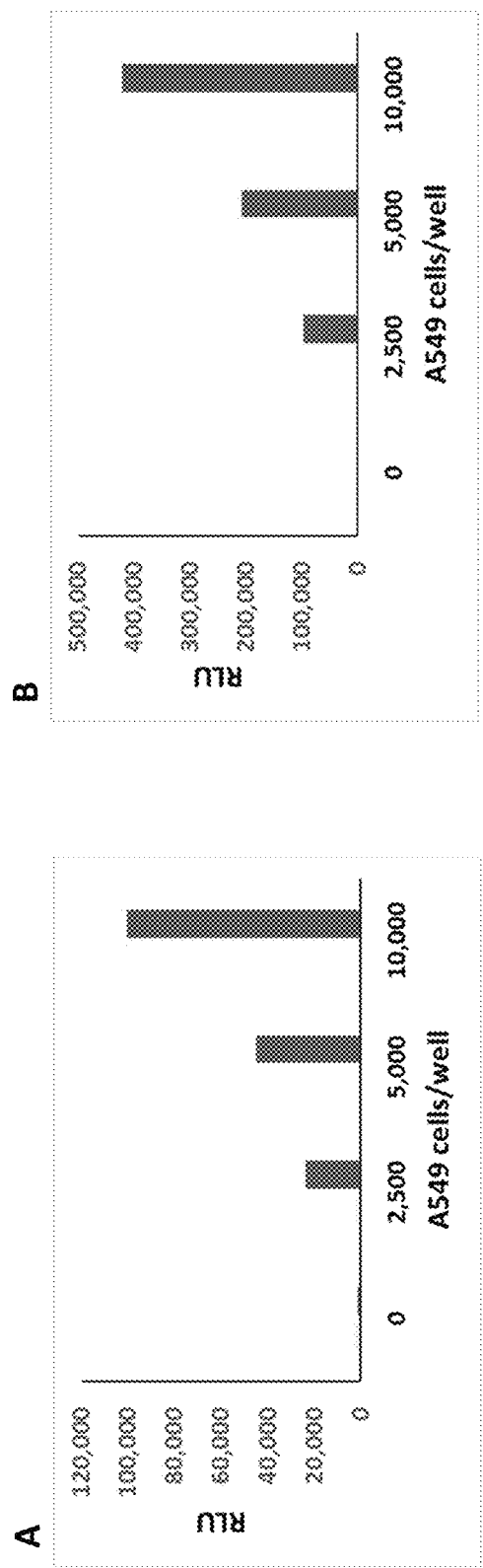
FIG. 10 shows relative light units in the presence of HALOTAG-SmBiT and HALOTAG-LgBiT, generated at different densities of A549 control (not labeled) cells (light bars) or cells pre-labeled with bifunctional probes (dark bars).

A549 cells were collected and pre-labeled with a bifunctional probe containing a succinimidyl ester group (A) or a maleimide moiety (B) coupled with a chloroalkane linker for binding HaloTag protein. After media removal and washing, live cells were fixed using 4% paraformaldehyde and subsequently permeabilized using PBS containing 0.1% Triton X-100. For detection, HALOTAG-SmBiT and HALOTAG-LgBiT (200 nM each in PBS containing 0.1% BSA) were added to the labeled cells. After a 2-hour incubation at 37° C., the Nano-Glo® Live Cell Assay System was added, and the plate was read using a GloMax® luminometer at 0.5 second integration. Data in FIG. 10 show relative light units generated at different densities of A549 control (not labeled) cells (light bars) or cells pre-labeled with bifunctional probes (dark bars).

Example 12

Detection of Pre-Labeled Live Cells Using HALOTAG-LgBiT and Antibodies to Specific Cellular Protein Pre-Labeled with SmBiT In this Example, HALOTAG-LgBiT binds to exposed chloroalkane ligand on labeled targets. When antibodies to specific cellular protein pre-labeled with SmBiT bind to that protein in the close proximity of HALOTAG-LgBiT, a luminescent signal is generated.

Figure 11:
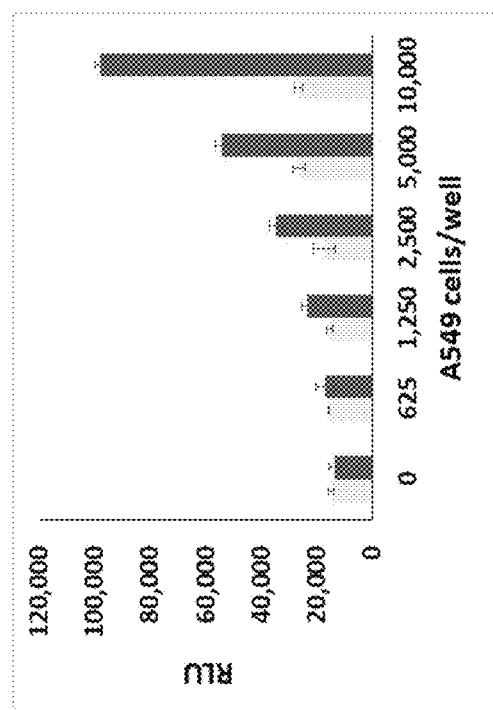
FIG. 11 shows relative light units in the presence of HALOTAG-LgBiT and anti-LDH antibodies pre-labeled with HALOTAG-SmBiT, generated at different densities of A549 control (not labeled) cells (light bars) or cells pre-labeled with bifunctional probes (dark bars)

A549 cells were collected and pre-labeled with a bifunctional probe containing a maleimide moiety coupled with a chloroalkane linker for binding HALOTAG protein. After media removal and washing, live cells were fixed using 4% paraformaldehyde and subsequently permeabilized using PBS containing 0.1% Triton X-100. For detection, HALOTAG-LgBiT (200 nM) and anti-LDH antibodies pre-labeled with HALOTAG-SmBiT (2 ug/ml) were added to the labeled cells. After a 2-hour incubation at 37° C., the Nano-Glo® Live Cell Assay System was added and the plate was read using a GloMax® luminometer at 0.5 second integration. Data in FIG. 11 show relative light units generated at different densities of A549 control (not labeled) cells (light bars) or cells pre-labeled with bifunctional probes (dark bars).

SEQUENCES

WT OgLuc (SEQ ID NO: 1):
MFTLADFVGDWQQTAGYNQDQVLEQGGLSSLFQALGVSVTPIQKVVLSGE

NGLKADIHVIIPYEGLSGFQMGLIEMIFKVVYPVDDHHFKIILHYGTLVI

DGVTPNMIDYFGRPYPGIAVFDGKQITVTGTLWNGNKIYDERLINPDGSL

LFRVTINGVTGWRLCENILA

WT OgLuc Lg (SEQ ID NO: 2):
MFTLADFVGDWQQTAGYNQDQVLEQGGLSSLFQALGVSVTPIQKVVLSGE

NGLKADIHVIIPYEGLSGFQMGLIEMIFKVVYPVDDHHFKIILHYGTLVI

DGVTPNMIDYFGRPYPGIAVFDGKQITVTGTLWNGNKIYDERLINPD

WT OgLuc β9 (SEQ ID NO: 3):
GSLLFRVTIN

WT OgLuc β10 (SEQ ID NO: 4):
GVTGWRLCENILA

NANOLUC (SEQ ID NO: 5):
MVFTLEDFVGDWRQTAGYNLDQVLEQGGVSSLFQNLGVSVTPIQRIVLSG

ENGLKIDIHVIIPYEGLSGDQMGQIEKIFKVVYPVDDHHFKVILHYGTLV

IDGVTPNMIDYFGRPYEGIAVFDGKKITVTGTLWNGNKIIDERLINPDGS

LLFRVTINGVTGWRLCERILA

NANOLUC Lg (SEQ ID NO: 6):
MVFTLEDFVGDWRQTAGYNLDQVLEQGGVSSLFQNLGVSVTPIQRIVLSG

ENGLKIDIHVIIPYEGLSGDQMGQIEKIFKVVYPVDDHHFKVILHYGTLV

IDGVTPNMIDYFGRPYEGIAVFDGKKITVTGTLWNGNKIIDERLINPD

NANOLUC β9 (SEQ ID NO: 7):
GSLLFRVTINV

NANOLUC β10 (SEQ ID NO: 8):
GVTGWRLCERILA

LgBiT (SEQ ID NO: 9):
MVFTLEDFVGDWRQTAGYNLDQVLEQGGVSSLFQNLGVSVTPIQRIVLSG

ENGLKIDIHVIIPYEGLSGDQMGQIEKIFKVVYPVDDHHFKVILHYGTLV

IDGVTPNMIDYFGRPYEGIAVFDGKKITVTGTLWNGNKIIDERLINPDGS

LLFRVTIN

SmBiT (SEQ ID NO: 10):
VTGYRLFEEIL

HiBiT (SEQ ID NO: 11):
VSGWRLFKKIS

SEQUENCES

LgTrip (3546) (SEQ ID NO: 12):
MKHEIHEIHEVFTLDDFVGDWEQTAAYNLDQVLEQGGVSSLLQNLAVSVT
PIMRIVRSGENALKIDIHVIIPYEGLSADQMAQIEEVFKVVYPVDDHHFK
VILPYGTLVIDGVTPNKLNYFGRPYEGIAVFDGKKITTTGTLWNGNKIID
ERLITPD SmTrip9 (SEQ ID NO: 13):
GSMLFRVTINS β9/β10 dipeptide (SEQ ID NO: 14):
GSMLFRVTINSVSGWRLFKKIS SmTrip10 (SEQ ID NO: 15):
VSGWRLFKKIS HALOTAG (SEQ ID NO: 16):
MAEIGTGFPFDPHYVEVLGERMHYVDVGPRDGTPVLFLHGNPTSSYVWRN
IIPHVAPTHRCIAPDLIGMGKSDKPDLGYFFDDHVRFMDAFIEALGLEEV
VLVIHDWGSALGFHWAKRNPERVKGIAFMEFIRPIPTWDEWPEFARETFQ
AFRTTDVGRKLIIDQNVFIEGTLPMGVVRPLTEVEMDHYREPFLNPVDRE
PLWRFPNELPIAGEPANIVALVEEYMDWLHQSPVPKLLFWGTPGVLIPPA
EAARLAKSLPNCKAVDIGPGLNLLQEDNPDLIGSEIARWLSTLEISG Collective base sequence of bioluminescent complex
(SEQ ID NO: 17):
MVFTLDDFVGDWEQTAAYNLDQVLEQGGVSSLLQNLAVSVTPIMRIVRSG
ENALKIDIHVIIPYEGLSADQMAQIEEVFKVVYPVDDHHFKVILPYGTLV
IDGVTPNKLNYFGRPYEGIAVFDGKKITTTGTLWNGNKIIDERLITPDGS
MLFRVTINSVTGYRLFEEIL WT strand 9 - SmBiT (SEQ ID NO: 18):
GSMLFRVTINSVTGYRLFEEIL LgTrip 3546 (1-8) (SEQ ID NO: 19):
MVFTLDDFVGDWEQTAAYNLDQVLEQGGVSSLLQNLAVSVTPIMRIVRSG
ENALKIDIHVIIPYEGLSADQMAQIEEVFKVVYPVDDHHFKVILPYGTLV
IDGVTPNKLNYFGRPYEGIAVFDGKKITTTGTLWNGNKIIDERLITPD

---

What is claimed is:

1. A method of labeling a cell comprising contacting the cell with an effective amount of the compound of formula A-X-B, or a salt thereof, wherein A is a haloalkyl capture element of the structure —$(CH_2)_n$-halogen, wherein n is 4-8; X is a linker comprising

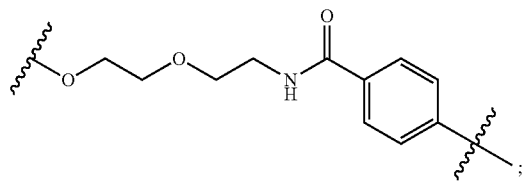 [SMILES: *OCCOCCNC(=O)c1ccc(*)cc1]

and B is a biomolecule-reactive group comprising a succinimidyl ester or maleimide group, wherein the biomolecule-reactive group forms a covalent bond with a cell-associated biomolecule on or within the cell, thereby labeling the cell; wherein the wavy line linked to the benzene ring of the linker indicates point of linkage to the biomolecule reactive group and the wavy line linked to the oxygen atom of the linker indicates point of linkage to the haloalkyl capture element.

2. The method of claim 1, the method further comprising:
contacting the cell with a set of capture/detection reagents; wherein a first capture/detection reagent comprises: (i) one of a complementary peptide or a complementary polypeptide component of a bioluminescent complex linked to (ii) a capture agent capable of stably binding to the capture element; wherein a second capture/detection reagent comprises: (i) the other of a complementary peptide or a complementary polypeptide component of a bioluminescent complex linked to (ii) one of: a capture agent capable of stably binding to the capture element, or a binding agent capable of binding directly to cell-associated biomolecules on the cell;
(c) contacting the cell with a substrate for the bioluminescent complex; and
(d) monitoring and/or detecting bioluminescence.

3. The method of claim 1, the method further comprising:
removing unincorporated probe from contact with the cell.

4. The method of claim 1, the method further comprising:
contacting the cell with a first capture/detection reagent comprising (i) a complementary polypeptide component of a bioluminescent complex linked to (ii) a capture agent capable of stably binding to the capture element;
contacting the cell with a second capture/detection reagent comprising (i) a complementary peptide component of a bioluminescent complex linked to (ii) a capture agent capable of stably binding to the capture element; wherein the polypeptide component and the peptide component are capable of forming a bioluminescent complex when brought into proximity of each other;
contacting the cell with a substrate for the bioluminescent complex; and
monitoring and/or detecting bioluminescence.

5. The method of claim 1, the method further comprising:
contacting the cell with a first capture/detection reagent comprising (i) a complementary polypeptide or a peptide component of a bioluminescent complex and (ii) a capture agent capable of stably binding to the capture element;
contacting the cell with a second non-covalent binding/detection reagent comprising (i) a complementary peptide or polypeptide component of a bioluminescent complex and (ii) a binding agent capable of directly binding to a biomolecule on the cell; wherein the polypeptide component and the peptide component are capable of forming a bioluminescent complex when brought into proximity of each other;
contacting the cell with a substrate for the bioluminescent complex; and
monitoring and/or detecting bioluminescence.

6. The method of claim 1, the method further comprising:
removing unincorporated probe and dead cells from the population of labelled live cells;
fixing and permeabilizing the population of labelled live cells;
contacting the fixed and permeabilized cell population with a first capture/detection reagent comprising: (i) a complementary polypeptide component of a bioluminescent complex linked to (ii) a capture agent of stably binding to the capture element;
contacting the fixed and permeabilized cell population with a second capture/detection reagent comprising: (i) a complementary peptide component of a bioluminescent complex linked to (ii) a fluorophore; wherein the polypeptide component and the peptide component are capable of forming a bioluminescent complex; and
detecting luminescence and/or fluorescence.

7. The method of claim 1, the method further comprising:
contacting the cell with a first capture/detection reagent comprising (i) a capture agent capable of stably binding to the capture element linked to (ii) a first complementary peptide or polypeptide component of a bioluminescent complex;
contacting the cell with a second capture/detection reagent comprising (i) a second biomolecule-reactive group capable of stably binding to a second biomolecule linked to (ii) a second complementary peptide or polypeptide component of the bioluminescent complex;
contacting the cell with a substrate for the bioluminescent complex;
exposing the cell to a stimulus or condition;
allowing the capture/detection reagents to bind to the capture element and second biomolecule, respectively, wherein binding of capture/detection reagents at adjacent positions will result in the formation of the bioluminescent complex; and monitoring and/or detecting bioluminescence, in the presence of a bioluminescence substrate, wherein the amount of bioluminescence is proportional to the amount of biomolecules on the outer surface of the cell.

8. The method of claim 1, the method further comprising:
washing the cell to remove unbound probe from the cell;
contacting the cell with a first capture/detection reagent comprising (i) a capture agent capable of stably binding to the capture element linked to (ii) a first complementary peptide or polypeptide component of a bioluminescent complex;
contacting the cell with a second capture/detection reagent comprising (i) a second biomolecule-reactive/binding group or capable of stably binding to a second biomolecule linked to (ii) and a second complementary peptide or polypeptide component of the bioluminescent complex;
exposing the cell to a stimulus or condition;
contacting the cell with a substrate for the bioluminescent complex;
allowing the capture/detection reagents to bind to the capture element and second biomolecule, respectively, wherein binding of capture/detection reagents at adjacent positions will result in the formation of the bioluminescent complex; and
monitoring and/or detecting bioluminescence, in the presence of a bioluminescence substrate.

9. The method of claim 1, the method further comprising:
contacting the cell with a capture/detection reagent comprising a capture agent capable of stably binding to the capture element linked to a complementary peptide or polypeptide component of a bioluminescent complex;
contacting the cell with a detection reagent comprising a fluorophore tethered to the other of the complementary peptide and polypeptide components of a bioluminescent complex;
contacting the cell with a substrate for the bioluminescent complex;
allowing the capture/detection reagent to bind to the capture elements and allowing the detection reagent to form a bioluminescent complex with the capture/detection reagent;
monitoring and/or detecting fluorescence from the fluorophore and/or bioluminescence, in the presence of a bioluminescence substrate, from the bioluminescent complex.

\* \* \* \* \*

SEQUENCE LISTING

```
<160> NUMBER OF SEQ ID NOS: 19

<210> SEQ ID NO 1
<211> LENGTH: 170
<212> TYPE: PRT
<213> ORGANISM: Oplophorus gracilirostris

<400> SEQUENCE: 1

Met Phe Thr Leu Ala Asp Phe Val Gly Asp Trp Gln Gln Thr Ala Gly
1               5                   10                  15

Tyr Asn Gln Asp Gln Val Leu Glu Gln Gly Gly Leu Ser Ser Leu Phe
            20                  25                  30

Gln Ala Leu Gly Val Ser Val Thr Pro Ile Gln Lys Val Val Leu Ser
        35                  40                  45

Gly Glu Asn Gly Leu Lys Ala Asp Ile His Val Ile Pro Tyr Glu
    50                  55                  60

Gly Leu Ser Gly Phe Gln Met Gly Leu Ile Glu Met Ile Phe Lys Val
65                  70                  75                  80

Val Tyr Pro Val Asp Asp His His Phe Lys Ile Ile Leu His Tyr Gly
                85                  90                  95

Thr Leu Val Ile Asp Gly Val Thr Pro Asn Met Ile Asp Tyr Phe Gly
            100                 105                 110

Arg Pro Tyr Pro Gly Ile Ala Val Phe Asp Gly Lys Gln Ile Thr Val
        115                 120                 125

Thr Gly Thr Leu Trp Asn Gly Asn Lys Ile Tyr Asp Glu Arg Leu Ile
    130                 135                 140

Asn Pro Asp Gly Ser Leu Leu Phe Arg Val Thr Ile Asn Gly Val Thr
145                 150                 155                 160

Gly Trp Arg Leu Cys Glu Asn Ile Leu Ala
                165                 170

<210> SEQ ID NO 2
<211> LENGTH: 147
```

```
<212> TYPE: PRT
<213> ORGANISM: Oplophorus gracilirostris

<400> SEQUENCE: 2

Met Phe Thr Leu Ala Asp Phe Val Gly Asp Trp Gln Gln Thr Ala Gly
1               5                   10                  15

Tyr Asn Gln Asp Gln Val Leu Glu Gln Gly Gly Leu Ser Ser Leu Phe
                20                  25                  30

Gln Ala Leu Gly Val Ser Val Thr Pro Ile Gln Lys Val Val Leu Ser
            35                  40                  45

Gly Glu Asn Gly Leu Lys Ala Asp Ile His Val Ile Ile Pro Tyr Glu
50                  55                  60

Gly Leu Ser Gly Phe Gln Met Gly Leu Ile Glu Met Ile Phe Lys Val
65                  70                  75                  80

Val Tyr Pro Val Asp Asp His Phe Lys Ile Leu His Tyr Gly
                85                  90                  95

Thr Leu Val Ile Asp Gly Val Thr Pro Asn Met Ile Asp Tyr Phe Gly
                100                 105                 110

Arg Pro Tyr Pro Gly Ile Ala Val Phe Asp Gly Lys Gln Ile Thr Val
            115                 120                 125

Thr Gly Thr Leu Trp Asn Gly Asn Lys Ile Tyr Asp Glu Arg Leu Ile
130                 135                 140

Asn Pro Asp
145

<210> SEQ ID NO 3
<211> LENGTH: 10
<212> TYPE: PRT
<213> ORGANISM: Oplophorus gracilirostris

<400> SEQUENCE: 3

Gly Ser Leu Leu Phe Arg Val Thr Ile Asn
1               5                   10

<210> SEQ ID NO 4
<211> LENGTH: 13
<212> TYPE: PRT
<213> ORGANISM: Oplophorus gracilirostris

<400> SEQUENCE: 4

Gly Val Thr Gly Trp Arg Leu Cys Glu Asn Ile Leu Ala
1               5                   10

<210> SEQ ID NO 5
<211> LENGTH: 171
<212> TYPE: PRT
<213> ORGANISM: Artificial sequence
<220> FEATURE:
<223> OTHER INFORMATION: Synthetic

<400> SEQUENCE: 5

Met Val Phe Thr Leu Glu Asp Phe Val Gly Asp Trp Arg Gln Thr Ala
1               5                   10                  15

Gly Tyr Asn Leu Asp Gln Val Leu Glu Gln Gly Gly Val Ser Ser Leu
                20                  25                  30

Phe Gln Asn Leu Gly Val Ser Val Thr Pro Ile Gln Arg Ile Val Leu
            35                  40                  45

Ser Gly Glu Asn Gly Leu Lys Ile Asp Ile His Val Ile Ile Pro Tyr
50                  55                  60
```

```
Glu Gly Leu Ser Gly Asp Gln Met Gly Gln Ile Glu Lys Ile Phe Lys
65                  70                  75                  80

Val Val Tyr Pro Val Asp Asp His His Phe Lys Val Ile Leu His Tyr
                85                  90                  95

Gly Thr Leu Val Ile Asp Gly Val Thr Pro Asn Met Ile Asp Tyr Phe
                100                 105                 110

Gly Arg Pro Tyr Glu Gly Ile Ala Val Phe Asp Gly Lys Lys Ile Thr
                115                 120                 125

Val Thr Gly Thr Leu Trp Asn Gly Asn Lys Ile Ile Asp Glu Arg Leu
                130                 135                 140

Ile Asn Pro Asp Gly Ser Leu Leu Phe Arg Val Thr Ile Asn Gly Val
145                 150                 155                 160

Thr Gly Trp Arg Leu Cys Glu Arg Ile Leu Ala
                165                 170
```

<210> SEQ ID NO 6
<211> LENGTH: 148
<212> TYPE: PRT
<213> ORGANISM: Artificial sequence
<220> FEATURE:
<223> OTHER INFORMATION: Synthetic

<400> SEQUENCE: 6

```
Met Val Phe Thr Leu Glu Asp Phe Val Gly Asp Trp Arg Gln Thr Ala
1               5                   10                  15

Gly Tyr Asn Leu Asp Gln Val Leu Glu Gln Gly Gly Val Ser Ser Leu
                20                  25                  30

Phe Gln Asn Leu Gly Val Ser Val Thr Pro Ile Gln Arg Ile Val Leu
                35                  40                  45

Ser Gly Glu Asn Gly Leu Lys Ile Asp Ile His Val Ile Ile Pro Tyr
50                  55                  60

Glu Gly Leu Ser Gly Asp Gln Met Gly Gln Ile Glu Lys Ile Phe Lys
65                  70                  75                  80

Val Val Tyr Pro Val Asp Asp His His Phe Lys Val Ile Leu His Tyr
                85                  90                  95

Gly Thr Leu Val Ile Asp Gly Val Thr Pro Asn Met Ile Asp Tyr Phe
                100                 105                 110

Gly Arg Pro Tyr Glu Gly Ile Ala Val Phe Asp Gly Lys Lys Ile Thr
                115                 120                 125

Val Thr Gly Thr Leu Trp Asn Gly Asn Lys Ile Ile Asp Glu Arg Leu
                130                 135                 140

Ile Asn Pro Asp
145
```

<210> SEQ ID NO 7
<211> LENGTH: 11
<212> TYPE: PRT
<213> ORGANISM: Artificial sequence
<220> FEATURE:
<223> OTHER INFORMATION: Synthetic

<400> SEQUENCE: 7

```
Gly Ser Leu Leu Phe Arg Val Thr Ile Asn Val
1               5                   10
```

<210> SEQ ID NO 8
<211> LENGTH: 13
<212> TYPE: PRT
<213> ORGANISM: Artificial sequence

```
<220> FEATURE:
<223> OTHER INFORMATION: Synthetic

<400> SEQUENCE: 8

Gly Val Thr Gly Trp Arg Leu Cys Glu Arg Ile Leu Ala
1               5                   10

<210> SEQ ID NO 9
<211> LENGTH: 158
<212> TYPE: PRT
<213> ORGANISM: Artificial sequence
<220> FEATURE:
<223> OTHER INFORMATION: Synthetic

<400> SEQUENCE: 9

Met Val Phe Thr Leu Glu Asp Phe Val Gly Asp Trp Arg Gln Thr Ala
1               5                   10                  15

Gly Tyr Asn Leu Asp Gln Val Leu Glu Gln Gly Gly Val Ser Ser Leu
            20                  25                  30

Phe Gln Asn Leu Gly Val Ser Val Thr Pro Ile Gln Arg Ile Val Leu
        35                  40                  45

Ser Gly Glu Asn Gly Leu Lys Ile Asp Ile His Val Ile Ile Pro Tyr
    50                  55                  60

Glu Gly Leu Ser Gly Asp Gln Met Gly Gln Ile Glu Lys Ile Phe Lys
65                  70                  75                  80

Val Val Tyr Pro Val Asp Asp His His Phe Lys Val Ile Leu His Tyr
                85                  90                  95

Gly Thr Leu Val Ile Asp Gly Val Thr Pro Asn Met Ile Asp Tyr Phe
            100                 105                 110

Gly Arg Pro Tyr Glu Gly Ile Ala Val Phe Asp Gly Lys Lys Ile Thr
        115                 120                 125

Val Thr Gly Thr Leu Trp Asn Gly Asn Lys Ile Ile Asp Glu Arg Leu
    130                 135                 140

Ile Asn Pro Asp Gly Ser Leu Leu Phe Arg Val Thr Ile Asn
145                 150                 155

<210> SEQ ID NO 10
<211> LENGTH: 11
<212> TYPE: PRT
<213> ORGANISM: Artificial sequence
<220> FEATURE:
<223> OTHER INFORMATION: Synthetic

<400> SEQUENCE: 10

Val Thr Gly Tyr Arg Leu Phe Glu Glu Ile Leu
1               5                   10

<210> SEQ ID NO 11
<211> LENGTH: 11
<212> TYPE: PRT
<213> ORGANISM: Artificial sequence
<220> FEATURE:
<223> OTHER INFORMATION: Synthetic

<400> SEQUENCE: 11

Val Ser Gly Trp Arg Leu Phe Lys Lys Ile Ser
1               5                   10

<210> SEQ ID NO 12
<211> LENGTH: 155
<212> TYPE: PRT
<213> ORGANISM: Artificial sequence
```

<220> FEATURE:
<223> OTHER INFORMATION: Synthetic

<400> SEQUENCE: 12

Met Lys His His His His His Val Phe Thr Leu Asp Asp Phe Val
1               5                   10                  15

Gly Asp Trp Glu Gln Thr Ala Ala Tyr Asn Leu Asp Gln Val Leu Glu
            20                  25                  30

Gln Gly Gly Val Ser Ser Leu Leu Gln Asn Leu Ala Val Ser Val Thr
        35                  40                  45

Pro Ile Met Arg Ile Val Arg Ser Gly Glu Asn Ala Leu Lys Ile Asp
    50                  55                  60

Ile His Val Ile Ile Pro Tyr Glu Gly Leu Ser Ala Asp Gln Met Ala
65                  70                  75                  80

Gln Ile Glu Glu Val Phe Lys Val Val Tyr Pro Val Asp Asp His His
                85                  90                  95

Phe Lys Val Ile Leu Pro Tyr Gly Thr Leu Val Ile Asp Gly Val Thr
            100                 105                 110

Pro Asn Lys Leu Asn Tyr Phe Gly Arg Pro Tyr Glu Gly Ile Ala Val
        115                 120                 125

Phe Asp Gly Lys Lys Ile Thr Thr Thr Gly Thr Leu Trp Asn Gly Asn
    130                 135                 140

Lys Ile Ile Asp Glu Arg Leu Ile Thr Pro Asp
145                 150                 155

<210> SEQ ID NO 13
<211> LENGTH: 11
<212> TYPE: PRT
<213> ORGANISM: Artificial sequence
<220> FEATURE:
<223> OTHER INFORMATION: Synthetic

<400> SEQUENCE: 13

Gly Ser Met Leu Phe Arg Val Thr Ile Asn Ser
1               5                   10

<210> SEQ ID NO 14
<211> LENGTH: 22
<212> TYPE: PRT
<213> ORGANISM: Artificial sequence
<220> FEATURE:
<223> OTHER INFORMATION: Synthetic

<400> SEQUENCE: 14

Gly Ser Met Leu Phe Arg Val Thr Ile Asn Ser Val Ser Gly Trp Arg
1               5                   10                  15

Leu Phe Lys Lys Ile Ser
            20

<210> SEQ ID NO 15
<211> LENGTH: 11
<212> TYPE: PRT
<213> ORGANISM: Artificial sequence
<220> FEATURE:
<223> OTHER INFORMATION: Synthetic

<400> SEQUENCE: 15

Val Ser Gly Trp Arg Leu Phe Lys Lys Ile Ser
1               5                   10

<210> SEQ ID NO 16

```
<211> LENGTH: 297
<212> TYPE: PRT
<213> ORGANISM: Artificial sequence
<220> FEATURE:
<223> OTHER INFORMATION: Synthetic

<400> SEQUENCE: 16

Met Ala Glu Ile Gly Thr Gly Phe Pro Phe Asp Pro His Tyr Val Glu
1               5                   10                  15

Val Leu Gly Glu Arg Met His Tyr Val Asp Val Gly Pro Arg Asp Gly
            20                  25                  30

Thr Pro Val Leu Phe Leu His Gly Asn Pro Thr Ser Ser Tyr Val Trp
        35                  40                  45

Arg Asn Ile Ile Pro His Val Ala Pro Thr His Arg Cys Ile Ala Pro
50                  55                  60

Asp Leu Ile Gly Met Gly Lys Ser Asp Lys Pro Asp Leu Gly Tyr Phe
65                  70                  75                  80

Phe Asp Asp His Val Arg Phe Met Asp Ala Phe Ile Glu Ala Leu Gly
                85                  90                  95

Leu Glu Glu Val Val Leu Val Ile His Asp Trp Gly Ser Ala Leu Gly
            100                 105                 110

Phe His Trp Ala Lys Arg Asn Pro Glu Arg Val Lys Gly Ile Ala Phe
        115                 120                 125

Met Glu Phe Ile Arg Pro Ile Pro Thr Trp Asp Glu Trp Pro Glu Phe
130                 135                 140

Ala Arg Glu Thr Phe Gln Ala Phe Arg Thr Thr Asp Val Gly Arg Lys
145                 150                 155                 160

Leu Ile Ile Asp Gln Asn Val Phe Ile Glu Gly Thr Leu Pro Met Gly
                165                 170                 175

Val Val Arg Pro Leu Thr Glu Val Glu Met Asp His Tyr Arg Glu Pro
            180                 185                 190

Phe Leu Asn Pro Val Asp Arg Glu Pro Leu Trp Arg Phe Pro Asn Glu
        195                 200                 205

Leu Pro Ile Ala Gly Glu Pro Ala Asn Ile Val Ala Leu Val Glu Glu
210                 215                 220

Tyr Met Asp Trp Leu His Gln Ser Pro Val Pro Lys Leu Leu Phe Trp
225                 230                 235                 240

Gly Thr Pro Gly Val Leu Ile Pro Pro Ala Glu Ala Ala Arg Leu Ala
                245                 250                 255

Lys Ser Leu Pro Asn Cys Lys Ala Val Asp Ile Gly Pro Gly Leu Asn
            260                 265                 270

Leu Leu Gln Glu Asp Asn Pro Asp Leu Ile Gly Ser Glu Ile Ala Arg
        275                 280                 285

Trp Leu Ser Thr Leu Glu Ile Ser Gly
290                 295

<210> SEQ ID NO 17
<211> LENGTH: 170
<212> TYPE: PRT
<213> ORGANISM: Artificial sequence
<220> FEATURE:
<223> OTHER INFORMATION: Synthetic

<400> SEQUENCE: 17

Met Val Phe Thr Leu Asp Asp Phe Val Gly Asp Trp Glu Gln Thr Ala
1               5                   10                  15

Ala Tyr Asn Leu Asp Gln Val Leu Glu Gln Gly Gly Val Ser Ser Leu
```

```
                    20                  25                  30

Leu Gln Asn Leu Ala Val Ser Val Thr Pro Ile Met Arg Ile Val Arg
            35                  40                  45

Ser Gly Glu Asn Ala Leu Lys Ile Asp Ile His Val Ile Pro Tyr
        50                  55                  60

Glu Gly Leu Ser Ala Asp Gln Met Ala Gln Ile Glu Val Phe Lys
65                  70                  75                  80

Val Val Tyr Pro Val Asp Asp His His Phe Lys Val Ile Leu Pro Tyr
                85                  90                  95

Gly Thr Leu Val Ile Asp Gly Val Thr Pro Asn Lys Leu Asn Tyr Phe
            100                 105                 110

Gly Arg Pro Tyr Glu Gly Ile Ala Val Phe Asp Gly Lys Lys Ile Thr
        115                 120                 125

Thr Thr Gly Thr Leu Trp Asn Gly Asn Lys Ile Ile Asp Glu Arg Leu
    130                 135                 140

Ile Thr Pro Asp Gly Ser Met Leu Phe Arg Val Thr Ile Asn Ser Val
145                 150                 155                 160

Thr Gly Tyr Arg Leu Phe Glu Glu Ile Leu
                165                 170

<210> SEQ ID NO 18
<211> LENGTH: 22
<212> TYPE: PRT
<213> ORGANISM: Artificial sequence
<220> FEATURE:
<223> OTHER INFORMATION: Synthetic

<400> SEQUENCE: 18

Gly Ser Met Leu Phe Arg Val Thr Ile Asn Ser Val Thr Gly Tyr Arg
1               5                   10                  15

Leu Phe Glu Glu Ile Leu
            20

<210> SEQ ID NO 19
<211> LENGTH: 148
<212> TYPE: PRT
<213> ORGANISM: Artificial sequence
<220> FEATURE:
<223> OTHER INFORMATION: Synthetic

<400> SEQUENCE: 19

Met Val Phe Thr Leu Asp Asp Phe Val Gly Asp Trp Glu Gln Thr Ala
1               5                   10                  15

Ala Tyr Asn Leu Asp Gln Val Leu Glu Gln Gly Gly Val Ser Ser Leu
            20                  25                  30

Leu Gln Asn Leu Ala Val Ser Val Thr Pro Ile Met Arg Ile Val Arg
        35                  40                  45

Ser Gly Glu Asn Ala Leu Lys Ile Asp Ile His Val Ile Pro Tyr
    50                  55                  60

Glu Gly Leu Ser Ala Asp Gln Met Ala Gln Ile Glu Val Phe Lys
65                  70                  75                  80

Val Val Tyr Pro Val Asp Asp His His Phe Lys Val Ile Leu Pro Tyr
                85                  90                  95

Gly Thr Leu Val Ile Asp Gly Val Thr Pro Asn Lys Leu Asn Tyr Phe
            100                 105                 110

Gly Arg Pro Tyr Glu Gly Ile Ala Val Phe Asp Gly Lys Lys Ile Thr
        115                 120                 125
```

-continued

```
Thr Thr Gly Thr Leu Trp Asn Gly Asn Lys Ile Ile Asp Glu Arg Leu
    130                 135                 140
Ile Thr Pro Asp
145
```